(12) United States Patent
Dominique et al.

(10) Patent No.: US 7,989,454 B2
(45) Date of Patent: Aug. 2, 2011

(54) LEUKOTRIENE B4 INHIBITORS

(75) Inventors: Romyr Dominique, Wayne, NJ (US); Robert Alan Goodnow, Jr., Gillette, NJ (US); Agnieszka Kowalczyk, Mine Hill, NJ (US); Qi Qiao, Bloomfield, NJ (US); Achyutharao Sidduri, Livingston, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 413 days.

(21) Appl. No.: 12/326,349

(22) Filed: Dec. 2, 2008

(65) Prior Publication Data
US 2009/0253684 A1 Oct. 8, 2009

Related U.S. Application Data

(60) Provisional application No. 61/007,892, filed on Dec. 17, 2002.

(51) Int. Cl.
*A61K 31/497* (2006.01)
*C07D 241/04* (2006.01)
(52) U.S. Cl. .................... 514/252.12; 544/358
(58) Field of Classification Search ............ 514/252.12; 544/358
See application file for complete search history.

(56) References Cited

U.S. PATENT DOCUMENTS
5,457,124 A * 10/1995 Cohen et al. ............... 514/456

OTHER PUBLICATIONS

Prostaglandins, Leukotrienes and Essential Fatty Acids 69, 2003, 123-13.
*Bioorganic & Medicinal Chemistry Letters* 1994, 4, 2883-8.

* cited by examiner

*Primary Examiner* — Rei-tsang Shiao
(74) *Attorney, Agent, or Firm* — George E. Johnston; Dennis P. Tramaloni; Samuel H. Megerditchian

(57) ABSTRACT

Provided herein are compounds of the formula (I):

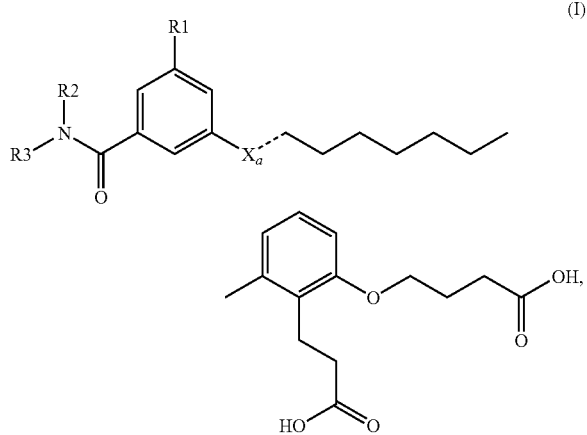

as well as pharmaceutically acceptable salts thereof, wherein the substituents are as those disclosed in the specification. These compounds, and the pharmaceutical compositions containing them, are useful for the treatment of diseases such as, for example, COPD.

15 Claims, No Drawings

LEUKOTRIENE B4 INHIBITORS

PRIORITY TO RELATED APPLICATION(S)

This application claims the benefit of U.S. Provisional Application No. 61/007,892, filed Dec. 17, 2007, which is hereby incorporated by reference in its entirety.

FIELD OF THE INVENTION

The invention is directed to compounds of formula I:

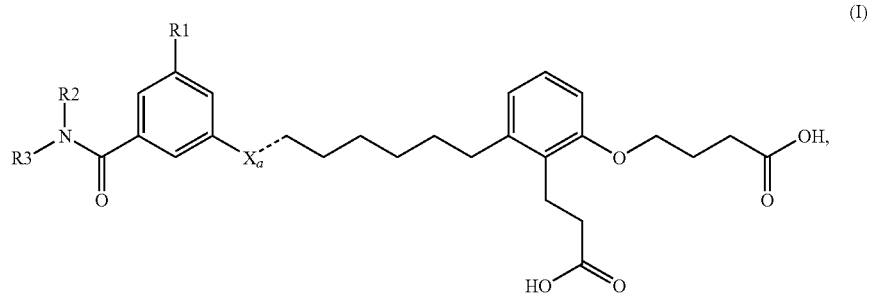

(I)

or pharmaceutically acceptable salts thereof.

All documents cited or relied upon below are expressly incorporated herein by reference.

BACKGROUND OF THE INVENTION $LTB_4$ is a potent pro-inflammatory lipid mediator derived from arachidonic acid through the 5-lipoxygenase signaling pathway. $LTB_4$ is produced by multiple cell types such as neutrophils, monocytes, macrophages, keratinocytes, lymphocytes and mast cells. It functions as a chemoattractant and as an activator of neutrophil cells. It has been shown that $LTB_4$ effects its action through the agonism of G-protein coupled receptors BLT-1 and BLT-2. (Prostaglandins, Leukotrienes and Essential Fatty Acids 69, 2003, 123-13

$LTB_4$ is considered to be an important mediator of acute and chronic inflammatory diseases. Increased levels of $LTB_4$ have been detected in the lungs of patients with severe asthma and COPD. Thus, it is anticipated that an effective inhibitor of the action of $LTB_4$ and BLT-1 and -2 would provide effective therapy for the treatment of inflammatory conditions such as asthma and COPD.

A need exists in the art for $LTB_4$ inhibitors that have efficacy for the treatment of diseases such as COPD.

SUMMARY OF THE INVENTION

The present invention pertains to inhibitors of $LTB_4$. Preferably, the invention provides for pharmaceutical compounds of the formula I:

(1)

as well as pharmaceutically acceptable salts thereof, and pharmaceutical compositions. These compounds are useful as inhibitors of the interaction of leukotriene $B_4$ ($LTB_4$) pro-inflammatory lipid mediator binding to BLT-1 and BLT-2 receptors, resulting in amelioration of disease states having an excessive inflammatory response, such as, for example, severe asthma and chronic obstructive pulmonary disease (COPD).

DETAILED DESCRIPTION

In a preferred embodiment, provided are compounds of formula (I):

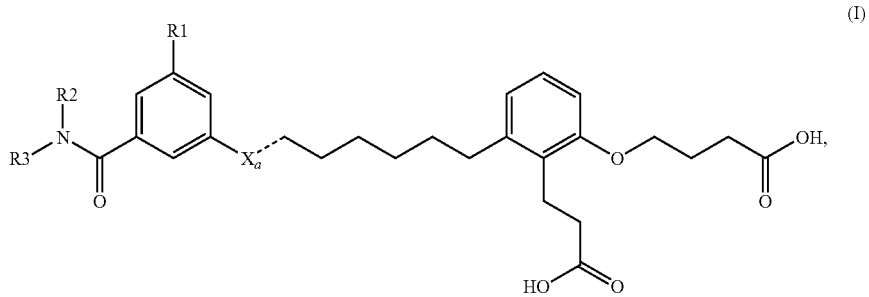

wherein:

R¹ is
- phenyl, unsubstituted or mono- or bi-substituted with alkoxy, halogen, hydroxy, lower alkyl, amino or amino-lower alkyl,
- heteroaryl, unsubstituted or substituted with lower alkyl or halogen,
- benzo[1,3]dioxole, unsubstituted or substituted with lower alkyl,
- dihydro-benzo[1,4]dioxine, unsubstituted or substituted with lower alkyl,
- benzo[b][1,4]dioxepine, unsubstituted or substituted with lower alkyl,
- benzofuran, unsubstituted or substituted with lower alkyl, or
- benzo[1,4]oxazin, unsubstituted or substituted with lower alkyl;

R² and R³, independently of each other, are:
- hydrogen,
- lower alkyl,
- cycloalkyl,
- phenyl,
- lower alkyl-cycloalkyl,
- lower alkyl-heteroaryl,
- lower alkyl-alkoxy,
- alkoxy-lower alkyl,
- lower alkyl-heterocycloalkyl, unsubstituted or substituted with lower alkyl,
- C(O)-amino,
- lower alkyl-phenyl, said phenyl being unsubstituted or mono- or bi-substituted with lower alkyl, halogen, alkoxy or O-haloloweralkyl,
- benzo[1,3]dioxole, unsubstituted or substituted with lower alkyl,
- dihydro-benzo[1,4]dioxine, unsubstituted or substituted with lower alkyl,
- benzo[b][1,4]dioxepine, unsubstituted or substituted with lower alkyl,
- benzofuran, unsubstituted or substituted with lower alkyl,
- benzo[1,4]oxazin, unsubstituted or substituted with lower alkyl,
- CH₂-benzo[1,3]dioxole, unsubstituted or substituted with lower alkyl,
- CH₂-dihydro-benzo[1,4]dioxine, unsubstituted or substituted with lower alkyl,
- CH₂-benzo[b][1,4]dioxepine, unsubstituted or substituted with lower alkyl,
- CH₂-benzofuran, unsubstituted or substituted with lower alkyl
- CH₂-benzo[1,4]oxazin, unsubstituted or substituted with lower alkyl, or R² and R³, together with the nitrogen atom to which they are attached, form a heterocycloalkyl ring, optionally having a second heteroatom from N, O or S, said heterocycloalkyl ring being unsubstituted or mono- or bi-substituted with halogen, lower alkyl, carbonyl, C(=O) or hydroxy;

X is O or C; and a is a single bond or an alkynyl bond, and pharmaceutically acceptable salts thereof.

In another embodiment, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent carbocyclic radical of three to seven, preferably three to six carbon atoms. This term is further exemplified by radicals such as cyclopropyl, cyclobutyl, cyclopentyl and cyclohexyl. In a preferred embodiment, the "cycloalkyl" moieties can optionally be substituted with one, two, three or four substituents, wherein each substituent is independently, for example, hydroxy, alkyl, alkoxy, halogen or amino, unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a cyclic alkyl ring, wherein one, two or three of the carbon ring atoms is replaced by a heteroatom such as N, O or S. Examples of heterocycloalkyl groups include, but are not limited to, morpholine, thiomorpholine, piperazine, piperidine and the like. The heterocycloalkyl groups may be unsubstituted or substituted.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic monovalent mono- or polycarbocyclic radical, such as phenyl or naphthyl, preferably phenyl.

The term "heteroaryl," alone or in combination with other groups, means a monocyclic or bicyclic radical of 5 to 12 ring atoms having at least one aromatic ring containing one, two, or three ring heteroatoms selected from N, O, and S, the remaining ring atoms being C. One or two ring carbon atoms of the heteroaryl group may be replaced with a carbonyl group. The heteroaryl group described above may be substituted independently with one, two, or three substituents, preferably one or two substituents such as, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means alkyl-O—; and "alkoyl" means alkyl-CO—. Alkoxy substituent groups or alkoxy-containing substituent groups may be substituted by, for example, one or more alkyl groups.

As used herein, the term "halogen" means a fluorine, chlorine, bromine or iodine radical, preferably a fluorine, chlorine or bromine radical, and more preferably a fluorine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

The compounds of the present invention can be prepared by any conventional means. Suitable processes for synthesizing these compounds are provided in the Examples. Generally, compounds of formula I can be prepared according to the Schemes described below. The sources of the starting materials for these reactions are also described.

Scheme 1

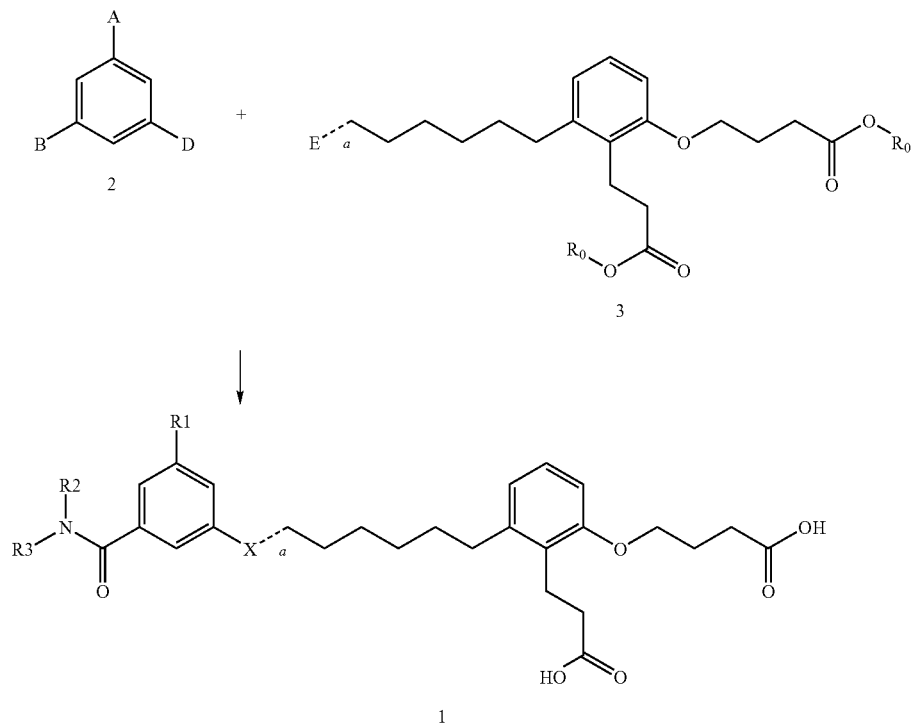

The compounds contained within this invention can be synthesized according to the following general synthetic strategies as shown below in Scheme 1. The synthesis of 1 may be effected by condensation of 3, 4-[2-(2-carboxy-ethyl)-3-(6-E-hexyl)-phenoxy]-butyric, protected as a di-ester for $R_0$=lower alkyl, preferably as a di-ethyl ester ($R_0$=ethyl), and E is a leaving group, such as a halogen or mesylate with the fragment 2 wherein D is a nucleophile such as a hydroxyl group under standard conditions employed for the alkylation of phenols with primary halides or mesylates. Functional groups represented by symbols A and B can be together or independently carboxylic acid, carboxylic acid ester, halogen, nitro, and amino and can be together or independently transformed to Aryl and amide function before or after coupling to 3 according to chemistry described in this invention. X can be oxygen or carbon. The bond indicated by "a" represents either a single oxygen-carbon bond where X is oxygen or a single carbon-carbon bond where X is carbon or a triple carbon-carbon bond where X is carbon.

A synthesis of 3 for E=Br and $R_0$=Et has been described in *Bioorganic & Medicinal Chemistry Letters* 1994, 4, 2883-8. A synthesis of 3 for E=Br and $R_0$=Et is also shown below in Schemes 2 and 3.

Scheme 2

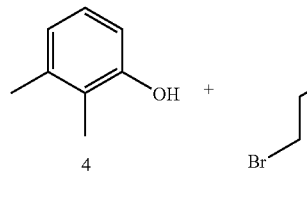 + 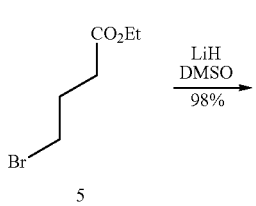 $\xrightarrow[98\%]{\text{LiH} \atop \text{DMSO}}$ 4                    5

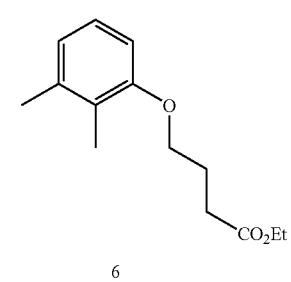 $\xrightarrow[71\%]{K_2S_2O_8 \atop CuSO_4 \atop H_2O, CH_3CN}$

6

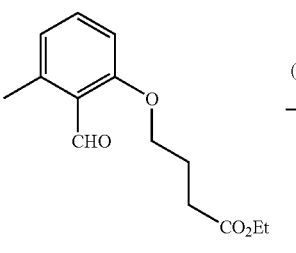 $\xrightarrow{(EtO)_2P(O)CH_2CO_2Et \atop (8)}$

7

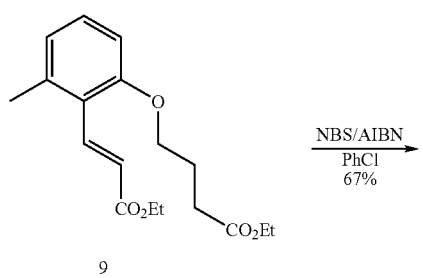 $\xrightarrow[67\%]{\text{NBS/AIBN} \atop \text{PhCl}}$

9

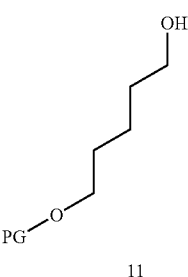

10

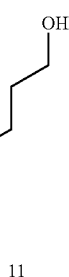 $\xrightarrow[87\%]{\text{Oxalyl chloride/} \atop \text{DMSO/CH2Cl2}}$

11

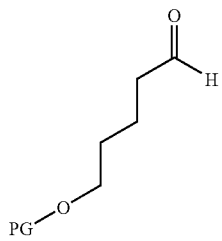

12

In Scheme 2, 2,3-dimethylphenol 4 is reacted with 4-bromo butyric acid ester 5 in presence of a base, preferably lithium hydride in aprotic solvent, preferably dimethylsulfoxide to obtain the dimethyl intermediate, 6. Then, the more reactive methyl group at 2-position of 6 is selectively oxidized to the corresponding aldehyde 7 using a oxidizing conditions, such as copper(II) sulfate pentahydrate and potassium persulfate in a mixed solvent systems, preferably water and acetonitrile. The two carbon chain ester moiety can be selectively introduced by a modified Horner-Emmons condensation conditions from aldehyde 7 and triethylphosphonoacetate (8) in the presence of a base such as sodium ethoxide in a protic solvents, preferably ethanol. Then, the benzylic bromination of 9 is effected with N-bromosuccinimide in the presence of 2,2'-azobisisobutyronitrile (AIBN) in a aprotic solvents such as carbon tetrachloride or chlorobenzene or benzene. The hydroxy protected 5-carbon chain aldehyde 12 can be obtained by oxidation of a mono protected pentane-1, 5-diol with any suitable oxidation conditions such as Swern oxidation or TEMPO oxidation, reactions well known to those skilled in the art. The protecting group on 11 and 12 can be any suitable protecting group for primary alcohols, for a example t-butyldimethylsilyl group. Use and removal of protecting groups is well presented in the literature. For a leading reference, see P. G. M. Wuts and T. W. Greene in Green's Protective Groups in Organic Synthesis, Wiley and Sons, 2007.

Scheme 3
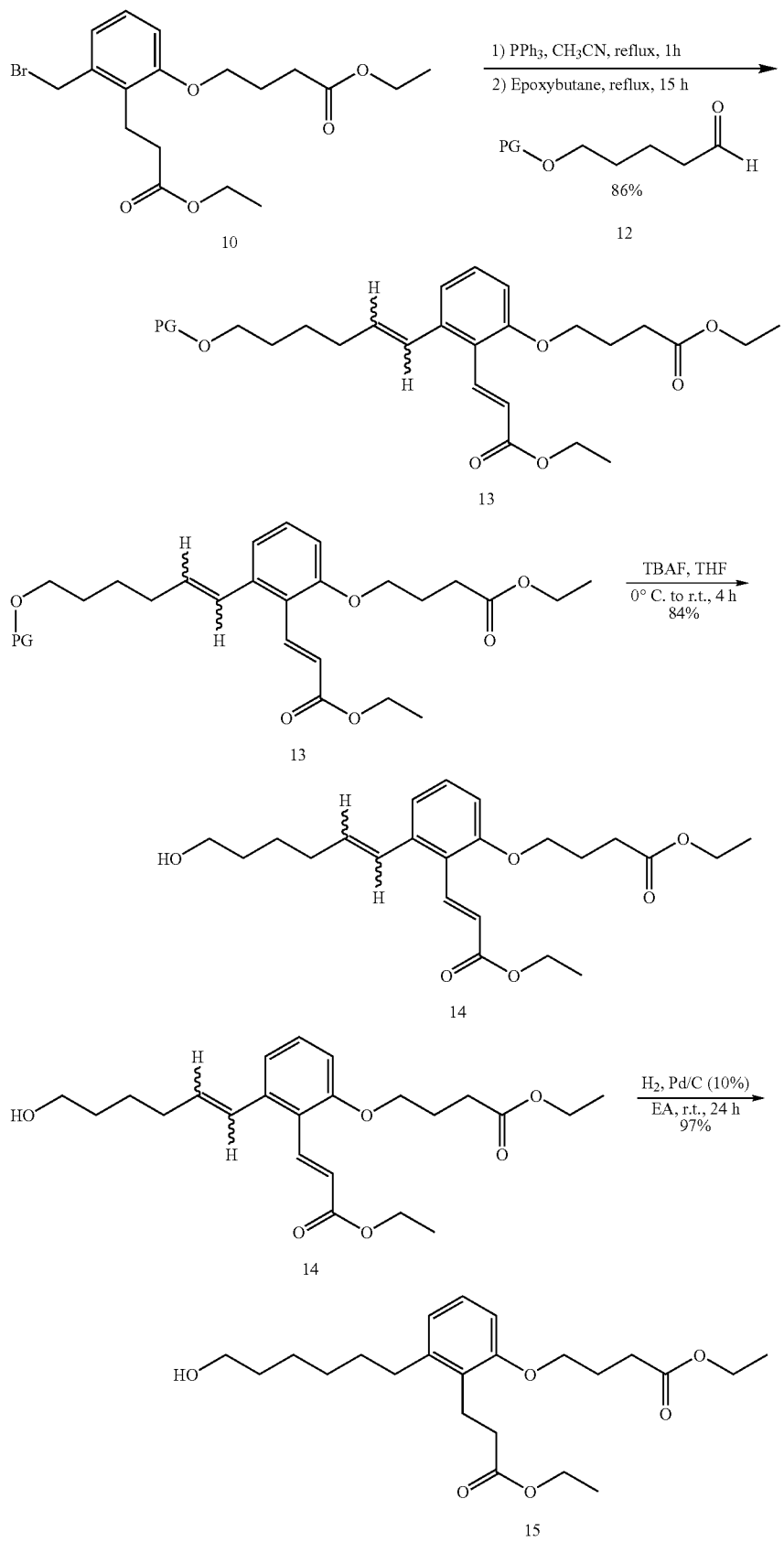

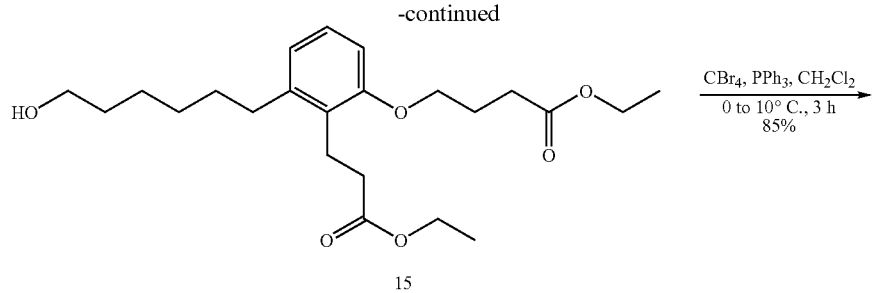

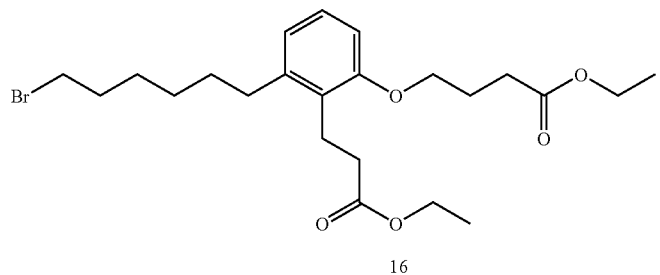

As shown in Scheme 3, a one-pot Wittig condensation reaction is conducted first by making an in situ Wittig salt from the benzylic bromide 10 and triphenylphosphine in acetonitrile and then the reaction of the resulting Wittig salt with the protected aldehyde 12 in 1,2-epoxybutane to obtain the olefinic intermediate 13 in a cis to trans ratio of ~1:3. The mixture of cis and trans compounds can be converted to the corresponding alkyl bromide intermediate 16 by removal of the protecting group, using for example tetrabutyl ammonium fluoride for the case wherein the protecting group is a t-butyldimethylsilyl group, hydrogenation of the double bonds, and conversion of the hydroxyl group to the bromide. These transformation are routine and well known to those skilled in the art.

Scheme 4: Method A

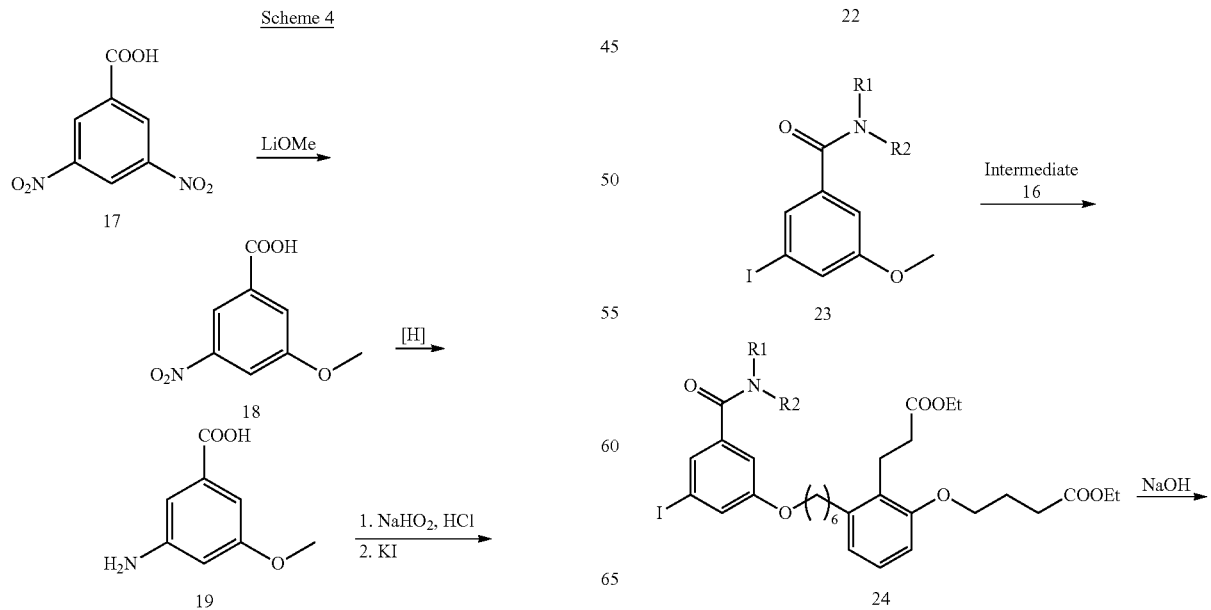

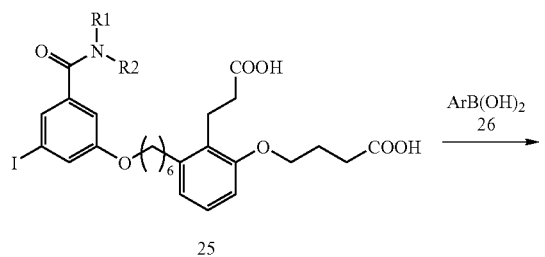

25

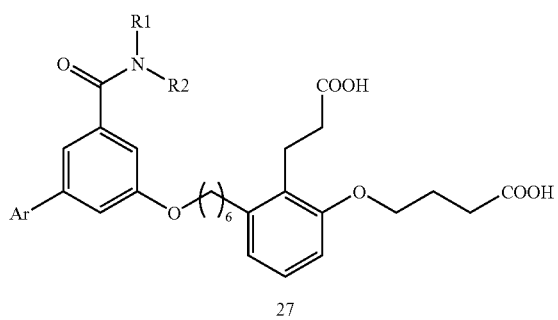

27

Commercially available 3,5-dinitrobenzoic acid (17) can be converted to 3-methoxy-5-nitrobenzoic acid (18) by a nucleophilic displacement of a nitro group with methoxide (as described in *Aust. J. Chem.* 1981, 34, 1319-24). A subsequent nitro group of intermediate 18 can be reduced to an amino group by catalytic hydrogenation or other methods known to those skilled in the art leading to intermediate 19. Catalytic hydrogenation with hydrogen gas is usually carried out in methanol, ethanol or tetrahydrofuran over palladium catalyst absorbed on carbon (content of Pd varies from 5% to 10%) in either Parr apparatus or an H-Cube™ with hydrogen at one atmosphere pressure or above and at room temperature or elevated temperature. Other catalysts such as platinum oxide or those containing rhodium, platinum, or nickel can be used. Alternatively, the reduction can be carried out with metals such as iron or tin in acidic media (e.g., aqueous hydrochloric acid). Diazotization of compound 19, followed by a Sandmeyer reaction produces a key synthon 20. Diazonium salts can be prepared by reaction of primary amines with sodium nitrite in strong acids (e.g. aqueous hydrochloric acid and hydrobromic acid) or with alkyl nitrites such as t-butyl nitrite, isoamyl nitrite and the like in organic solvents. Subsequent displacement of diazonium ($N_2^+$) group with a nucleophile such as chloride, iodide, bromide or cyanide completes the process. While many Sandmeyer reactions are carried out under copper(I) catalysis, the Sandmeyer-type reactions with potassium iodide does not require the presence of catalyst. The amidation of benzoic acid 20 can be achieved using methods well known to one of ordinary skill in the art. For example, the transformation is preferably accomplished by converting the carboxylic acid to the corresponding acyl chloride by treating it with a chlorinating agent such as thionyl chloride at a temperature about 80° C. followed by treatment with a primary or secondary amine (21). Alternatively, benzamide (22) can be prepared by reaction of an activated ester with amines of diverse structure or their corresponding acid addition salts such as hydrochloride salts in the presence of an appropriate base, such as diisopropylethylamine or triethylamine and a coupling reagent, many examples of which are well known in peptide chemistry. The reaction is carried out in an inert solvent such as chlorinated hydrocarbon (e.g. dichloromethane) or N,N-dimethylformamide at room temperature. Transformation of the methyl phenyl ether 22 to hydroxyl-benzamide intermediate 23 can be achieved using methods well known to one of ordinary skill in the art. For example, transformation can be accomplished by reaction of benzamide 22 with boron tribromide at a temperature about −78° C. Alternatively, the methyl phenyl ether 22 can be demethylated by a reaction with sodium iodide and trimethylsilyl chloride in refluxing acetonitrile. Coupling reaction between phenol 23 and alkyl bromide intermediate 16 can be accomplished in refluxing acetone or a mixture of acetone and N,N-dimethylformamide at a temperature about 75° C. in the presence of a base such as potassium carbonate or cesium carbonate. The compounds of structure 27 can be prepared by hydrolyzing an ester of formula 24 and then carrying out a Suzuki reaction on intermediate 25. The ester hydrolysis can be conveniently effected by treating the compound 24 with several equivalents of an alkali metal hydroxide, such as sodium hydroxide, potassium hydroxide or lithium hydroxide, in a suitable solvent such as a mixture of alcohol and water or tetrahydrofuran and water. The reaction can be carried out at a temperature ranging from 0° C. to 70° C. In some cases a milder method can be employed for ester hydrolysis by using trimethyltin hydroxide in 1,2-dichloromethane at 70° C. (*Angew. Chem. Int. Ed.* 2005, 44, 1378-82). The Suzuki aryl-aryl coupling reaction is carried out between halide 25 and aryl boronic acids (26) to produce the compounds of formula 27. The conditions of this method are disclosed in many publications which have been reviewed by A. Suzuki in an article entitled "The Suzuki reaction with arylboron compounds in arene chemistry" in *Modern Arene Chemistry* 2002, 53-106. In carrying out this reaction any of the conditions conventional in a Suzuki reaction can be utilized. Generally Suzuki coupling reactions are carried out in the presence of a transition metal catalyst such as a palladium catalyst utilizing any conventional organic solvent for this reaction and a weak inorganic base. Among the preferred organic solvents are the polar aprotic solvents. Any conventional polar aprotic solvents can be utilized in preparing compounds of the invention. Suitable solvents are customary, especially higher-boiling solvents, e.g. dimethoxyethane. The weak inorganic base can be a carbonate or bicarbonate, such as potassium carbonate or cesium carbonate or phosphate such as potassium phosphate. The source of palladium can be palladium(0) complex (e.g. tetrakis(triphenylphosphine)palladium(0)) or a compound which can be reduced in situ to give palladium(0) (for example palladium acetate(II) or bis(triphenylphosphine)palladium(II) chloride or Pd(dppf)$Cl_2$), and the reaction can be carried out in the optional presence of a catalytic amount of phosphine ligand, for example tri-o-tolylphosphine or tri-tert-butylphosphine. The reaction is carried out at a temperature between room temperature and about 100° C., preferably about 90° C. if using conventional heating. The reaction can be also effected by microwave irradiation which is usually carried out at higher temperatures (for example 160° C.) but shorter time (20 min versus several hours for conventional heating).

Scheme 5: Method B

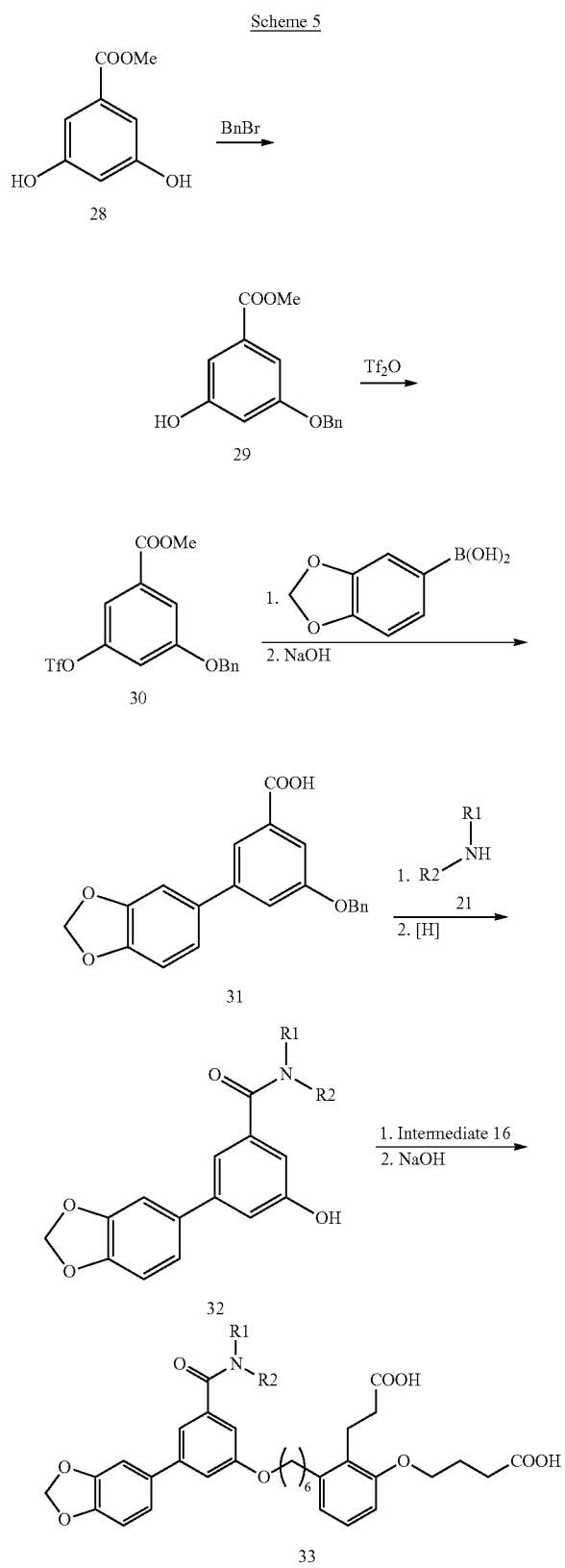

Commercially available 3,5-dihydroxy-benzoic acid methyl ester (28) can be alkylated with benzyl bromide (or any other substituted benzyl bromide) in refluxing acetone in the presence of a base such as potassium carbonate or cesium carbonate. Typically, the monobenzylated compound (29) is useful for this purpose while the reaction produces a mixture of monobenzylated and dibenzylated compounds; these compounds are readily separable on silica gel flash column chromatography, a purification well known to those skilled in the art. Alternatively, monobenzylated compound (29) can be produced in a two-step process starting from di-alkylation of 3,5-dihydroxy-benzoic acid methyl ester (28) with benzyl bromide to produce dibenzylether followed by selective monodebenzylation (using catalytical hydrogenation, preferably over 10% Pd/C in acetic acid). This method was described in literature in *Synthetic Communications*, 1995, 25, 2327-2335. Phenol 29 can be converted to aryl triflate 30 using methods well known to one of ordinary skill in the art. For example, transformation can be accomplished by reaction of phenol 29 and triflic anhydride in dichloromethane in the presence of pyridine at a temperature about 0° C. An alternative way of preparing aryl triflates is to use N-phenyltriflimide (described in *Tetrahedron Letters*, 1973, 14, 4607-4610). This reaction can also be effected by microwave irradiation (described in Organic Letters 2002, Vol. 2, No. 7, 1231-1233). Benzoic acid 31 can be prepared from the corresponding methyl benzoate 30 by Suzuki coupling reaction with boronic acids or boronic esters, followed by subsequent hydrolysis of ethyl ester function (general methods for Suzuki coupling reaction and ester hydrolysis are described in Method A). Amidation of intermediate 31 (general methods for amidation are described in Method A), followed by debenzylation leads to phenol 32. Debenzylation is effected by catalytic hydrogenation using hydrogen gas over palladium catalyst absorbed on carbon in solvent such as methanol, ethyl acetate or tetrahydrofuran. Other methods for removal of the benzyl group are described in "Protective Groups in Organic Synthesis" by T. Greene and P. Wuts, third edition, John Wiley & Sons, Inc. pp. 266-269. Coupling reaction between phenol 32 and alkyl bromide intermediate 16 can be accomplished in refluxing acetone or a mixture of acetone and N,N-dimethylformamide at a temperature about 75° C. in the presence of a base such as potassium carbonate or cesium carbonate. Subsequent hydrolysis of ester function yields the compounds of structure 33.

Scheme 6: Method C

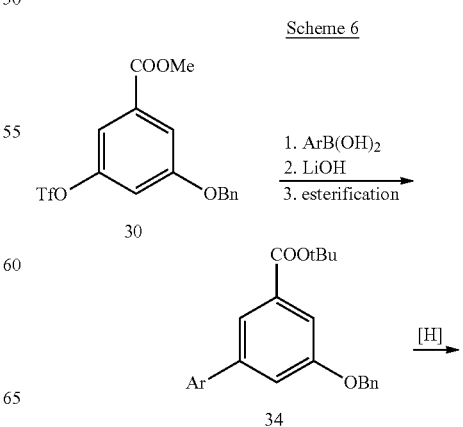

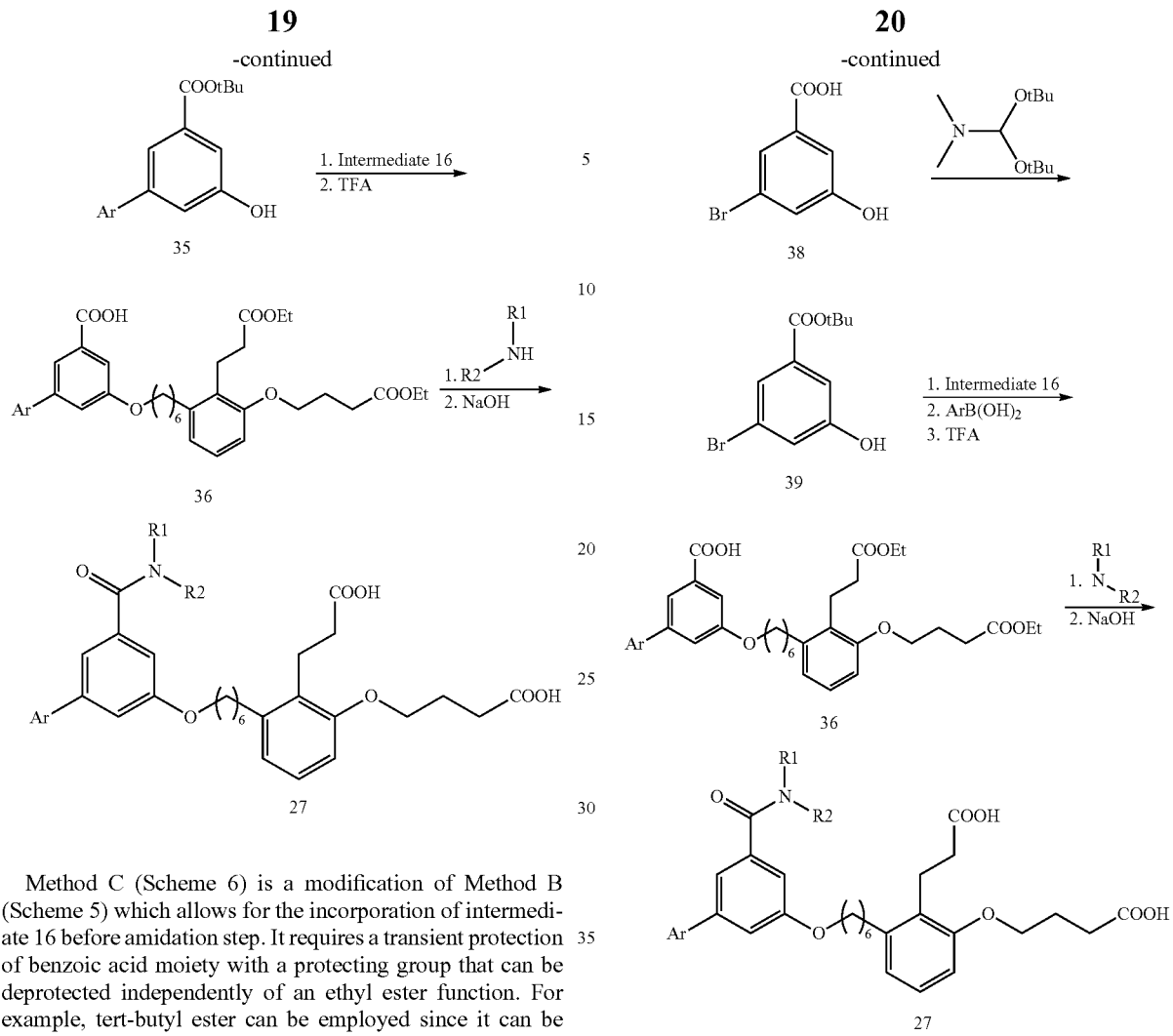

Method C (Scheme 6) is a modification of Method B (Scheme 5) which allows for the incorporation of intermediate 16 before amidation step. It requires a transient protection of benzoic acid moiety with a protecting group that can be deprotected independently of an ethyl ester function. For example, tert-butyl ester can be employed since it can be deprotected in acidic conditions without affecting the ethyl ester functionality. tert-Butyl esters can be prepared and cleaved using methods well known to one of ordinary skill in the art. For example, formation of tert-butyl esters can be accomplished by reaction of carboxylic acids and N,N-dimethylformamide di-tert-butyl acetal in toluene at a temperature about 85° C., while deprotection of tert-butyl esters can be effected by treatment with trifluoroacetic acid in dichloromethane at room temperature. Other methods for preparation as well as cleavage of tert-butyl esters are described in "Protective Groups in Organic Synthesis" by T. Greene and P. Wuts, third edition, John Wiley & Sons, Inc. pp. 404-408.

The usefulness of method D (Scheme 7) lies in a synthesis of benzoic acid 38 which is a synthetic equivalent of intermediate 30. Benzoic acid 38 can be prepared from commercially available 3-bromo-5-iodo-benzoic acid (37) by reacting it with aqueous sodium hydroxide in the presence of catalytical amount of cuprous oxide at a temperature about 100° C. (as described in *Organic Process Research & Development* 2002, 6, 591-596). All the remaining steps leading to preparation of compounds of formula 27 have been described so far in Methods A, B, and C.

Scheme 7: Method D

Scheme 8: Method E

Scheme 7

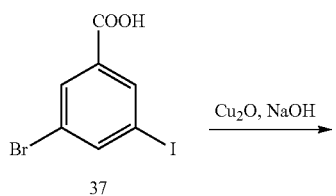

Scheme 8

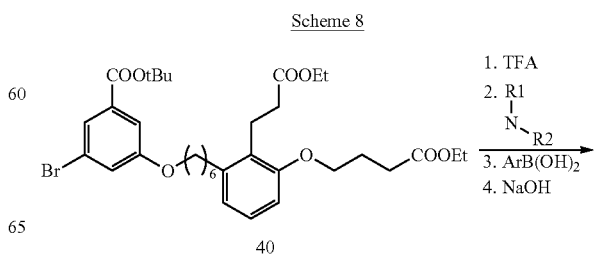

-continued

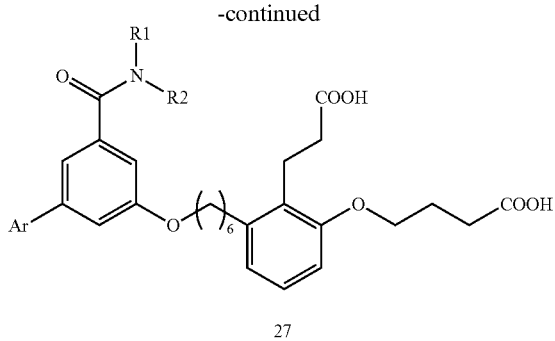

27

Method E (Scheme 8) is a modification of Method D (Scheme 7) with the reversal of two steps, namely, the Suzuki coupling reaction and amidation. In Method D, the Suzuki coupling reaction precedes the amidation reaction in the reaction sequence while in Method D amidation is performed before the Suzuki coupling reaction. All the remaining steps leading to preparation of compounds of formula 27 have been described so far in Methods A, B, C and D.

Scheme 9: Method F

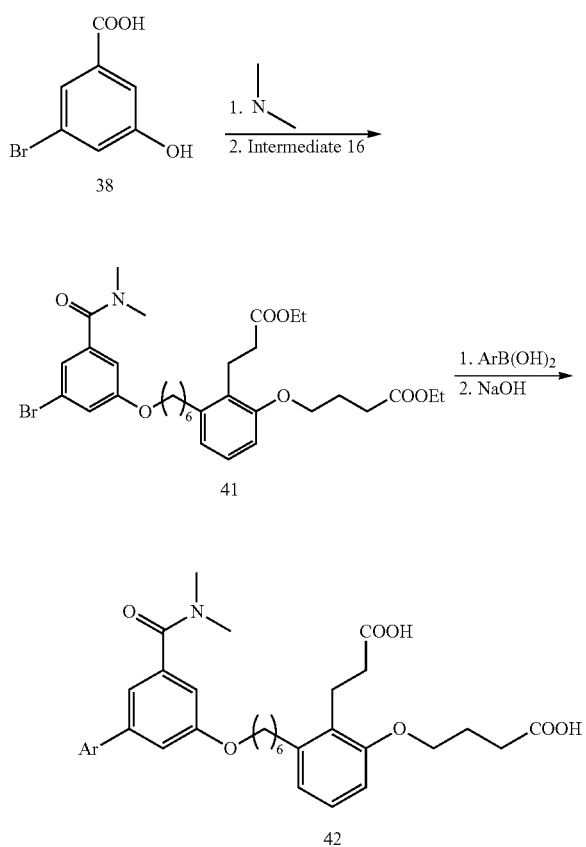

Method F (Scheme 9) is a modification of Method D (Scheme 7). The amide is formed directly from benzoic acid 38 without transient protection of benzoic acid functionality with tert-butyl ester. All the remaining steps leading to preparation of compounds of formula 42 have been described so far in Methods A, B, C and D.

Scheme 10a: Method G

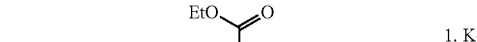

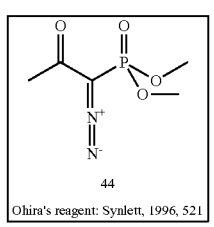

The synthetic route to alkyne intermediate 45 is shown in Scheme 10a. The conversion of the bromide 16 to aldehyde 43 can be accomplished using pyridine-N-oxide and sodium bicarbonate (*J. Org. Chem.* 1970, 35, 244). Other methods are also found in the literature to successfully convert an alkyl bromide to an aldehyde; use of AgBF$_4$-DMSO (*Synthesis* 2004, 271); trimethylamine-N-oxide-DMSO (*Tetrahedron Lett.*, 1990, 31, 4825); DMSO-KI-Na$_2$CO$_3$ (*Carbohydrate. Res.* 2001, 330, 295). Aldehyde 43 can then be transformed into an alkyne 45 using Ohira's reagent 44 (*Synth. Commun.*, 1989, 19, 561) and potassium carbonate. During the reaction, a transesterification may occur changing the ethyl ester to a methyl ester which can then be cleaved in the next step to generate the free diacid.

Scheme 10b: Method G

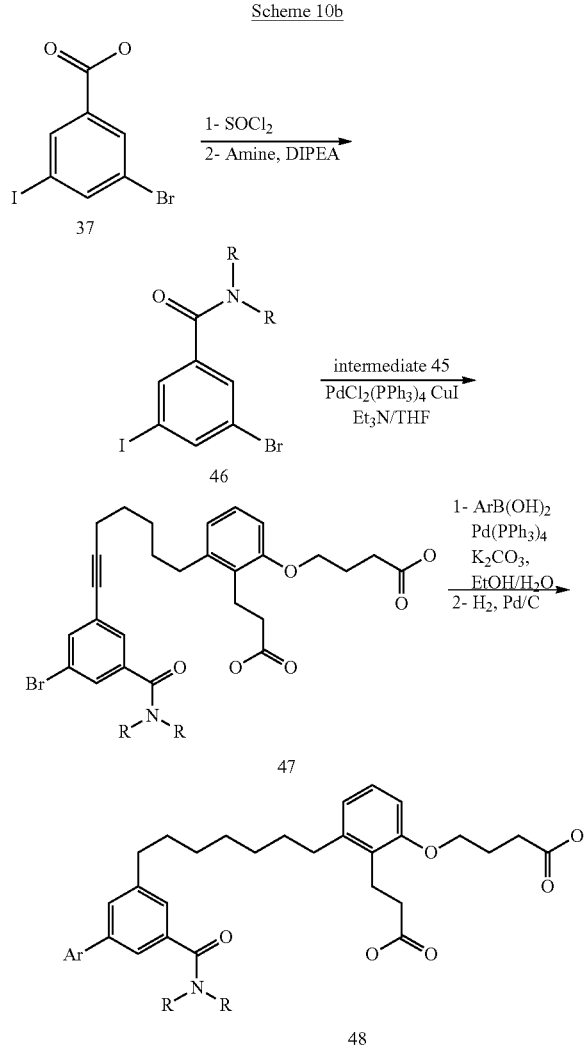

Benzamide 46 can be prepared from commercially available 3-bromo-5-iodo-benzoic acid 37 using methods well known to one of ordinary skill in the art, preferably by treatment with thionyl chloride to convert benzoic acid 37 to the corresponding benzoyl chloride, followed by the reaction with an appropriate amine. Using the Sonogashira reaction (*Chem. Rev.* 2007, 107, 874-922), selective mono-alkynylation of compound 46 could be achieved easily. It is well established that the general order of reactivity favors considerably aryl iodide over aryl bromide under the Sonogashira reaction conditions. The Sonogashira reaction is accomplished in the presence of polar groups such as amide and acid which demonstrate its wide compatibility to various functional groups. Intermediate 47 can be further derivatized with various aryl groups via a Suzuki coupling reaction and reduced to a saturated analog 48 using methods well known to one of ordinary skill in the art, preferably by catalytic hydrogenation with hydrogen gas over palladium catalyst absorbed on carbon in either Parr apparatus or an H-Cube™ with hydrogen at one atmosphere pressure or above and at room temperature or elevated temperature in solvents such as methanol or tetrahydrofuran.

Scheme 11

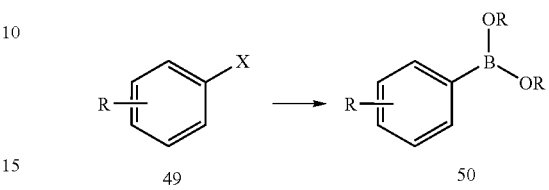

Substituted phenyl boronic acids (50, R=H) and boronic esters such as 4,4,5,5-tetramethyl-[1,3,2]dioxaborolane (50, R=—(C(CH$_3$)$_2$)$_2$—) useful in the preparation of compounds of this invention may be commercially available or they can be made by reactions that are well known in the field of organic synthesis. Aryl boronic acids and aryl boronic esters are formed by treatment of aryl halides (49) with an organometallic reagent such as n-butyl lithium followed by treatment with boron triisopropoxide or 4,4,4',4',5,5,5',5'-octamethyl-2,2'-bi-1,3,2-dioxaborolane followed by acidic work-up as is well known to those skilled in the art.

Commercially available boronic acids used in this procedure are listed below. The Available Chemicals Database (ACD) indicates the availability of greater than seven hundred commercially available aryl boronic acids. Some boronic acids useful for the preparation of compounds of the invention are listed below.

TABLE 1

| Commercially available boronic acids Boronic acid |
|---|
| 3-CHLORO-PHENYLBORONIC ACID |
| 3-CHLORO-5-METHYLPHENYLBORONIC ACID |
| 3-CHLORO-6-METHOXYPHENYLBORONIC ACID |
| 3-CHLORO-4-FLUOROPHENYLBORONIC ACID |
| 3-CHLORO-4-METHYLPHENYLBORONIC ACID |
| 3-CHLORO-2-METHYLPHENYLBORONIC ACID |
| 4-CHLORO-3-METHYLPHENYLBORONIC ACID |
| 2,4-DI-CHLOROPHENYLBORONIC ACID |
| 4-CHLORO-2-METHYLPHENYLBORONIC ACID |
| 4-CHLORO-2-METHOXYLPHENYLBORONIC ACID |
| 4-CHLORO-2-ETHOXYLPHENYLBORONIC ACID |
| 4-CHLORO-3-AMINOPHENYLBORONIC ACID |
| 3-ISOPROPYLPHENYLBORONIC ACID |
| THIOPHENE-3-BORONIC ACID |
| 2-METHYLPHENYLBORONIC ACID |
| 3-METHYLPHENYLBORONIC ACID |
| (2-HYDROXYMETHYLPHENYL)BORONIC ACID DEHYDRATE |
| (3-HYDROXYMETHYLPHENYL)BORONIC ACID DEHYDRATE |
| 4-HYDROXYPHENYL)BORONIC ACID DEHYDRATE |
| 2-METHOXYPHENYLBORONIC ACID |
| 3-METHOXYPHENYLBORONIC ACID |
| 2-TRIFLUOROMETHOXYPHENYLBORONIC ACID |
| 3-TRIFLUOROMETHOXYPHENYLBORONIC ACID |
| 6-FLUORO-2-METHOXYPHENYLBORONIC ACID |
| 2-FLUORO-3-METHOXYPHENYLBORONIC ACID |
| 5-FLUORO-2-METHOXYPHENYLBORONIC ACID |
| 3,4-DIMETHOXYPHENYLBORONIC ACID |
| 5-BENZO[1,3]DIOXOLEBORONIC ACID |
| 2,3,4-TRIMETHOXYPHENYLBORONIC ACID |
| 1H-INDOLE-5-BORONIC ACID |
| QUINOLINE-8-BORONIC ACID |
| 4-PYRIDYL-BORONIC ACID |

TABLE 2

These boronic acids are also available from other suppliers that may not necessarily be listed in the ACD.

| | | |
|---|---|---|
| 3-Fluoro-6-(4,4,5,5-tetramethyl-[1,3,2]dioxaborolan-2-yl)pyridine | ATLANTIC SCIENTIFIC CO., INC., JERSEY CITY, NJ, | 791819-04-0 |
| Quinoline-2-boronic acid | LANCASTER | 745784-12-7 |
| 3-Chloro-6-(4,4,5,5-tetramethyl-[1,3,2]dioxaborolan-2-yl)pyridine | ATLANTIC SCIENTIFIC CO., INC., JERSEY CITY, NJ, | 652148-93-1 |
| 6-Chloropyridine-2-boronic acid pinacol ester | INTERCHIM, MONTLUCON, FRANCE | 652148-92-0 |
| Boronic acid, (2-methyl-4-pyrimidinyl)- | CHEMSTEP, TALENCE, FRANCE | 647853-31-4 |
| Boronic acid, (3-methoxy-2-pyridinyl)- | CHEMSTEP, TALENCE, FRANCE | 500707-34-6 |
| Boronic acid, (6-methoxy-2-pyridinyl)- | CHEMSTEP, TALENCE, FRANCE | 372963-51-4 |
| Boronic acid, (6-methyl-2-pyridinyl)- | CHEMSTEP, TALENCE, FRANCE | 372963-50-3 |
| Boronic acid, (5-methyl-2-pyridinyl)- | CHEMSTEP, TALENCE, FRANCE | 372963-49-0 |
| Boronic acid, (4-methyl-2-pyridinyl)- | CHEMSTEP, TALENCE, FRANCE | 372963-48-9 |
| Boronic acid, 2-pyridinyl- | CHEMSTEP, TALENCE, FRANCE | 197958-29-5 |

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day.

The invention will now be further described in the Examples below, which are intended as an illustration only and do not limit the scope of the invention.

EXAMPLES

Reagents were purchased from Aldrich, Sigma, Maybridge, Advanced ChemTech, and Lancaster or other suppliers as indicated below and used without further purification. Reactions using microwave irradiation for heating were conducted using either a Personal Chemistry Emrys Optimizer System or a CEM Discovery System. The purification of multi-milligram to multi-gram scale was conducted by methods known to those skilled in the art such as elution of silica gel flash column; preparative flash column purifications were also effected in some cases by use of disposal pre-packed multigram silica gel columns (RediSep) eluted with a CombiFlash system. Biotage™ and ISCO™ are also flash column instruments that may have been used in this invention for purification of intermediates.

For the purpose of judging compound identity and purity, LC/MS (liquid chromatography/mass spectroscopy) spectra were recorded using the following system. For measurement of mass spectra, the system consisted of a Micromass Platform II spectrometer: ES Ionization in positive mode (mass range: 150-1200 amu). The simultaneous chromatographic separation was achieved with the following HPLC system: ES Industries Chromegabond WR C-18 3u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute. In some cases, ammonium acetate at 20 millimolar concentration was used as a modifier for effective ionization during preparative HPLC. In such cases, the ammonium salt was isolated.

For some separations, the super critical fluid chromatography was also useful. Super critical fluid chromatography separations were performed using a Mettler-Toledo Minigram system with the following typical conditions: 100 bar, 30° C., 2.0 mL/min eluting a 12 mm AD column with 40% MeOH in super critical fluid $CO_2$. In the case of analytes with basic amino groups, 0.2% isopropyl amine was added to the methanol modifier.

Many compounds of Formula 1 were also purified by reversed phased HPLC, using methods well known to those skilled in the art. In some cases, preparative HPLC purification was conducted using PE Sciex 150 EX Mass Spec controlling a Gilson 215 collector attached to a Shimadzu preparative HPLC system and a Leap autoinjector. Compounds were collected from the elution stream using LC/MS detection in the positive ion detection: The elution of compounds from C-18 columns (2.0×10 cm eluting at 20 ml/min) was effected using appropriate linear gradation mode over 10 minutes of Solvent (A) 0.05% TFA/H2O and Solvent (B) 0.035% TFA/acetonitrile. For injection on to HPLC systems, the crude samples were dissolved in mixtures of methanol, acetonitrile and DMSO H-Cube™ (produced by Thales Nanotechnology) is a continuous-flow hydrogenation reactor equipped with in situ hydrogen generation and a disposable catalyst cartridge Cat-Cart™. The reaction mixture can be heated and pressurized up to 100° C. and 100 bar (1450 psi) respectively. Reaction scale can be varied from 10 mg to 100 g.

Compounds were characterized either by $^1$H-NMR using a Varian Inova 400 MHz NMR Spectrometer or a Varian Mercury 300 MHz NMR Spectrometer as well as by high resolution mass spectrometry using a Bruker Apex-II high-resolution 4.7 T FT-Mass Spectrometer.

LIST OF ABBREVIATIONS

DCE 1,2-dichloroethane
DCM dichloromethane
DIPEA diisopropylethylamine
DMF N,N-dimethylformamide
DMSO dimethylsulfoxide
EtOAc ethyl acetate
EtOH ethyl alcohol
FCC flash column chromatography
HPLC high pressure chromatography
HRMS high resolution mass spectra
LRMS low resolution mass spectra
LC liquid chromatography
MeOH methyl alcohol
MW microwave
NIS N-iodosuccinimide
NMP 1-methyl-2-pyrrolidinone
PdCl$_2$(dppf) [1,1'-Bis(diphenylphosphino)ferrocene]dichloropalladium(II)
PyBroP bromo-tris-pyrrolidino-phosphonium hexafluorophosphate
rt room temperature
TBDMS tert-butyl-dimethylsilyl
TBTU 2-(1H-benzotriazole-1-yl)-1,1,3,3-tetramethyluronium tetrafluoroborate
TEA triethylamine
TEMPO 2,2,6,6-tetramethylpiperidine-1-oxyl
TFA trifluoroacetic acid
THF tetrahydrofuran I. Preparation of Preferred Intermediates Preparation of 4-[3-(6-bromo-hexyl)-2-(2-ethoxycarbonyl-ethyl)-phenoxy]-butyric acid ethyl ester 1) Preparation of 4-(2,3-dimethyl-phenoxy)-butyric acid ethyl ester

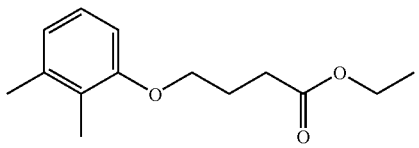

To a solution of 2,3-dimethylphenol (25 g, 204 mmol) in DMSO (205 mL) was added 4-bromo-butyric acid ethyl ester (40.96 g, 210 mmol) and lithium hydride (2.0 g, 250 mmol) at room temperature. The resulting light brown solution was stirred for 2 days. Then, the reaction mixture was cooled to 0° C. and water (200 mL) was added slowly. The organic compound was extracted into hexanes (2×200 mL). The combined organic extracts were washed with brine solution (150 mL) and the organic solution was dried over anhydrous magnesium sulfate. Filtration of the drying agent and the removal of the solvent gave light brown oil. The crude mixture was purified by using a Biotage™ (40 L) column chromatography eluting with 5% ethyl acetate in hexanes to isolate 4-(2,3-dimethyl-phenoxy)-butyric acid ethyl ester (45.32 g, 94%) as a colorless oil: ES(+)-HRMS m/e calculated for $C_{14}H_{20}O_3$ (M+)$^+$ 236.1412, found 236.1419.

2) Preparation of 4-(2-formyl-3-methyl-phenoxy)-butyric acid ethyl ester

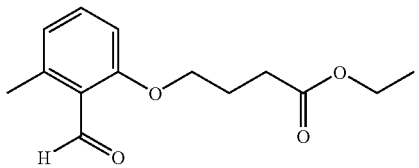

A mixture of copper(II)sulfate pentahydrate (21.98 g, 88.06 mmol) and potassium persulfate (71.42 g, 264 mmol) in water (396 mL) was heated to 63-65° C. to obtain a blue colored solution. Then, a solution of 4-(2,3-dimethyl-phenoxy)-butyric acid ethyl ester (20.81 g, 88.06 mmol) in acetonitrile (220 mL) was added at the above temperature. The resulting light green solution was refluxed for 40 minutes. Then, the reaction mixture was cooled to ~5° C. in order to precipitate most of the inorganic solids. The resulting solids were collected by filtration and the solid cake was washed with dichloromethane (1.0 L). The two layers of filtrate were separated and the aqueous layer was extracted with dichloromethane (200 mL). The combined organic extracts were washed with brine solution (150 mL) and the organic solution was dried over anhydrous magnesium sulfate. Filtration of the drying agent and the removal of the solvent gave a brown oil. The crude mixture was purified by using a Biotage™ (40 L)

column chromatography eluting with 5-10% ethyl acetate in hexanes to obtain 4-(2-formyl-3-methyl-phenoxy)-butyric acid ethyl ester (45.32 g, 94%) as a colorless oil: EI(+)-HRMS m/e calculated for $C_{14}H_{18}O_4$ (M+)$^+$ 250.1205, found 250.1202.

3) Preparation of 4-[2-((E)-2-ethoxycarbonyl-vinyl)-3-methyl-phenoxy]-butyric acid ethyl ester

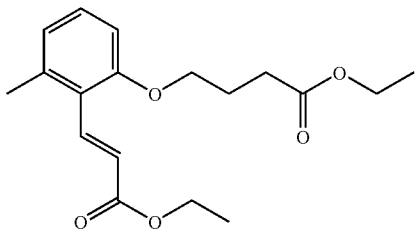

Sodium metal spheres (1.6 g, 69.6 mmol) were added to ethanol (100 mL) with stirring at room temperature under nitrogen atmosphere over 15 min. An exothermic reaction occurred and the mixture was stirred for another 15 min to form sodium ethoxide. After cooling to room temperature, triethylphosphonoacetate (14.7 mL, 73.4 mmol) and 4-(2-formyl-3-methyl-phenoxy)-butyric acid ethyl ester (13.25 g, 52.9 mmol) were added sequentially. During the addition of 4-(2-formyl-3-methyl-phenoxy)-butyric acid ethyl ester, the color of the solution turned brown and the temperature increased to ~55° C. The resulting brown solution was stirred for 2 days at room temperature. Then, the reaction mixture was diluted with water (150 mL) and stirred for 1 h. Then, the organic compound was extracted into hexanes (3×100 mL). The combined organic extracts were washed with brine solution (150 mL) and the organic solution was dried over anhydrous magnesium sulfate. Filtration of the drying agent and the removal of the solvent gave a light yellow oil. The crude oil was dissolved in hexanes (~50 mL) and treated with charcoal and heated gently with a heat gun. After cooling to room temperature, the charcoal was filtered-off and the filtrate was removed under vacuum to give 4-[2-((E)-2-ethoxycarbonyl-vinyl)-3-methyl-phenoxy]-butyric acid ethyl ester (13.25 g, 78%) as colorless oil: EI(+)-HRMS m/e calculated for $C_{18}H_{24}O_5$ (M+)$^+$ 320.1624, found 320.1626.

4) Preparation of 4-[3-bromomethyl-2-((E)-2-ethoxycarbonyl-vinyl)-phenoxy]-butyric acid ethyl ester

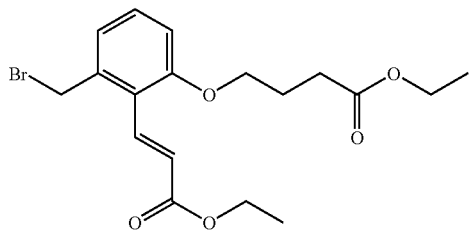

To a solution of 4-[2-((E)-2-ethoxycarbonyl-vinyl)-3-methyl-phenoxy]-butyric acid ethyl ester (8.0 g, 25.0 mmol) in chlorobenzene (190 mL) were added N-bromosuccinimide (6.67 g, 37.5 mmol) and 2,2'-azobisisobutyronitrile (AIBN) (591 mg, 3.6 mmol) at room temperature. Then, the solution was heated to 85° C. and stirred for 1 h. Then, the reaction mixture was cooled to room temperature and diluted with water (100 mL). Then, the organic compound was extracted into hexanes (3×100 mL). The combined organic extracts were washed with brine solution (150 mL) and the organic solution was dried over anhydrous magnesium sulfate. Filtration of the drying agent and the removal of the solvent gave a crude oil. The crude oil was purified by using a Biotage (40 L) column eluting with 15-25% ethyl acetate in hexanes to isolate 4-[3-bromomethyl-2-((E)-2-ethoxycarbonyl-vinyl)-phenoxy]-butyric acid ethyl ester (7.11 g, 71%) as a low melting solid: ES(+)-HRMS m/e calculated for $C_{18}H_{23}BrO_5$ (M+Na)$^+$ 421.0621, found 421.0621.

5) Preparation of 5-(tert-butyl-dimethyl-silanyloxy)-pentanal

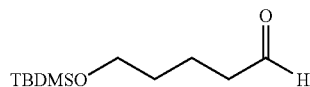

To a solution of 5-(tert-butyl-dimethyl-silanyloxy)-pentanol (16.8 mmol, 3.66 g) in dichloromethane (30 mL) were added water (5.6 mL), potassium bromide (1.7 mmol, 202 mg), n-tetrabutylammonium hydrogensulfate (0.84 mmol, 290 mg), and TEMPO (30 mg) at room temperature. The resulting light brown solution was cooled to ~5° C. and a solution of sodium hypochlorite (19.3 mmol, 30 mL, 5%) was added dropwise at this temperature. After addition of half of the sodium hypochlorite solution, solid potassium carbonate (300 mg) was added to maintain the reaction mixture basic. Then, the remaining sodium hypochlorite solution was added at 5-10° C. By this point, a precipitate had formed and the reaction mixture was stirred for another 1 h at ~10-15° C. Then, water (100 mL) was added and the resulting solution was extracted into diethyl ether (2×100 mL). The combined organic extracts were washed with brine solution (150 mL) and the organic layer was dried over anhydrous magnesium sulfate. Filtration of the drying agent and the removal of the solvent gave 5-(tert-butyl-dimethyl-silanyloxy)-pentanal (3.32 g, 91%) as a light brown oil: ES(+)-HRMS m/e calculated for $C_{11}H_{24}O_2Si$ (M+H)$^+$ 217.1619, found 217.1619.

6) Preparation of 4-[3-[6-(tert-butyl-dimethyl-silanyloxy)-hex-1-enyl]-2-((E)-2-ethoxycarbonyl-vinyl)-phenoxy]-butyric acid ethyl ester

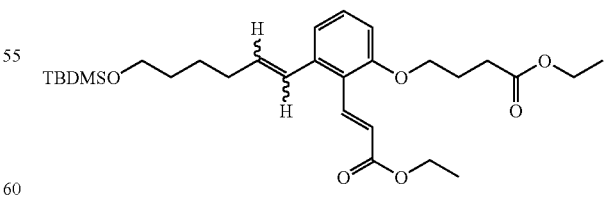

A solution of 4-[3-bromomethyl-2-((E)-2-ethoxycarbonyl-vinyl)-phenoxy]-butyric acid ethyl ester (2.0 mmol, 798 mg) and triphenylphosphine (2.2 mmol, 577 mg) in acetonitrile (12 mL) was heated to reflux for 1 h under nitrogen atmosphere. Then, it was cooled to room temperature and a solution of 5-(tert-butyl-dimethyl-silanyloxy)-pentanal (2.8 mmol, 606 mg) in 1,2-epoxybutane (22 mL) was added at room temperature and the mixture was again heated to reflux for 15 h. During this period, the mixture first turned to a brick red color and at the end of the reaction it had become a pale yellow solution. Then, the reaction mixture was cooled to room temperature and the solvent was removed under vacuum. The residue was dissolved in a solution of ethyl acetate and hexanes (1:3, 150 mL) and the resulting cloudy solution was washed with a mixture of methanol and water (2:1, 225 mL). The aqueous layer was extracted one more time with ethyl acetate and hexanes (1:3, 50 mL). The combined organic extracts were washed with brine solution (150 mL) and the organic solution was dried over anhydrous magnesium sulfate. Filtration of the drying agent and the removal of the solvent gave light brown oil. The crude mixture was purified by using a Biotage™ (40 L) column chromatograph eluting with 5 and 15% ethyl acetate in hexanes to obtain the desired 4-[3-[6-(tert-butyl-dimethyl-silanyloxy)-hex-1-enyl]-2-((E)-2-ethoxycarbonyl-vinyl)-phenoxy]-butyric acid ethyl ester (760 mg, 74%) as a colorless oil: ES(+)-HRMS m/e calculated for $C_{29}H_{46}O_6Si$ $(M+Na)^+$ 541.2956, found 541.2953.

7) Preparation of 4-[3-[6-(tert-butyl-dimethyl-silanyloxy)-hexyl]-2-(2-ethoxycarbonyl-ethyl)-phenoxy]-butyric acid ethyl ester

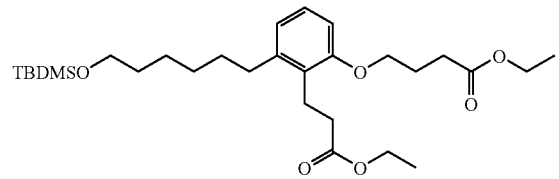

To a solution of 4-[3-[6-(tert-butyl-dimethyl-silanyloxy)-hex-1-enyl]-2-((E)-2-ethoxycarbonyl-vinyl)-phenoxy]-butyric acid ethyl ester (0.977 mmol, 507 mg) in ethyl acetate (10 mL) was added 10% palladium on carbon (350 mg) at room temperature. The resulting black mixture was stirred in the presence of atmospheric hydrogen gas in a balloon for 36 h at room temperature. Then, the catalyst was removed by filtration using a filter paper and the residue was washed with hot ethyl acetate (~60 mL). The filtrate was concentrated in vacuo and the resulting residue was dried under high vacuum to obtain 4-[3-[6-(tert-butyl-dimethyl-silanyloxy)-hexyl]-2-(2-ethoxycarbonyl-ethyl)-phenoxy]-butyric acid ethyl ester (438 mg, 86%) as a colorless oil: ES(+)-HRMS m/e calculated for $C_{29}H_{50}O_6Si$ $(M+Na)^+$ 545.3269, found 545.3267.

8) Preparation of 4-[2-(2-ethoxycarbonyl-ethyl)-3-(6-hydroxy-hexyl)-phenoxy]-butyric acid ethyl ester

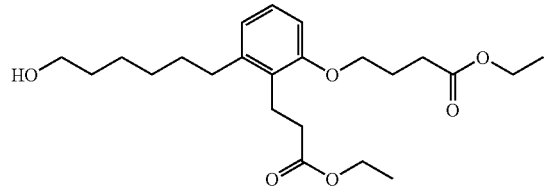

To a solution of 4-[3-[6-(tert-butyl-dimethyl-silanyloxy)-hexyl]-2-(2-ethoxycarbonyl-ethyl)-phenoxy]-butyric acid ethyl ester (0.837 mmol, 438 mg) in THF (12 mL) was added a solution of n-tetrabutyl ammonium fluoride (1.25 mmol, 1.25 mL, 1.0M) in THF at 0° C. Then, the resulting colorless solution was allowed to warm to room temperature in 2 h and the mixture was stirred for another 2 h at room temperature before being diluted with water (~50 mL). The organic compound was extracted into ethyl acetate (2×50 mL) and the combined extracts were washed with brine solution (100 mL). The organic solution was dried over anhydrous magnesium sulfate and the filtrate was removed under vacuum after filtration of the drying agent. The crude residue was dried further under high vacuum and the desired 4-[2-(2-ethoxycarbonyl-ethyl)-3-(6-hydroxy-hexyl)-phenoxy]-butyric acid ethyl ester (342 mg, 99%) was isolated as a colorless oil: ES(+)-HRMS m/e calculated for $C_{23}H_{36}O_6$ $(M+Na)^+$ 431.2404, found 431.2404.

9) Preparation of 4-[3-(6-bromo-hexyl)-2-(2-ethoxycarbonyl-ethyl)-phenoxy]-butyric acid ethyl ester

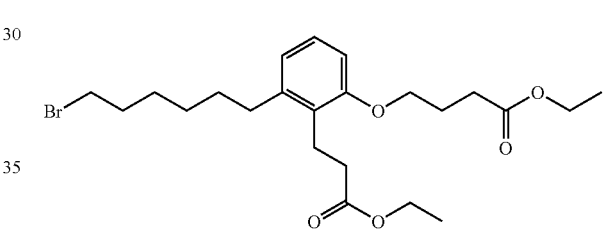

To a solution of 4-[2-(2-ethoxycarbonyl-ethyl)-3-(6-hydroxy-hexyl)-phenoxy]-butyric acid ethyl ester (0.85 mmol, 349 mg) and carbon tetrabromide (1.26 mmol, 423 mg) in dichloromethane (10 mL) was added triphenylphosphine (1.07 mmol, 281 mg) at −0° C. The resulting colorless solution was stirred for 3 h at 5-10° C. Then, the solvent was removed under vacuum and the crude was tried to dissolve in a mixture of ethyl acetate and hexanes (1:3, 50 mL). As a result, a cloudy solution containing some precipitate was formed and the cloudy solution was transferred into a separatory funnel and was washed with a mixture of methanol and water (2:1, 150 mL). The aqueous layer was extracted one more time with ethyl acetate and hexanes (1:3, 50 mL). The combined organic extracts were washed with brine solution (100 mL) and the organic solution was dried over anhydrous magnesium sulfate. Filtration of the drying agent and the removal of the solvent gave a colorless oil which was purified by using a Biotage™ (40M) column chromatography eluting with 10% ethyl acetate in hexanes to obtain the desired 4-[3-(6-bromo-hexyl)-2-(2-ethoxycarbonyl-ethyl)-phenoxy]-butyric acid ethyl ester (350 mg, 87.5%) as a colorless oil: ES(+)-HRMS m/e calculated for $C_{23}H_{35}BrO_5$ $(M+Na)^+$ 493.1560, found 493.1560.

II. Preparation of Preferred Compounds

Method A

Step 1: 3-Methoxy-5-nitrobenzoic acid

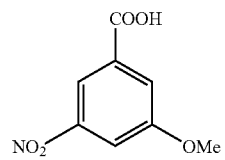

3-Methoxy-5-nitrobenzoic acid was prepared from commercially available 3,5-dinitrobenzoic acid according to a literature procedure (*Aust. J. Chem.* 1981, 34, 1319-24)

HRMS calcd for $C_8H_7NO_5$ $M^+$ 197.0324, observed 197.0325

Step 2: 3-Amino-5-methoxybenzoic acid

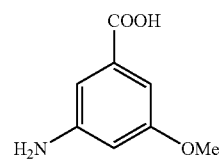

3-Methoxy-5-nitrobenzoic acid (510 mg) was dissolved in 5 ml of ethanol and 10% Pd(C) (50 mg) was added. The resulting suspension was stirred under a hydrogen-filled balloon for 2 hours. Then the reaction mixture was filtered and concentrated to dryness. Isolated dark brown solid (480 mg) was used without further purification in the next step.

LRMS calcd for $C_8H_9NO_3$ $[M+H]^+$ 168.1, observed 168.2

Step 3: 3-Iodo-5-methoxybenzoic acid

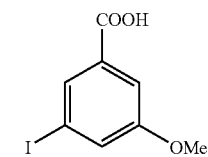

3-Amino-5-methoxybenzoic acid (3.1 g) was suspended in 10 mL of water, cooled to 0° C. and 10 mL of concentrated hydrochloric acid were added, followed by a dropwise addition of a cooled solution of sodium nitrite (2.3 g) in 15 mL water. The resulting solution was stirred for 15 minutes and then a solution of KI (6.1 g) in 10 mL of water was added dropwise. After addition was completed, the reaction mixture was heated to reflux until the production of purple vapor ceased. Then it was diluted with ethyl acetate, washed with 2% sodium bisulfite solution and brine and the organic extracts were filtered through a silica pad. The filtrate was extracted with aqueous bicarbonate solution. The aqueous extracts were washed with ethyl acetate and then acidified with 3N hydrochloric acid. The title product precipitated and was collected by filtration (3.4 g, 60% yield).

HRMS calcd for $C_8H_7IO_3$ $M^+$ 277.9440, observed 277.9439

Step 4

N-Benzyl-3-iodo-5-methoxy-benzamide

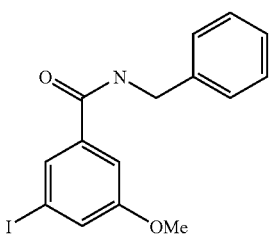

3-Iodo-5-methoxybenzoic acid (4.0 g) was refluxed in thionyl chloride (15 mL) for 2.5 h. Then the excess of thionyl chloride was removed under reduced pressure and the oily residue was taken up in methylene chloride (50 mL) and cooled to 0° C. A solution of benzylamine (6.4 mL) in methylene chloride (20 mL) was added dropwise. After 2 h the reaction mixture was diluted with ethyl acetate and washed with water, 1N hydrochloric acid, saturated bicarbonate solution and brine. The organic extract was dried over anhydrous sodium sulfate, concentrated and purified on a silica gel column using ethyl acetate and hexanes to yield 4.7 g of yellow oil (90% yield).

HRMS calcd for $C_{15}H_{14}INO_2$ $[M+H]^+$ 368.0142, observed 368.0139

(3-Iodo-5-methoxy-phenyl)-(4-methyl-piperazin-1-yl)-methanone

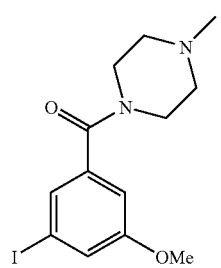

The title compound was prepared by the same method as N-benzyl-3-iodo-5-methoxy-benzamide. 4-Methylpiperazine was used instead of benzylamine. Starting with 3.1 g of 3-iodo-5-methoxybenzoic acid, 3.2 g (80% yield) of the title compound was obtained.

HRMS calcd for $C_{13}H_{17}IN_2O_2$ $[M+H]^+$ 316.0408, observed 316.0403

Step 5

N-Benzyl-3-hydroxy-5-iodo-benzamide

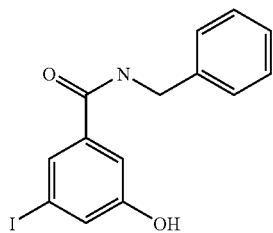

A solution of N-benzyl-3-iodo-5-methoxy-benzamide (4.7 g) in anhydrous dichloromethane (100 mL) was cooled to −78° C. in dry ice/acetone bath under flow of argon and a BBr$_3$ solution (38.4 mL of 1 M solution in dichloromethane) was added dropwise. After the addition was completed, the reaction mixture was stirred at room temperature overnight. The reaction mixture was cooled in an ice bath and then quenched by a dropwise addition of methanol. Then it was diluted with ethyl acetate, washed with water and brine, dried over anhydrous sodium sulfate and concentrated to remove the solvents. The title compound was obtained by trituration with diethyl ether and hexanes (4.1 g, 90% yield).

HRMS calcd for C$_{14}$H$_{12}$INO$_2$ [M+H]$^+$ 353.9986, observed 353.9982

3-Hydroxy-5-iodo-phenyl)-(4-methyl-piperazin-1-yl)-methanone

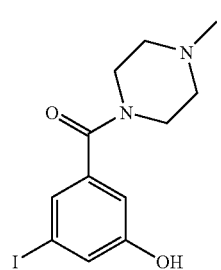

The title compound was prepared by the same method as N-benzyl-3-hydroxy-5-iodo-benzamide. Starting with 3.1 g of 3-iodo-5-methoxybenzoic acid, 2.1 g (60% yield) of the title compound was obtained.

HRMS calcd for C$_{12}$H$_{15}$IN$_2$O$_2$ [M+H]$^+$ 347.0251, observed 347.0249

Step 6

4-[3-[6-(3-Benzylcarbamoyl-5-iodo-phenoxy)-hexyl]-2-(2-ethoxycarbonyl-ethyl)-phenoxy]-butyric acid ethyl ester

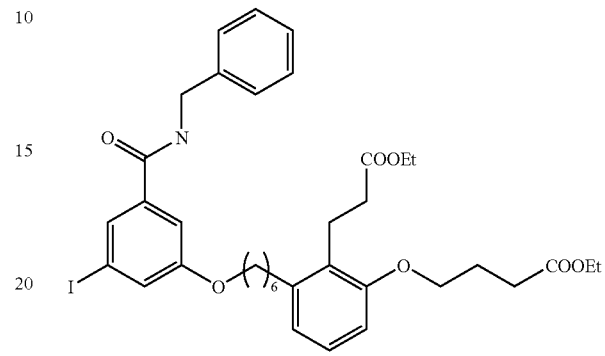

To a solution of N-benzyl-3-hydroxy-5-iodo-benzamide (4.1 g) in a mixture of acetone and DMF (2:1, 100 mL) were added potassium carbonate (16.0 g) and 4-[3-(6-bromo-hexyl)-2-(2-ethoxycarbonyl-ethyl)-phenoxy]-butyric acid ethyl ester (6.0 g). The resulting mixture was stirred at 75° C. for 2 days. Then the insoluble material was filtered out and the filtrate was diluted with ethyl acetate and washed with water and brine. The organic extract was dried over anhydrous sodium sulfate, concentrated and purified on a silica gel column using ethyl acetate and hexanes to yield 8.7 g of yellow oil (100% yield).

HRMS calcd for C$_{37}$H$_{46}$INO$_7$ [M+H]$^+$ 744.2392, observed 744.2380

4-(2-(2-Ethoxycarbonyl-ethyl)-3-{6-[3-iodo-5-(4-methyl-piperazine-1-carbonyl)-phenoxy]-hexyl}-phenoxy)-butyric acid ethyl ester

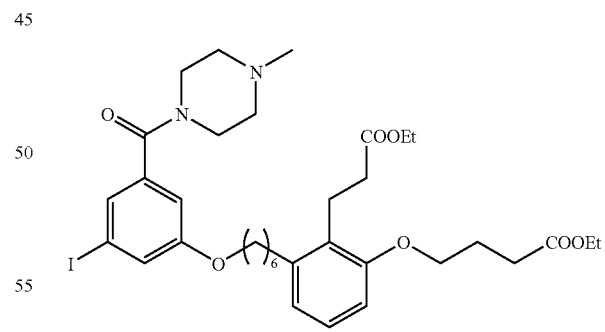

The title compound was prepared by the same method as 4-[3-[6-(3-benzylcarbamoyl-5-iodo-phenoxy)-hexyl]-2-(2-ethoxycarbonyl-ethyl)-phenoxy]-butyric acid ethyl ester.

Starting with 2.1 g of 3-hydroxy-5-iodo-phenyl)-(4-methyl-piperazin-1-yl)-methanone, 4.1 g (92% yield) of the title compound was obtained.

LRMS calcd for C$_{35}$H$_{49}$IN$_2$O$_7$ [M+H]$^+$ 737.3, observed 737.3

37

Step 7

4-[3-[6-(3-Benzylcarbamoyl-5-iodo-phenoxy)-hexyl]-2-(2-carboxy-ethyl)-phenoxy]-butyric acid

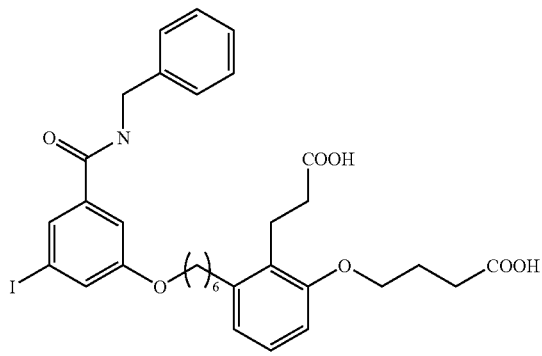

4-[3-[6-(3-Benzylcarbamoyl-5-iodo-phenoxy)-hexyl]-2-(2-ethoxycarbonyl-ethyl)-phenoxy]-butyric acid ethyl ester (8.7 g) was dissolved in THF (30 mL) and 2 M NaOH was added (30 mL). The resulting heterogeneous mixture was stirred vigorously at 55° C. for 4 h. Then it was acidified with 3 N HCl and extracted into diethyl ether. Etherate extract was washed with brine and dried over anhydrous sodium sulfate. The solvent was removed under reduced pressure to produce 8.1 g (100% yield) of colorless oil which solidified upon standing.

HRMS calcd for $C_{33}H_{38}INO_7$ [M+H]$^+$ 688.1766, observed 688.1759

4-(2-(2-Carboxy-ethyl)-3-{6-[3-iodo-5-(4-methyl-piperazine-1-carbonyl)-phenoxy]-hexyl}-phenoxy)-butyric acid

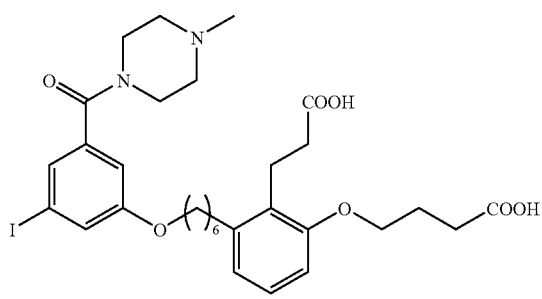

The title compound was prepared by the same method as 4-[3-[6-(3-benzylcarbamoyl-5-iodo-phenoxy)-hexyl]-2-(2-carboxy-ethyl)-phenoxy]-butyric acid.

Starting with 4.1 g of 4-(2-(2-ethoxycarbonyl-ethyl)-3-{6-[3-iodo-5-(4-methyl-piperazine-1-carbonyl)-phenoxy]-hexyl}-phenoxy)-butyric acid ethyl ester, 2.0 g (55% yield) of the title compound was obtained.

HRMS calcd for $C_{31}H_{41}IN_2O_7$ [M+H]$^+$ 681.2031, observed 681.2030

38

Example 1

4-[3-[6-(5-Benzylcarbamoyl-4'-methoxy-biphenyl-3-yloxy)-hexyl]-2-(2-carboxy-ethyl)-phenoxy]-butyric acid

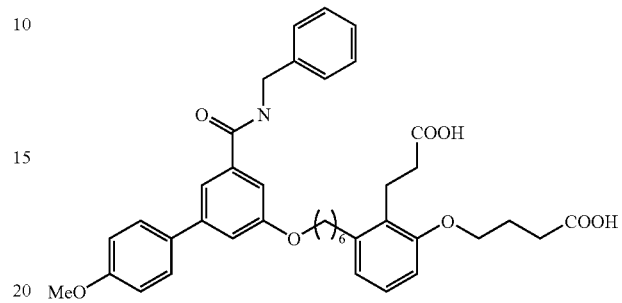

General Procedure:

4-[3-[6-(3-Benzylcarbamoyl-5-iodo-phenoxy)-hexyl]-2-(2-carboxy-ethyl)-phenoxy]-butyric acid (100 mg) or 4-(2-(2-carboxy-ethyl)-3-{6-[3-iodo-5-(4-methyl-piperazine-1-carbonyl)-phenoxy]-hexyl}-phenoxy)-butyric acid (100 mg), arylboronic acid (2 eq.), potassium carbonate (1 eq.), and Pd(PPh$_3$)$_4$ (5 mg) were combined in 3 mL of EtOH and microwaved at 160° C. for 20 min. The reaction mixture was filtered through a syringe filter and concentrated under reduced pressure. The crude material was purified by reverse-phase HPLC.

The title compound was prepared according to the general procedure described above using 4-methoxyphenylboronic acid (55% yield).

HRMS calcd for $C_{40}H_{45}NO_8$ [M+H]$^+$ 668.3218, observed 668.3219

Example 2

4-[3-[6-(5-Benzylcarbamoyl-4'-fluoro-biphenyl-3-yloxy)-hexyl]-2-(2-carboxy-ethyl)-phenoxy]-butyric acid

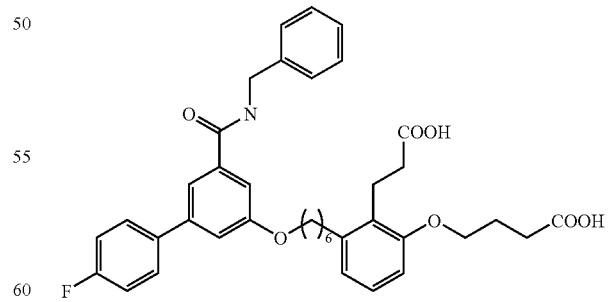

The title compound was prepared according to the general procedure described in Example 1 using 4-fluorophenylboronic acid (45% yield).

HRMS calcd for $C_{39}H_{42}FNO_7$ [M+H]$^+$ 656.3018, observed 656.3024

Example 3

4-[3-[6-(5-Benzylcarbamoyl-3'-methyl-biphenyl-3-yloxy)-hexyl]-2-(2-carboxy-ethyl)-phenoxy]-butyric acid

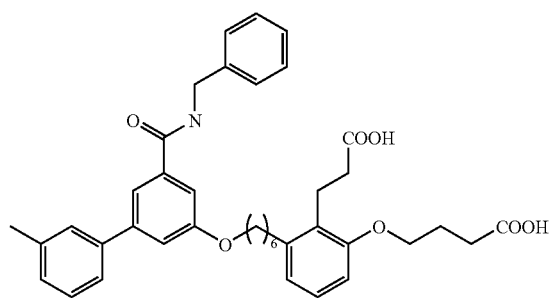

The title compound was prepared according to the general procedure described in Example 1 using 3-methylphenylboronic acid (67% yield).

HRMS calcd for $C_{40}H_{45}NO_7$ [M+H]$^+$ 652.3269, observed 652.3274

Example 4

4-[3-[6-(5-Benzylcarbamoyl-2'-chloro-biphenyl-3-yloxy)-hexyl]-2-(2-carboxy-ethyl)-phenoxy]-butyric acid

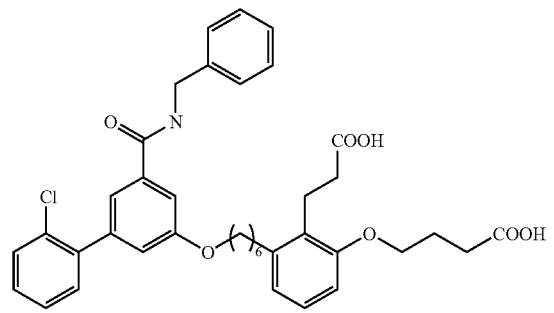

The title compound was prepared according to the general procedure described in Example 1 using 2-chlorophenylboronic acid.

HRMS calcd for $C_{39}H_{42}ClNO_7$ [M+H]$^+$ 672.2723, observed 672.2723

Example 5

4-[3-[6-(5-Benzylcarbamoyl-2',6'-difluoro-biphenyl-3-yloxy)-hexyl]-2-(2-carboxy-ethyl)-phenoxy]-butyric acid

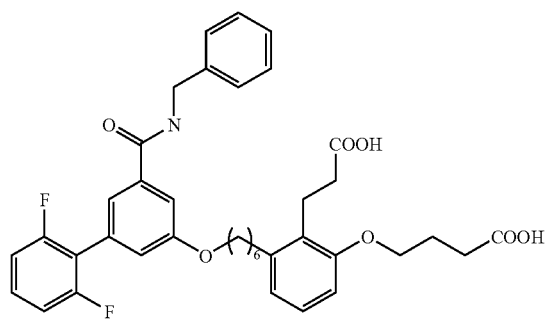

The title compound was prepared according to the general procedure described in Example 1 using 2,6-difluorophenylboronic acid.

HRMS calcd for $C_{39}H_{41}F_2NO_7$ [M+H]$^+$ 674.2924, observed 674.2923

Example 6

4-[3-[6-(5-Benzylcarbamoyl-4'-dimethylamino-biphenyl-3-yloxy)-hexyl]-2-(2-carboxy-ethyl)-phenoxy]-butyric acid The title compound was prepared according to the general procedure described in Example 1 using 4-(dimethylamino)phenylboronic acid.

HRMS calcd for $C_{41}H_{48}N_2O_7$ [M+H]$^+$ 681.3535, observed 681.3536

Example 7

4-[3-[6-(3-Benzylcarbamoyl-5-pyridin-3-yl-phenoxy)-hexyl]-2-(2-carboxy-ethyl)-phenoxy]-butyric acid

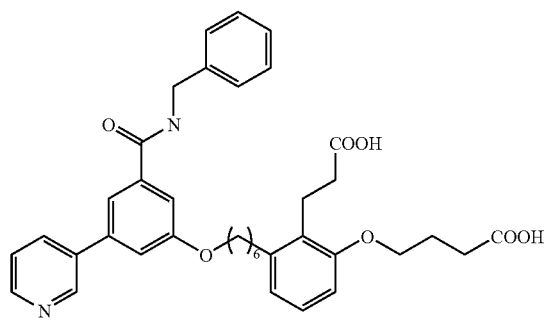

The title compound was prepared according to the general procedure described in Example 1 using pyridine-3-boronic acid.

HRMS calcd for $C_{38}H_{42}N_2O_7$ [M+H]$^+$ 639.3065, observed 639.3065

Example 8

4-[3-[6-(3-Benzylcarbamoyl-5-thiophen-3-yl-phenoxy)-hexyl]-2-(2-carboxy-ethyl)-phenoxy]-butyric acid

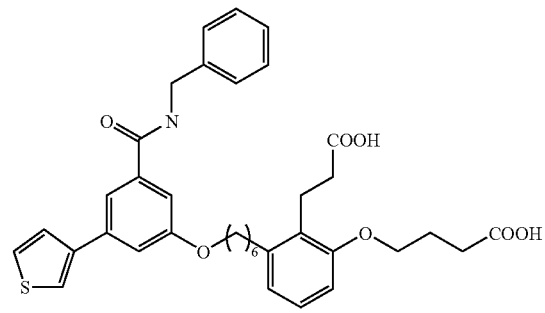

The title compound was prepared according to the general procedure described in Example 1 using thiophene-3-boronic acid.

HRMS calcd for $C_{37}H_{41}NO_7S$ [M+H]$^+$ 644.2677, observed 644.2678

Example 9

4-[3-[6-(3-Benzo[1,3]dioxol-5-yl-5-benzylcarbamoyl-phenoxy)-hexyl]-2-(2-carboxy-ethyl)-phenoxy]-butyric acid

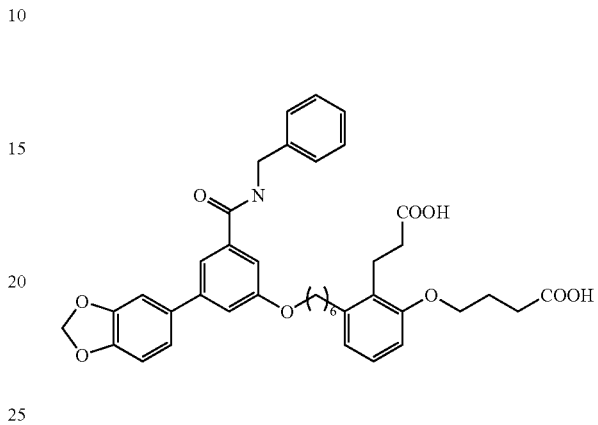

The title compound was prepared according to the general procedure described in Example 1 using 3,4-methylenedioxyphenylboronic acid.

HRMS calcd for $C_{40}H_{43}NO_9$ [M+H]$^+$ 682.3011, observed 682.3013

Example 10

4-[3-[6-(5-Benzylcarbamoyl-3'-fluoro-4'-methoxy-biphenyl-3-yloxy)-hexyl]-2-(2-carboxy-ethyl)-phenoxy]-butyric acid

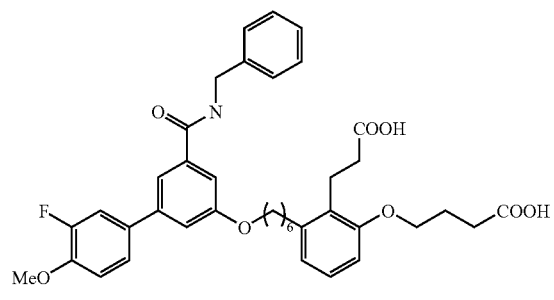

The title compound was prepared according to the general procedure described in Example 1 using 3-fluoro-4-methoxyphenylboronic acid.

HRMS calcd for $C_{40}H_{44}FNO_8$ [M+H]$^+$ 686.3124, observed 686.3128

Example 11

4-[3-[6-(5-Benzylcarbamoyl-4'-fluoro-3'-methyl-biphenyl-3-yloxy)-hexyl]-2-(2-carboxy-ethyl)-phenoxy]-butyric acid

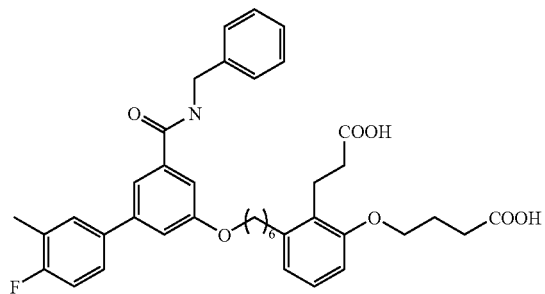

The title compound was prepared according to the general procedure described in Example 1 using 4-fluoro-3-methylphenylboronic acid.

HRMS calcd for $C_{40}H_{44}FNO_7$ [M+H]$^+$ 670.3175, observed 670.3175

Example 12

4-[3-{6-[3-Benzylcarbamoyl-5-(4-methyl-thiophen-3-yl)-phenoxy]-hexyl}-2-(2-carboxy-ethyl)-phenoxy]-butyric acid

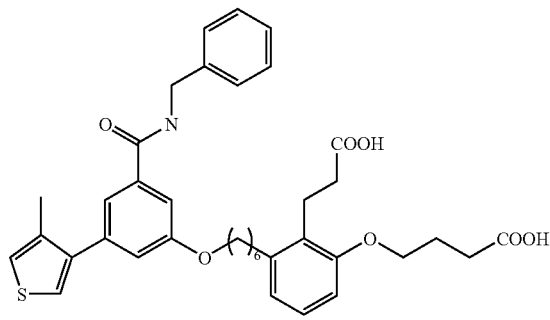

The title compound was prepared according to the general procedure described in Example 1 using 4-methyl-3-thiopheneboronic acid.

HRMS calcd for $C_{38}H_{43}NO_7S$ [M+H]$^+$ 658.2833, observed 658.2838

Example 13

4-[3-{6-[3-Benzylcarbamoyl-5-(4-methyl-3,4-dihydro-2H-benzo[1,4]oxazin-7-yl)-phenoxy]-hexyl}-2-(2-carboxy-ethyl)-phenoxy]-butyric acid

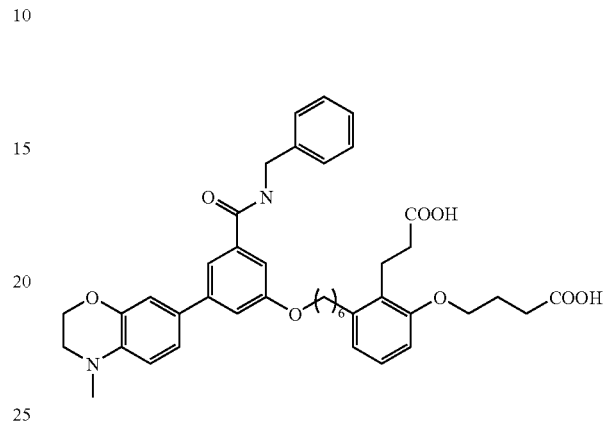

The title compound was prepared according to the general procedure described in Example 1 using 4-methyl-7-(4,4,5,5-tetramethyl-1,3,2-dioxaborolan-2-yl)-3,4-dihydro-2H-1,4-benzoxazine.

HRMS calcd for $C_{42}H_{48}N_2O_8$ [M+Na]$^+$731.3303, observed 731.3306

Example 14

4-[3-[6-(5-Benzylcarbamoyl-2'-fluoro-biphenyl-3-yloxy)-hexyl]-2-(2-carboxy-ethyl)-phenoxy]-butyric acid

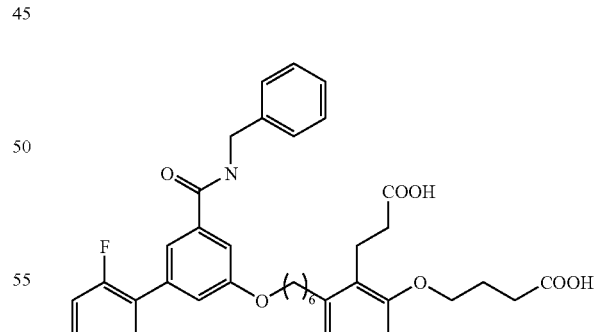

The title compound was prepared according to the general procedure described in Example 1 using 2-fluorophenylboronic acid.

HRMS calcd for $C_{39}H_{42}FNO_7$ [M+H]$^+$ 656.3018, observed 656.3022

Example 15

4-[3-{6-[3-Benzylcarbamoyl-5-(2,3-dihydro-benzo[1,4]dioxin-6-yl)-phenoxy]-hexyl}-2-(2-carboxy-ethyl)-phenoxy]-butyric acid

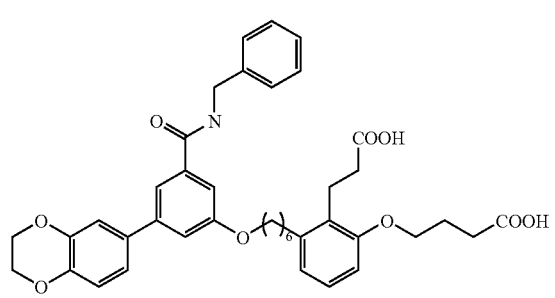

The title compound was prepared according to the general procedure described in Example 1 using 1,4-benzodioxane-6-boronic acid.

HRMS calcd for $C_{41}H_{45}NO_9$ [M+H]$^+$ 696.3167, observed 696.3169

Example 16

4-[3-[6-(5-Benzylcarbamoyl-4'-chloro-biphenyl-3-yloxy)-hexyl]-2-(2-carboxy-ethyl)-phenoxy]-butyric acid

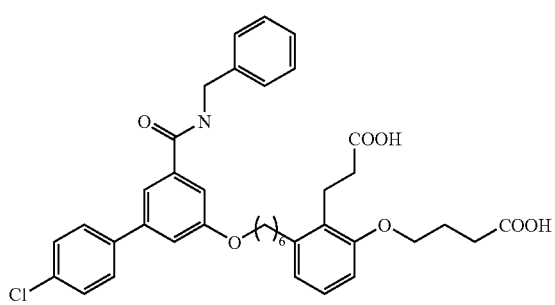

The title compound was prepared according to the general procedure described in Example 1 using 4-chlorophenylboronic acid.

HRMS calcd for $C_{39}H_{42}ClNO_7$ [M+H]$^+$ 672.2723, observed 672.2719

Example 17

4-[3-[6-(3-Benzylcarbamoyl-5-furan-3-yl-phenoxy)-hexyl]-2-(2-carboxy-ethyl)-phenoxy]-butyric acid

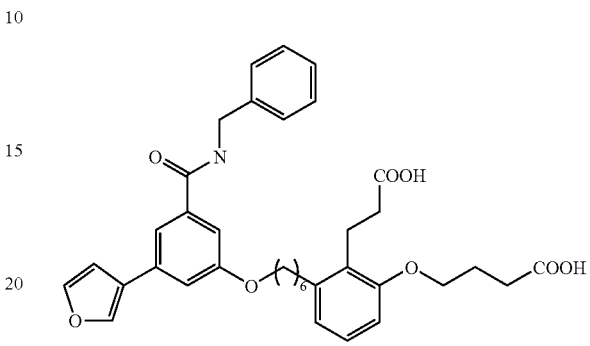

The title compound was prepared according to the general procedure described in Example 1 using furan-3-boronic acid.

HRMS calcd for $C_{37}H_{41}NO_8$ [M+H]$^+$ 628.2905, observed 628.2905

Example 18

4-[3-[6-(5-Benzylcarbamoyl-3'-fluoro-biphenyl-3-yloxy)-hexyl]-2-(2-carboxy-ethyl)-phenoxy]-butyric acid

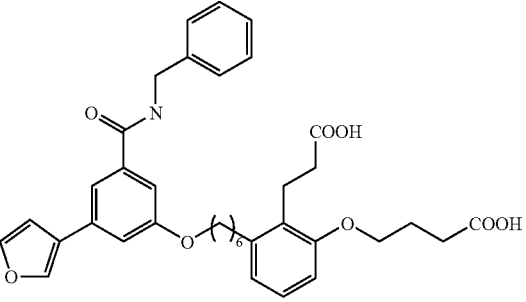

The title compound was prepared according to the general procedure described in Example 1 using 3-fluorophenylboronic acid.

HRMS calcd for $C_{39}H_{42}FNO_7$ [M+H]$^+$ 656.3018, observed 656.3022

Example 19

4-(2-(2-Carboxy-ethyl)-3-{6-[3-furan-3-yl-5-(4-methyl-piperazine-1-carbonyl)-phenoxy]-hexyl}-phenoxy)-butyric acid

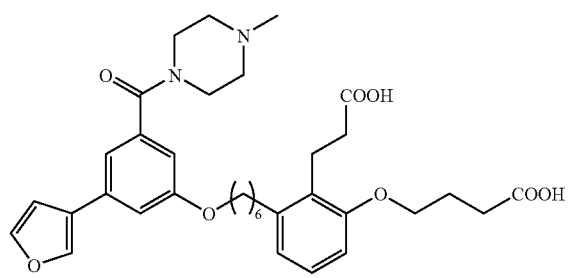

The title compound was prepared according to the general described in Example 1 procedure using furan-3-boronic acid.

HRMS calcd for $C_{35}H_{44}N_2O_8$ [M+H]$^+$ 621.3171, observed 621.3168

Example 20

4-[3-{6-[3-Benzo[1,3]dioxol-5-yl-5-(4-methyl-piperazine-1-carbonyl)-phenoxy]-hexyl}-2-(2-carboxy-ethyl)-phenoxy]-butyric acid

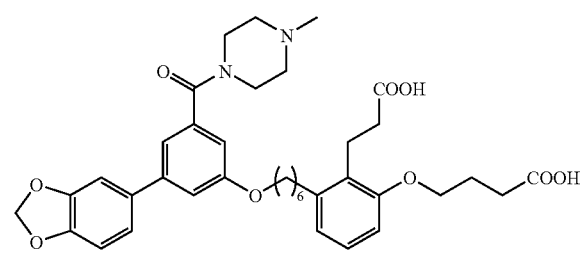

The title compound was prepared according to the general procedure described in Example 1 using 3,4-methylenedioxyphenylboronic acid.

HRMS calcd for $C_{38}H_{46}N_2O_9$ [M+H]$^+$ 675.3276, observed 675.3273

Example 21

4-(2-(2-Carboxy-ethyl)-3-{6-[3-(4-methyl-piperazine-1-carbonyl)-5-thiophen-3-yl-phenoxy]-hexyl}-phenoxy)-butyric acid

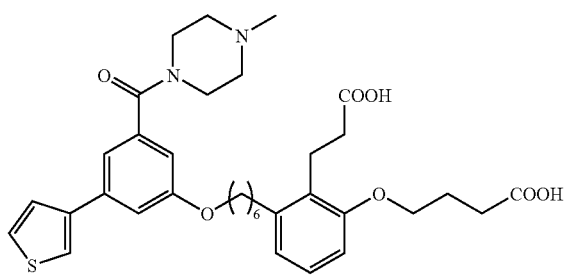

The title compound was prepared according to the general procedure described in Example 1 using thiophene-3-boronic acid.

HRMS calcd for $C_{35}H_{44}N_2O_7S$ [M+H]$^+$ 637.2942, observed 637.294

Example 22

4-(2-(2-Carboxy-ethyl)-3-{6-[3-(2,3-dihydro-benzo[1,4]dioxin-6-yl)-5-(4-methyl-piperazine-1-carbonyl)-phenoxy]-hexyl}-phenoxy)-butyric acid

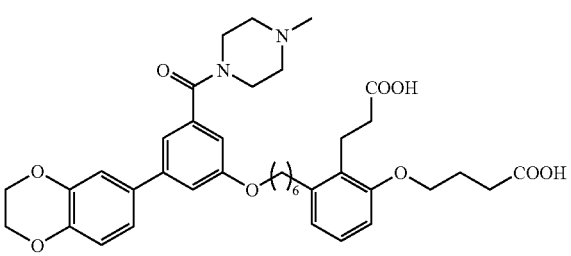

The title compound was prepared according to the general procedure described in Example 1 using 1,4-benzodioxane-6-boronic acid.

HRMS calcd for $C_{39}H_{48}N_2O_9$ [M+H]$^+$ 689.3433, observed 689.3431

Example 23

4-(2-(2-Carboxy-ethyl)-3-{6-[3-(4-methyl-3,4-dihydro-2H-benzo[1,4]oxazin-7-yl)-5-(4-methyl-piperazine-1-carbonyl)-phenoxy]-hexyl}-phenoxy)-butyric acid

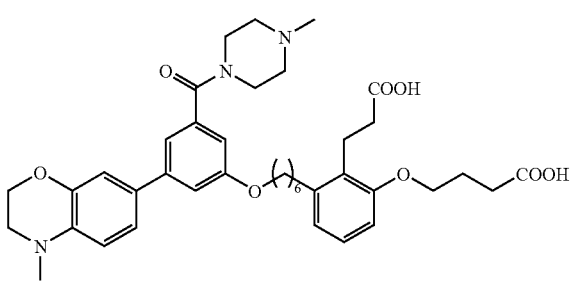

The title compound was prepared according to the general procedure described in Example 1 using 4-methyl-7-(4,4,5,5-tetramethyl-1,3,2-dioxaborolan-2-yl)-3,4-dihydro-2H-1,4-benzoxazine.

HRMS calcd for $C_{40}H_{51}N_3O_8$ [M+H]$^+$ 702.3749, observed 702.3748

Example 24

4-(2-(2-Carboxy-ethyl)-3-{6-[3-(4-methyl-piperazine-1-carbonyl)-5-(4-methyl-thiophen-3-yl)-phenoxy]-hexyl}-phenoxy)-butyric acid

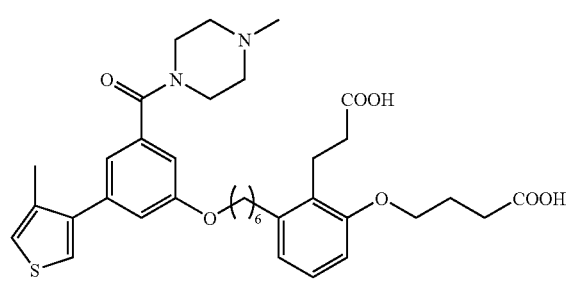

The title compound was prepared according to the general procedure described in Example 1 using 4-methyl-3-thiopheneboronic acid.

HRMS calcd for $C_{36}H_{46}N_2O_7S$ [M+H]$^+$ 651.3099, observed 651.3103

Example 25

4-(2-(2-Carboxy-ethyl)-3-{6-[4'-chloro-5-(4-methyl-piperazine-1-carbonyl)-biphenyl-3-yloxy]-hexyl}-phenoxy)-butyric acid

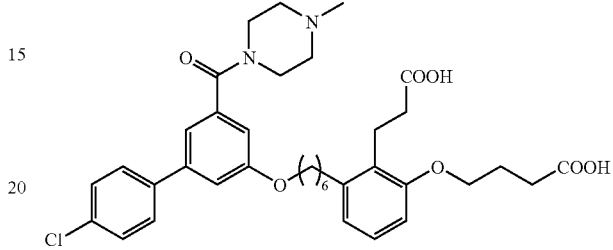

The title compound was prepared according to the general procedure described in Example 1 using 4-chlorophenylboronic acid.

LRMS calcd for $C_{37}H_{45}ClN_2O_7$ [M+H]$^+$ 664.3 observed 664.9

Example 26

4-(2-(2-Carboxy-ethyl)-3-{6-[3'-fluoro-5-(4-methyl-piperazine-1-carbonyl)-biphenyl-3-yloxy]-hexyl}-phenoxy)-butyric acid

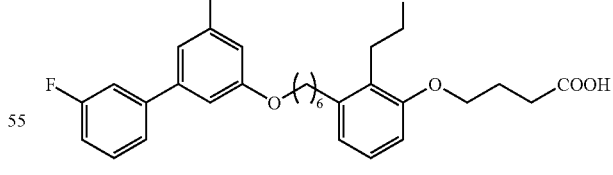

The title compound was prepared according to the general procedure described in Example 1 using 3-fluorophenylboronic acid.

LRMS calcd for $C_{37}H_{45}FN_2O_7$ [M+H]$^+$ 649.3, observed 649.6

Example 27

4-(2-(2-Carboxy-ethyl)-3-{6-[3-(4-methyl-piperazine-1-carbonyl)-5-(1-methyl-1H-pyrrol-2-yl)-phenoxy]-hexyl}-phenoxy)-butyric acid

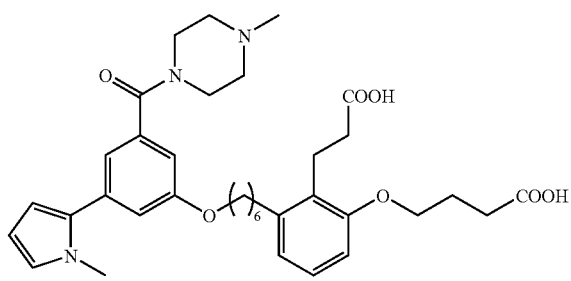

The title compound was prepared according to the general procedure described in Example 1 using 1-methyl-1H-pyrrole-2-boronic acid pinacol ester.

HRMS calcd for $C_{36}H_{47}N_3O_7$ [M+H]$^+$ 634.3487, observed 634.3484

Example 28

4-(2-(2-Carboxy-ethyl)-3-{6-[5-(4-methyl-piperazine-1-carbonyl)-biphenyl-3-yloxy]-hexyl}-phenoxy)-butyric acid

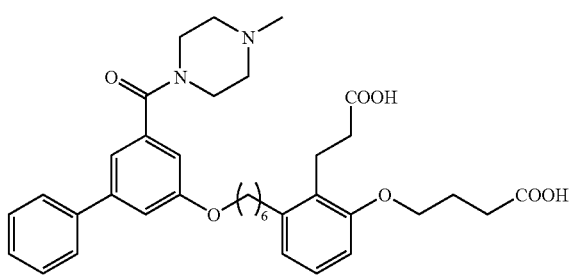

The title compound was prepared according to the general procedure described in Example 1 using phenylboronic acid.

LRMS calcd for $C_{37}H_{46}N_2O_7$ [M+H]$^+$ 631.3, observed 631.6

Example 29

4-(2-(2-Carboxy-ethyl)-3-{6-[2'-fluoro-5-(4-methyl-piperazine-1-carbonyl)-biphenyl-3-yloxy]-hexyl}-phenoxy)-butyric acid

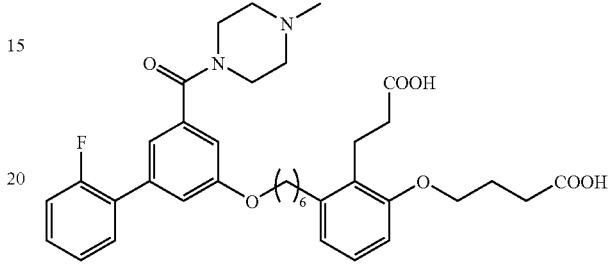

The title compound was prepared according to the general procedure described in Example 1 using 2-fluorophenylboronic acid.

HRMS calcd for $C_{37}H_{45}FN_2O_7$ [M+H]$^+$ 649.3284, observed 649.3283

Example 30

4-(2-(2-Carboxy-ethyl)-3-{6-[2',4'-difluoro-5-(4-methyl-piperazine-1-carbonyl)-biphenyl-3-yloxy]-hexyl}-phenoxy)-butyric acid

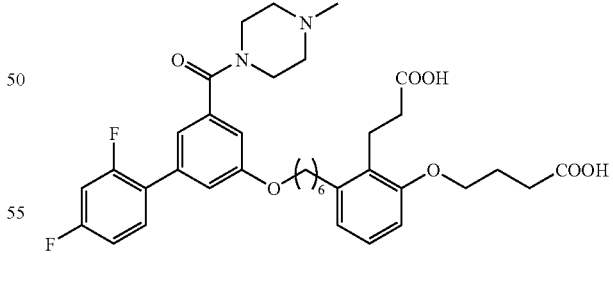

The title compound was prepared according to the general procedure described in Example 1 using 2,4-difluorophenylboronic acid.

HRMS calcd for $C_{37}H_{44}F_2N_2O_7$ [M+H]$^+$ 667.319, observed 667.3186

Example 31

4-(2-(2-Carboxy-ethyl)-3-{6-[3-(4-methyl-piperazine-1-carbonyl)-5-pyridin-3-yl-phenoxy]-hexyl}-phenoxy)-butyric acid

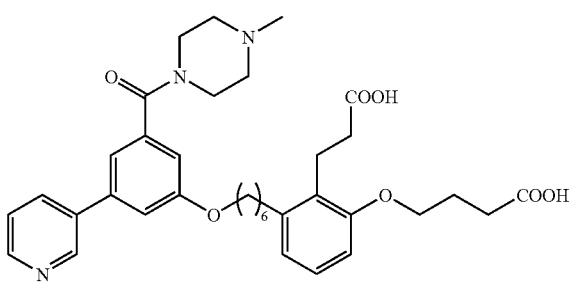

The title compound was prepared according to the general procedure described in Example 1 using pyridine-3-boronic acid.

LRMS calcd for $C_{36}H_{45}N_3O_7$ 632.3, observed 632.3

Example 32

4-(2-(2-Carboxy-ethyl)-3-{6-[4'-dimethylamino-5-(4-methyl-piperazine-1-carbonyl)-biphenyl-3-yloxy]-hexyl}-phenoxy)-butyric acid

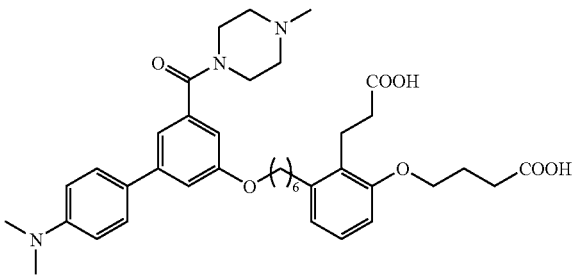

The title compound was prepared according to the general procedure described in Example 1 using 4-(dimethylamino)phenylboronic acid.

HRMS calcd for $C_{39}H_{51}N_3O_7$ [M+H]$^+$ 674.38, observed 674.3798

Example 33

4-(2-(2-Carboxy-ethyl)-3-{6-[2',6'-difluoro-5-(4-methyl-piperazine-1-carbonyl)-biphenyl-3-yloxy]-hexyl}-phenoxy)-butyric acid

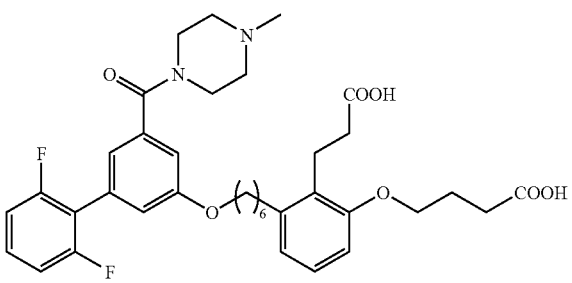

The title compound was prepared according to the general procedure described in Example 1 using 2,6-difluorophenyl-boronic acid.

HRMS calcd for $C_{37}H_{44}F_2N_2O_7$ [M+H]$^+$ 667.319, observed 667.3188

Example 34

4-(2-(2-Carboxy-ethyl)-3-{6-[4'-methoxy-5-(4-methyl-piperazine-1-carbonyl)-biphenyl-3-yloxy]-hexyl}-phenoxy)-butyric acid

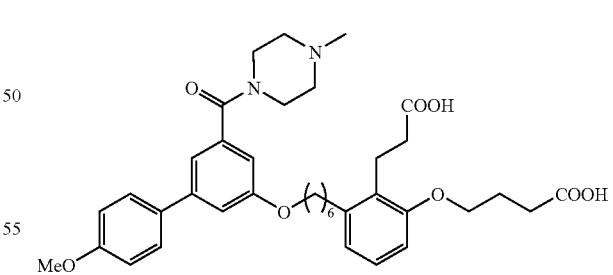

The title compound was prepared according to the general procedure described in Example 1 using 4-methoxyphenyl-boronic acid.

HRMS calcd for $C_{38}H_{48}N_2O_8$ [M+H]$^+$ 661.3484, observed 661.3481

Method B

Step 1: 3-Benzyloxy-5-hydroxy-benzoic acid methyl ester

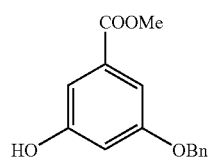

3,5-Dihydrobenzoic acid methyl ester (20.2 g) was dissolved in acetone (400 mL) and then potassium carbonate (16.6 g) and benzyl bromide (20.5 g) were added. The resulting mixture was refluxed for 3 h. Then the insoluble material was filtered off and the filtrate was concentrated under reduced pressure. The residue was purified on a silica gel column using chloroform and methanol to yield 12.4 g (40% yield) of the title compound.

HRMS calcd for $C_{15}H_{14}O_4$ [M+H]$^+$ 259.0965, observed 259.0965

Step 2: 3-Benzyloxy-5-trifluoromethanesulfonyloxy-benzoic acid methyl ester

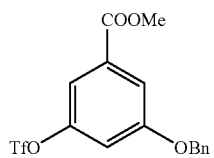

3-Benzyloxy-5-hydroxy-benzoic acid methyl ester (12.4 g) was dissolved in dry dichloromethane (250 mL) and triethylamine (5.9 g) was added. The resulting mixture was cooled in an ice-bath and a solution of triflic anhydride (14.7 g) in dichloromethane (30 mL) was added dropwise. After the addition was completed, the cooling bath was removed and the reaction mixture was stirred at room temperature for 3 h. Then it was washed with saturated sodium bicarbonate solution, water, 5% HCl and water again. The organic extract was dried over magnesium sulfate and concentrated under reduced pressure to afford 17.5 g (93% yield) of the title compound.

HRMS calcd for $C_{16}H_{13}F_3O_6S$ M$^+$ 390.0385, observed 390.0381

Step 3: 3-Benzo[1,3]dioxol-5-yl-5-benzyloxy-benzoic acid methyl ester

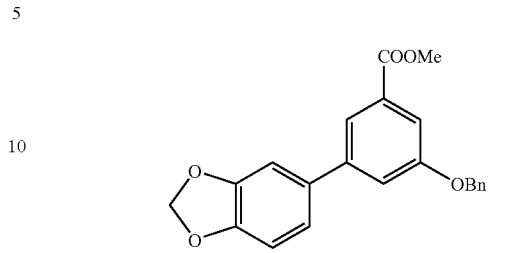

3-Benzyloxy-5-trifluoromethanesulfonyloxy-benzoic acid methyl ester (15.4 g) was dissolved in 1,2-dimethoxy-ethane (250 mL), followed by addition of Pd(PPh$_3$)$_4$ (2.5 g), solution of sodium carbonate (12 g) in water (120 mL) and 3,4-methylenedioxyphenylboronic acid (8.4 g). The resulting reaction mixture was refluxed under the flow of nitrogen for 5 h. After cooling the organic layer was separated and washed with water and then dried over magnesium sulfate. The crude material was purified on a silica gel column using ethyl acetate and hexanes to yield 14.2 g (99% yield) of the title compound.

HRMS calcd for $C_{22}H_{18}O_5$ [M+H]$^+$ 363.1227, observed 363.1228

Step 4: 3-Benzo[1,3]dioxol-5-yl-5-benzyloxy-benzoic acid

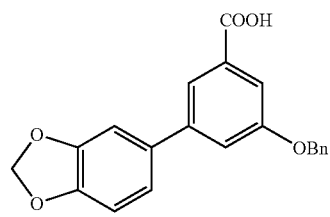

3-Benzo[1,3]dioxol-5-yl-5-benzyloxy-benzoic acid methyl ester (14.2 g) was dissolved in 1,4-dioxane (200 mL) and then 1 M aq. NaOH (40 mL) was added. The mixture was stirred at room temperature overnight. The solvents were removed under reduced pressure and the residue was diluted with water (200 mL). It was then made acidic by addition of 10% HCl (aq.) solution and the precipitated material was collected by filtration. The solid was washed with water and dried to yield 13.2 g (97% yield) of the title compound.

HRMS calcd for $C_{21}H_{16}O_5$ [M+H]$^+$ 349.1071, observed 349.1071

Steps 5 and 6

General Procedure:
3-Benzo[1,3]dioxol-5-yl-5-benzyloxy-benzoic acid (0.9 mmol), the appropriate amine component (1.1 molar eq.), TBTU (1.1 molar eq.), 4-methylmorpholine (2 molar eq.) and dry acetonitrile were combined together and stirred at room temperature for 12 h. The solvent was removed under reduced pressure and the residue was redissolved in dichloromethane (8 mL) and washed first with 10% aq. NaOH solution (3 mL), and then with water. The organic extract was dried over magnesium sulfate and concentrated to dryness. The material was used without further purification for the next step. The total amount of the product obtained from the previous step was dissolved in THF (25 mL) and hydrogenated in an H-Cube™ over Pd/C catalyst (flow rate 0.5 mL/min, pressure 70 bar, column temperature 70° C.). The product was triturated from n-hexane.

(3-Benzo[1,3]dioxol-5-yl-5-hydroxy-phenyl)-pyrrolidin-1-yl-methanone

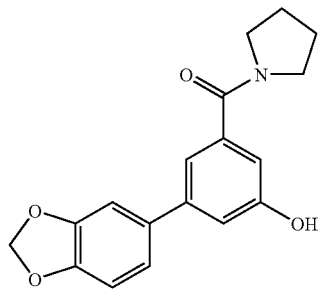

The title compound was prepared according to the general procedure described in Steps 5 and 6 of Method B using pyrrolidine as the amine component.

LRMS calcd for $C_{18}H_{17}NO_4$ [M+H]$^+$ 312.1, observed 312.3

(3-Benzo[1,3]dioxol-5-yl-5-hydroxy-phenyl)-(4-methyl-[1,4]diazepan-1-yl)-methanone

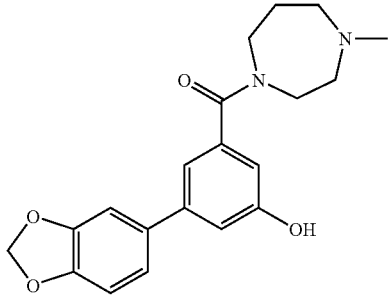

The title compound was prepared according to the general procedure described in Steps 5 and 6 of Method B using 1-methyl-[1,4]diazepane as the amine component.

LRMS calcd for $C_{20}H_{22}N_2O_4$ [M+H]$^+$ 355.2, observed 355.3

3-Benzo[1,3]dioxol-5-yl-N-benzo[1,3]dioxol-5-ylmethyl-5-hydroxy-benzamide

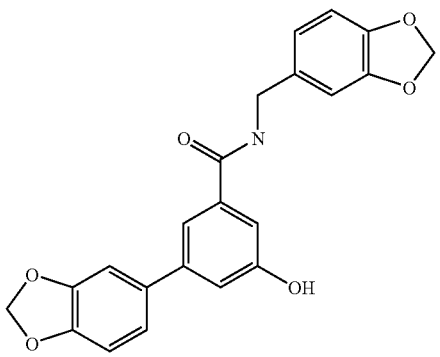

The title compound was prepared according to the general procedure described in Steps 5 and 6 of Method B using C-benzo[1,3]dioxol-5-yl-methylamine as the amine component.

LRMS calcd for $C_{22}H_{17}NO_6$ [M+H]$^+$ 392.1, observed 392.2

3-Benzo[1,3]dioxol-5-yl-N-(2,2-dimethyl-propyl)-5-hydroxy-benzamide

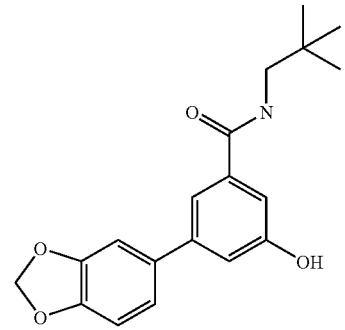

The title compound was prepared according to the general procedure described in Steps 5 and 6 of Method B using 2,2-dimethyl-propylamine as the amine component.

LRMS calcd for $C_{19}H_{21}NO_4$ [M+H]$^+$ 328.1, observed 328.3

(3-Benzo[1,3]dioxol-5-yl-5-hydroxy-phenyl)-morpholin-4-yl-methanone

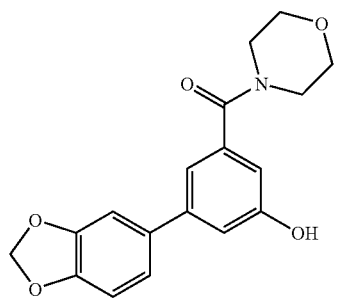

The title compound was prepared according to the general procedure described in Steps 5 and 6 of Method B using morpholine as the amine component.
LRMS calcd for $C_{18}H_{17}NO_5$ [M+H]$^+$ 328.1, observed 328.3

(3-Benzo[1,3]dioxol-5-yl-5-hydroxy-phenyl)-(2-methyl-piperidin-1-yl)-methanone

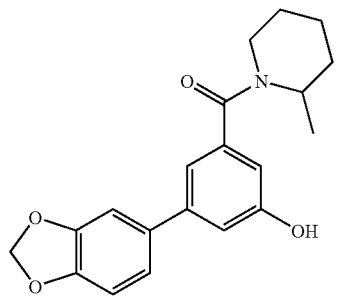

The title compound was prepared according to the general procedure described in Steps 5 and 6 of Method B using 2-methyl-piperidine as the amine component.
LRMS calcd for $C_{20}H_{21}NO_4$ [M+H]$^+$ 340.1, observed 340.3

3-Benzo[1,3]dioxol-5-yl-5-hydroxy-N-(1-phenyl-ethyl)-benzamide

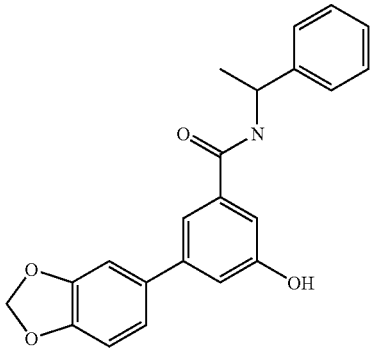

The title compound was prepared according to the general procedure described in Steps 5 and 6 of Method B using 1-phenyl-ethylamine as the amine component.
LRMS calcd for $C_{22}H_{19}NO_4$ [M+H]$^+$ 362.1, observed 362.3

(3-Benzo[1,3]dioxol-5-yl-5-hydroxy-phenyl)-piperidin-1-yl-methanone

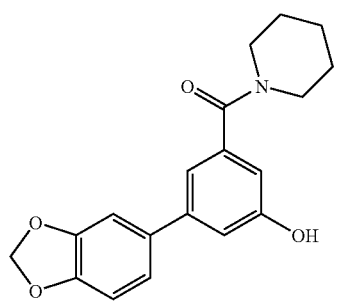

The title compound was prepared according to the general procedure described in Steps 5 and 6 of Method B using piperidine as the amine component.
LRMS calcd for $C_{19}H_{19}NO_4$ [M+H]$^+$ 326.1, observed 326.3

3-Benzo[1,3]dioxol-5-yl-5-hydroxy-N-methyl-N-phenyl-benzamide

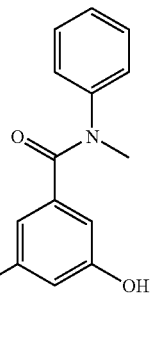

The title compound was prepared according to the general procedure described in Steps 5 and 6 of Method B using methyl-phenyl-amine as the amine component.
LRMS calcd for $C_{21}H_{17}NO_4$ [M+H]$^+$ 348.1, observed 348.4

61

1-[4-(3-Benzo[1,3]dioxol-5-yl-5-hydroxy-benzoyl)-piperazin-1-yl]-ethanone

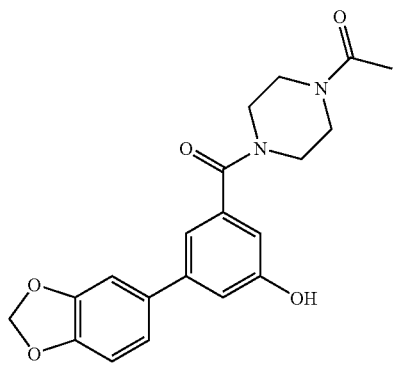

The title compound was prepared according to the general procedure described in Steps 5 and 6 of Method B using 1-piperazin-1-yl-methanone as the amine component.

LRMS calcd for $C_{20}H_{20}N_2O_5$ [M+H]$^+$ 369.1, observed 369.2

(3-Benzo[1,3]dioxol-5-yl-5-hydroxy-phenyl)-(5-ethyl-2-methyl-piperidin-1-yl)-methanone

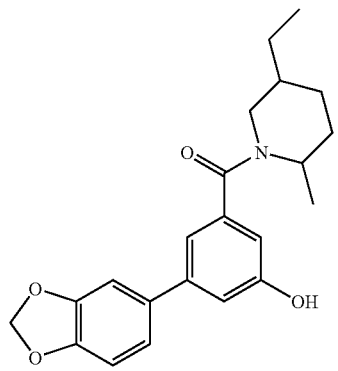

The title compound was prepared according to the general procedure described in Steps 5 and 6 of Method B using 5-ethyl-2-methyl-piperidine as the amine component.

LRMS calcd for $C_{22}H_{25}NO_4$ [M+H]$^+$ 368.2, observed 368.3

62

(3-Benzo[1,3]dioxol-5-yl-5-hydroxy-phenyl)-(3-methyl-piperidin-1-yl)-methanone

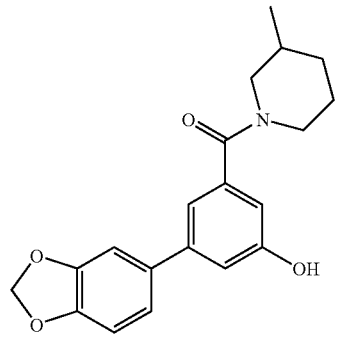

The title compound was prepared according to the general procedure described in Steps 5 and 6 of Method B using 3-methyl-piperidine as the amine component.

LRMS calcd for $C_{20}H_{21}NO_4$ [M+H]$^+$ 340.1, observed 340.3

3-Benzo[1,3]dioxol-5-yl-5-hydroxy-N-(2-methoxy-ethyl)-benzamide

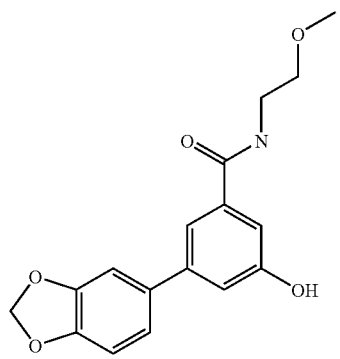

The title compound was prepared according to the general procedure described in Steps 5 and 6 of Method B using 2-methoxy-ethylamine as the amine component.

LRMS calcd for $C_{17}H_{17}NO_5$ [M−H]$^−$ 314.1, observed 314.4

63

(3-Benzo[1,3]dioxol-5-yl-5-hydroxy-phenyl)-(3,5-dimethyl-piperidin-1-yl)-methanone

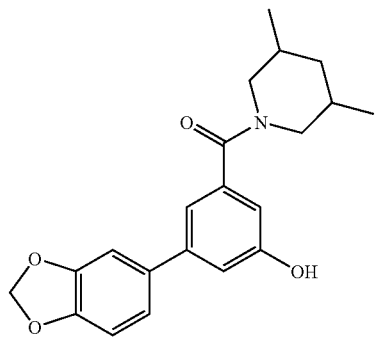

The title compound was prepared according to the general procedure described in Steps 5 and 6 of Method B using 3,5-dimethyl-piperidine as the amine component.

LRMS calcd for $C_{21}H_{23}NO_4$ [M+H]$^+$ 354.2, observed 354.3

3-Benzo[1,3]dioxol-5-yl-5-hydroxy-N-[2-(1-methyl-pyrrolidin-2-yl)-ethyl]-benzamide

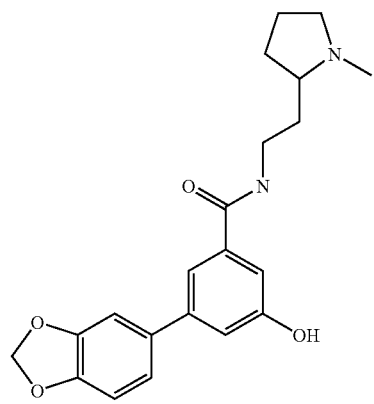

The title compound was prepared according to the general procedure described in Steps 5 and 6 of Method B using 2-(1-methyl-pyrrolidin-2-yl)-ethylamine as the amine component.

LRMS calcd for $C_{21}H_{24}N_2O_4$ [M+H]$^+$ 369.3, observed 369.3

64

3-Benzo[1,3]dioxol-5-yl-N-cyclopropyl-5-hydroxy-benzamide

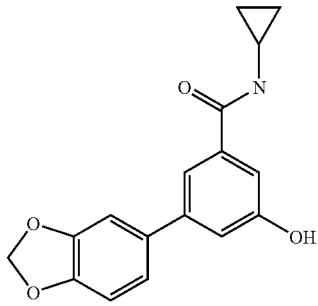

The title compound was prepared according to the general procedure described in Steps 5 and 6 of Method B using cyclopropylamine as the amine component.

LRMS calcd for $C_{17}H_{15}NO_4$ [M+H]$^+$ 298.1, observed 298.2

3-Benzo[1,3]dioxol-5-yl-5-hydroxy-N-phenyl-benzamide

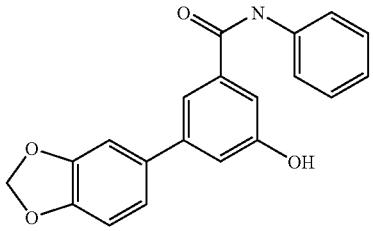

3-Benzo[1,3]dioxol-5-yl-5-benzyloxy-benzoic acid (500 mg), PyBroP (1.2 eq.), aniline (1.1 eq.), and triethylamine (2 eq.) were combined in dichloromethane (5 mL) and stirred at room temperature overnight. The reaction mixture was diluted with dichloromethane and washed with water. White solid which precipitated in dichloromethane layer was collected by filtration (493 mg). This material was dissolved in THF and hydrogenated over 10% Pd/C (50 mg) in Parr apparatus for 5 h. The catalyst was removed by filtration and the filtrate was concentrated under reduced pressure and purified on a silica gel column using ethyl acetate and hexanes to yield 362 mg of title compound (76% yield after 2 steps).

HRMS calcd for $C_{20}H_{15}NO_4$ [M+H]$^+$ 334.1074, observed 334.1073

3-Benzo[1,3]dioxol-5-yl-5-hydroxy-N,N-dimethyl-benzamide

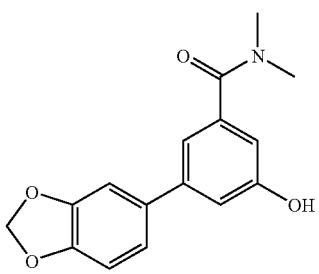

The title compound was prepared according to the general procedure described in Steps 5 and 6 of Method B using dimethylamine as the amine component.

LRMS calcd for $C_{16}H_{15}NO_4$ [M+H]$^+$ 286.1, observed 286.2

3-Benzo[1,3]dioxol-5-yl-5-hydroxy-N-pyridin-4-ylmethyl-benzamide

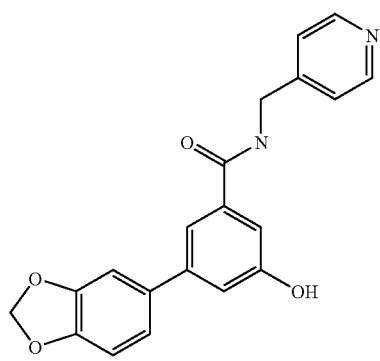

The title compound was prepared according to the general procedure described in Steps 5 and 6 of Method B using C-pyridin-4-yl-methylamine as the amine component.

LRMS calcd for $C_{20}H_{16}N_2O_4$ [M+H]$^+$ 349.1, observed 349.3

3-Benzo[1,3]dioxol-5-yl-5-hydroxy-benzamide

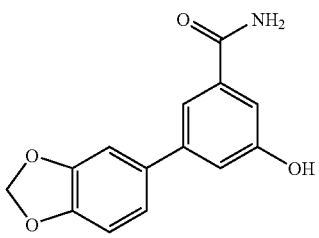

The title compound was prepared according to the general procedure described in Steps 5 and 6 of Method B using dry ammonia gas (bubbled through the reaction mixture for 10 min) as the amine component.

LRMS calcd for $C_{14}H_{11}NO_4$ [M+H]$^+$ 258.1, observed 258.1

3-Benzo[1,3]dioxol-5-yl-5-hydroxy-N-pyridin-3-ylmethyl-benzamide

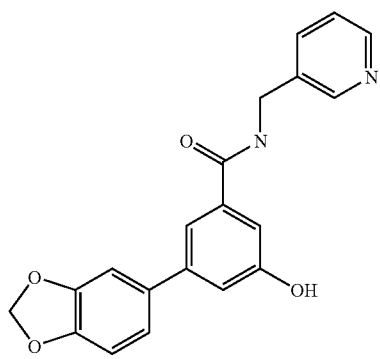

The title compound was prepared according to the general procedure described in Steps 5 and 6 of Method B using C-pyridin-3-yl-methylamine as the amine component.

LRMS calcd for $C_{20}H_{16}N_2O_4$ [M+H]$^+$ 349.1, observed 349.3

(3-Benzo[1,3]dioxol-5-yl-5-hydroxy-phenyl)-(3,3-dimethyl-piperidin-1-yl)-methanone

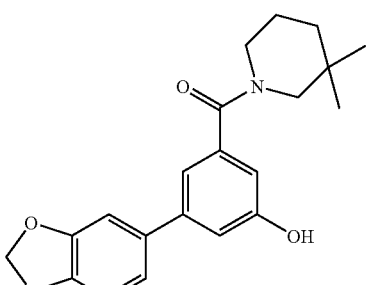

The title compound was prepared according to the general procedure described in Steps 5 and 6 of Method B using 3,3-dimethyl-piperidine as the amine component.

LRMS calcd for $C_{21}H_{23}NO_4$ [M+H]$^+$ 354.2, observed 354.3

4-(3-Benzo[1,3]dioxol-5-yl-5-hydroxy-benzoyl)-[1,4]diazepane-1-carboxylic acid tert-butyl ester

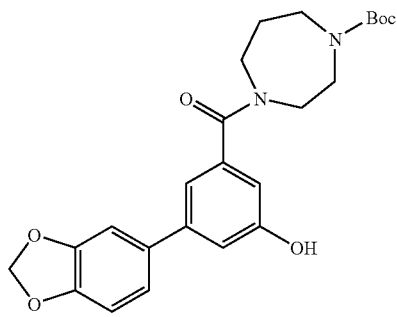

3-Benzo[1,3]dioxol-5-yl-5-benzyloxy-benzoic acid (500 mg), PyBroP (1.2 eq.), [1,4]diazepane-1-carboxylic acid tert-butyl ester (1.1 eq.), and triethylamine (2 eq.) were combined in dichloromethane (5 mL) and stirred at room temperature overnight. The reaction mixture was diluted with dichloromethane and washed with water and brine. The organic extract was dried over anhydrous sodium sulfate, concentrated under reduced pressure and purified on a silica gel column using ethyl acetate and hexanes to yield 503 mg of white solid. This material was dissolved in THF and hydrogenated over 10% Pd/C (50 mg) in Parr apparatus for 6 h. The catalyst was removed by filtration and the filtrate was concentrated under reduced pressure and purified on a silica gel column using dichloromethane and methanol to yield 400 mg of title compound (63% yield after 2 steps).

HRMS calcd for $C_{24}H_{28}N_2O_4$ [M+Na]$^+$ 463.1839, observed 463.1837

1-(3-Benzo[1,3]dioxol-5-yl-5-hydroxy-benzoyl)-[1,4]diazepan-5-one

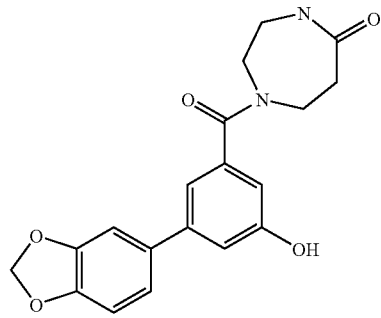

The title compound was prepared according to the general procedure described in Steps 5 and 6 of Method B using [1,4]diazepan-5-one as the amine component.

LRMS calcd for $C_{19}H_{18}N_2O_5$ [M+H]$^+$ 355.1, observed 355.2

3-Benzo[1,3]dioxol-5-yl-N-benzyl-5-hydroxy-N-methyl-benzamide

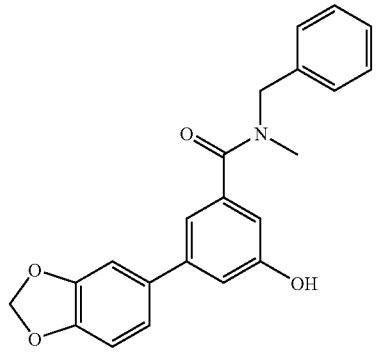

The title compound was prepared according to the general procedure described in Steps 5 and 6 of Method B using benzyl-methyl-amine as the amine component.

LRMS calcd for $C_{22}H_{19}NO_4$ [M+H]$^+$ 362.1, observed 362.2

3-Benzo[1,3]dioxol-5-yl-N-cyclobutyl-5-hydroxy-benzamide

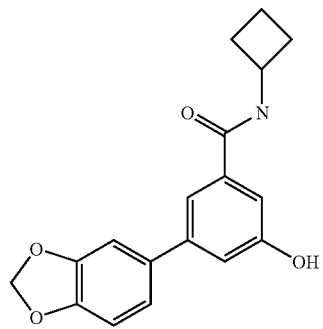

The title compound was prepared according to the general procedure described in Steps 5 and 6 of Method B using cyclobutylamine as the amine component.

LRMS calcd for $C_{18}H_{17}NO_4$ [M+H]$^+$ 312.1, observed 312.1

3-Benzo[1,3]dioxol-5-yl-5-hydroxy-N-isopropyl-benzamide

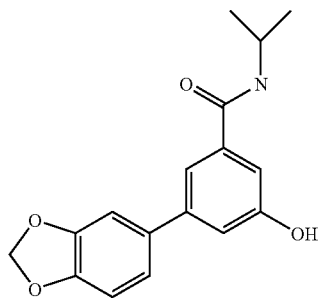

The title compound was prepared according to the general procedure described in Steps 5 and 6 of Method B using isopropylamine as the amine component.

LRMS calcd for $C_{17}H_{17}NO_4$ [M+H]$^+$ 300.1, observed 300.1

3-Benzo[1,3]dioxol-5-yl-5-yl-N-cyclopentyl-5-hydroxy-benzamide

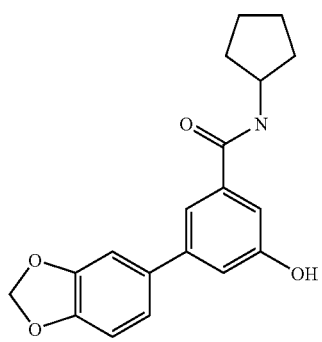

The title compound was prepared according to the general procedure described in Steps 5 and 6 of Method B using cyclopentylamine as the amine component.

LRMS calcd for $C_{19}H_{19}NO_4$ [M+H]$^+$ 326.1, observed 326.1

3-Benzo[1,3]dioxol-5-yl-N-cyclohexyl-5-hydroxy-benzamide

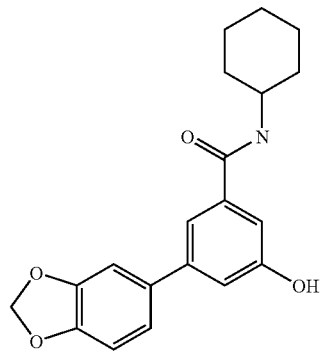

The title compound was prepared according to the general procedure described in Steps 5 and 6 of Method B using cyclohexylamine as the amine component.

LRMS calcd for $C_{20}H_{21}NO_4$ [M+H]$^+$ 340.1, observed 340.2

Steps 7 and 8:

General Procedure:

To a solution of a phenol (0.3 mmol) in a mixture of acetone and DMF (2:1, 2 mL) were added potassium carbonate (10 eq.) and 4-[3-(6-bromo-hexyl)-2-(2-ethoxycarbonyl-ethyl)-phenoxy]-butyric acid ethyl ester (1.1 eq). The resulting mixture was stirred at 75° C. for 2 days. Then the insoluble material was filtered out and the filtrate was diluted with ethyl acetate and washed with water and brine. The organic extract was dried over anhydrous sodium sulfate, concentrated and used for the next step without further purification. The total amount of material from the previous step was dissolved in EtOH (2 mL), followed by addition of 10 M NaOH solution (10 eq.). The resulting reaction mixture was stirred at room temperature overnight. Then it was neutralized with 3 N HCl and extracted into ethyl acetate. The organic extract was washed with water and brine and dried over anhydrous sodium sulfate. The crude material was purified by reverse-phase HPLC.

Example 35

4-[3-{6-[3-Benzo[1,3]dioxol-5-yl-5-(pyrrolidine-1-carbonyl)-phenoxy]-hexyl}-2-(2-carboxy-ethyl)-phenoxy]-butyric acid

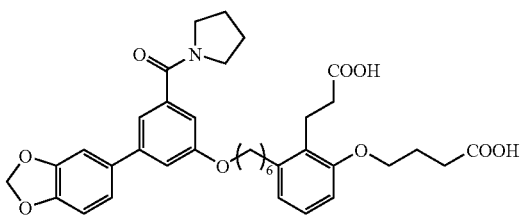

The title compound was prepared according to the general procedure described in Steps 7 and 8 of Method B starting from (3-benzo[1,3]dioxol-5-yl-5-hydroxy-phenyl)-pyrrolidin-1-yl-methanone (13% yield after two steps).

HRMS calcd for $C_{37}H_{43}NO_9$ [M+H]$^+$ 646.3011, observed 646.3008

Example 36

4-[3-{6-[3-Benzo[1,3]dioxol-5-yl-5-(4-methyl-[1,4]diazepane-1-carbonyl)-phenoxy]-hexyl}-2-(2-carboxy-ethyl)-phenoxy]-butyric acid

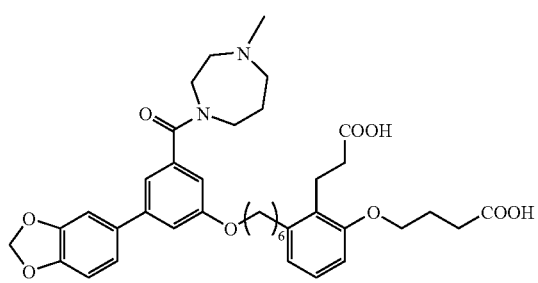

The title compound was prepared according to the general procedure described in Steps 7 and 8 of Method B starting from (3-benzo[1,3]dioxol-5-yl-5-hydroxy-phenyl)-(4-methyl-[1,4]diazepan-1-yl)-methanone (35% yield after two steps)

HRMS calcd for $C_{39}H_{48}N_2O_9$ 689.3433, observed 689.3428

Example 37

4-[3-(6-{3-Benzo[1,3]dioxol-5-yl-5-[(benzo[1,3]dioxol-5-ylmethyl)-carbamoyl]-phenoxy}-hexyl)-2-(2-carboxy-ethyl)-phenoxy]-butyric acid

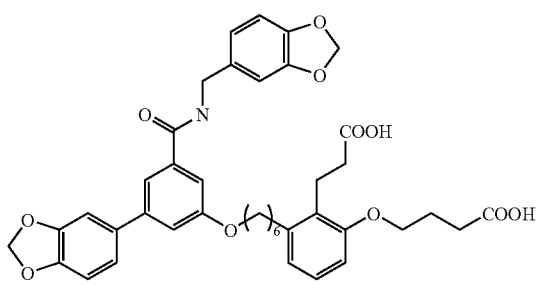

The title compound was prepared according to the general procedure described in Steps 7 and 8 of Method B starting from 3-benzo[1,3]dioxol-5-yl-N-benzo[1,3]dioxol-5-ylmethyl-5-hydroxy-benzamide (4% yield after two steps)

HRMS calcd for $C_{41}H_{43}NO_{11}$ [M+H]$^+$ 726.2909, observed 726.291

Example 38

4-[3-{6-[3-Benzo[1,3]dioxol-5-yl-5-(2,2-dimethyl-propylcarbamoyl)-phenoxy]-hexyl}-2-(2-carboxy-ethyl)-phenoxy]-butyric acid

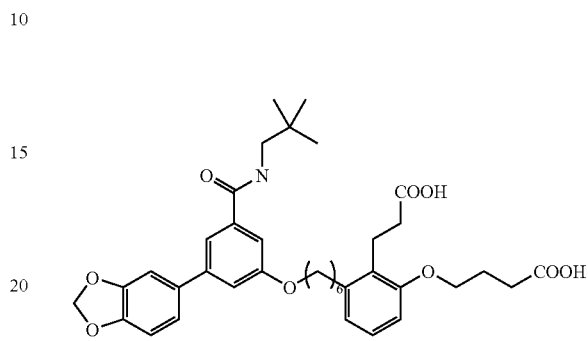

The title compound was prepared according to the general procedure described in Steps 7 and 8 of Method B starting from 3-benzo[1,3]dioxol-5-yl-N-(2,2-dimethyl-propyl)-5-hydroxy-benzamide.

HRMS calcd for $C_{38}H_{47}NO_9$ [M+H]$^+$ 662.3324, observed 662.3321

Example 39

4-[3-{6-[3-Benzo[1,3]dioxol-5-yl-5-(morpholine-4-carbonyl)-phenoxy]-hexyl}-2-(2-carboxy-ethyl)-phenoxy]-butyric acid

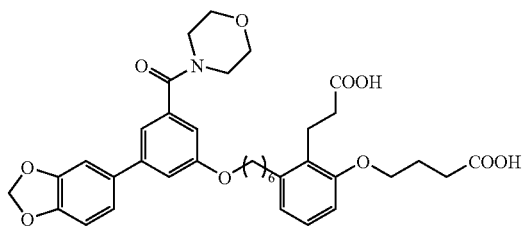

The title compound was prepared according to the general procedure described in Steps 7 and 8 of Method B starting from (3-benzo[1,3]dioxol-5-yl-5-hydroxy-phenyl)-morpholin-4-yl-methanone.

HRMS calcd for $C_{37}H_{43}NO_{10}$ [M+H]$^+$ 662.296, observed 662.2959

Example 40

4-[3-{6-[3-Benzo[1,3]dioxol-5-yl-5-(2-methyl-piperidine-1-carbonyl)-phenoxy]-hexyl}-2-(2-carboxy-ethyl)-phenoxy]-butyric acid

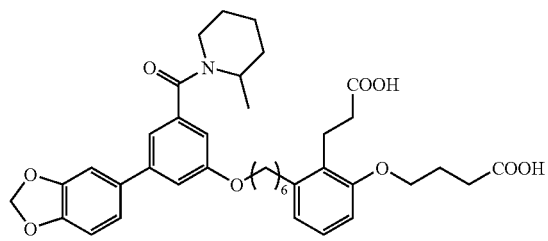

The title compound was prepared according to the general procedure described in Steps 7 and 8 of Method B starting from (3-benzo[1,3]dioxol-5-yl-5-hydroxy-phenyl)-(2-methyl-piperidin-1-yl)-methanone.

HRMS calcd for $C_{39}H_{47}NO_9$ $[M+H]^+$ 674.3324, observed 674.3322

Example 41

4-[3-{6-[3-Benzo[1,3]dioxol-5-yl-5-(1-phenyl-ethyl-carbamoyl)-phenoxy]-hexyl}-2-(2-carboxy-ethyl)-phenoxy]-butyric acid

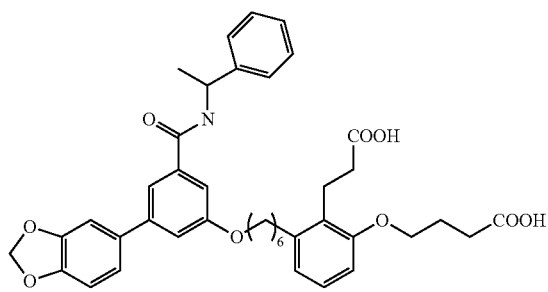

The title compound was prepared according to the general procedure described in Steps 7 and 8 of Method B starting from 3-benzo[1,3]dioxol-5-yl-5-hydroxy-N-(1-phenyl-ethyl)-benzamide.

HRMS calcd for $C_{41}H_{45}NO_9$ $[M+H]^+$ 696.3167, observed 696.3165

Example 42

4-[3-{6-[3-Benzo[1,3]dioxol-5-yl-5-(piperidine-1-carbonyl)-phenoxy]-hexyl}-2-(2-carboxy-ethyl)-phenoxy]-butyric acid

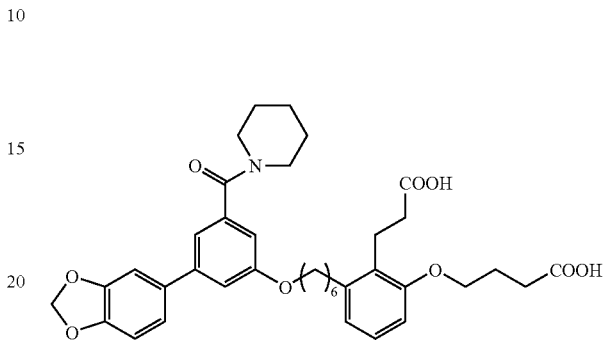

The title compound was prepared according to the general procedure described in Steps 7 and 8 of Method B starting from (3-benzo[1,3]dioxol-5-yl-5-hydroxy-phenyl)-piperidin-1-yl-methanone.

HRMS calcd for $C_{38}H_{45}NO_9$ 660.3, observed 660.5

Example 43

4-[3-{6-[3-Benzo[1,3]dioxol-5-yl-5-(methyl-phenyl-carbamoyl)-phenoxy]-hexyl}-2-(2-carboxy-ethyl)-phenoxy]-butyric acid

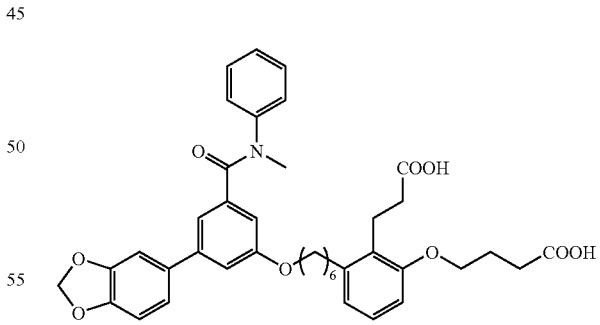

The title compound was prepared according to the general procedure described in Steps 7 and 8 of Method B starting from 3-benzo[1,3]dioxol-5-yl-5-hydroxy-N-methyl-N-phenyl-benzamide.

HRMS calcd for $C_{40}H_{43}NO_9$ $[M+H]^+$ 682.3011, observed 682.3013

Example 44

4-[3-{6-[3-Benzo[1,3]dioxol-5-yl-5-(piperazine-1-carbonyl)-phenoxy]-hexyl}-2-(2-carboxy-ethyl)-phenoxy]-butyric acid

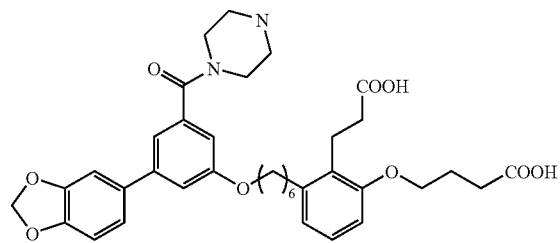

The title compound was prepared according to the general procedure described in Steps 7 and 8 of Method B starting from 1-[4-(3-benzo[1,3]dioxol-5-yl-5-hydroxy-benzoyl)-piperazin-1-yl]-ethanone. The acetyl group was removed during the saponification step.

HRMS calcd for $C_{37}H_{44}N_2O_9$ [M+H]$^+$ 661.312, observed 661.3122

Example 45

4-[3-{6-[3-Benzo[1,3]dioxol-5-yl-5-(5-ethyl-2-methyl-piperidine-1-carbonyl)-phenoxy]-hexyl}-2-(2-carboxy-ethyl)-phenoxy]-butyric acid

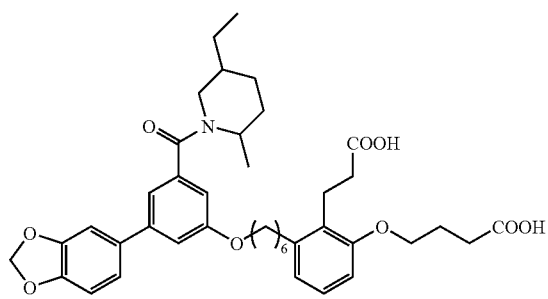

The title compound was prepared according to the general procedure described in Steps 7 and 8 of Method B starting from (3-benzo[1,3]dioxol-5-yl-5-hydroxy-phenyl)-(5-ethyl-2-methyl-piperidin-1-yl)-methanone.

HRMS calcd for $C_{41}H_{51}NO_9$ [M+H]$^+$ 702.3637, observed 702.3632

Example 46

4-[3-{6-[3-Benzo[1,3]dioxol-5-yl-5-(3-methyl-piperidine-1-carbonyl)-phenoxy]-hexyl}-2-(2-carboxy-ethyl)-phenoxy]-butyric acid

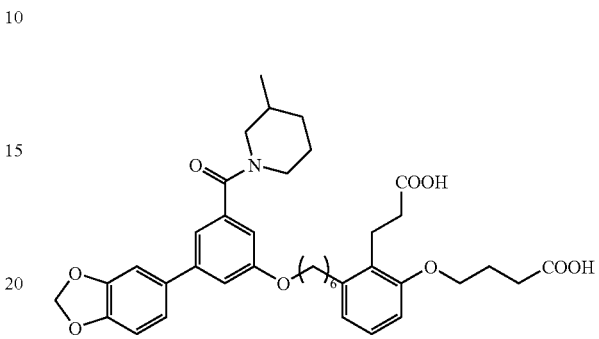

The title compound was prepared according to the general procedure described in Steps 7 and 8 of Method B starting from (3-benzo[1,3]dioxol-5-yl-5-hydroxy-phenyl)-(3-methyl-piperidin-1-yl)-methanone.

HRMS calcd for $C_{39}H_{47}NO_9$ [M+H]$^+$ 674.3324, observed 674.3322

Example 47

4-[3-{6-[3-Benzo[1,3]dioxol-5-yl-5-(2-methoxy-ethylcarbamoyl)-phenoxy]-hexyl}-2-(2-carboxy-ethyl)-phenoxy]-butyric acid

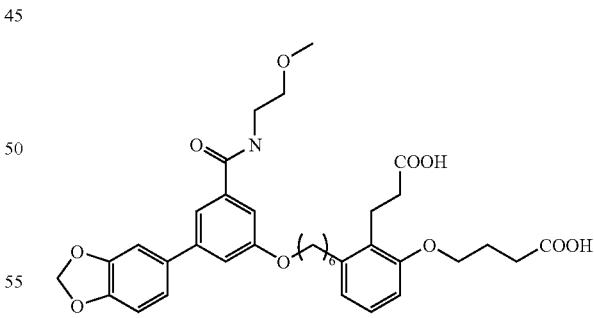

The title compound was prepared according to the general procedure described in Steps 7 and 8 of Method B starting from 3-benzo[1,3]dioxol-5-yl-5-hydroxy-N-(2-methoxy-ethyl)-benzamide.

HRMS calcd for $C_{36}H_{43}NO_{10}$ [M+H]$^+$ 650.296, observed 650.2959

Example 48

4-[3-{6-[3-(4-Acetyl-piperazine-1-carbonyl)-5-benzo[1,3]dioxol-5-yl-phenoxy]-hexyl}-2-(2-carboxy-ethyl)-phenoxy]-butyric acid

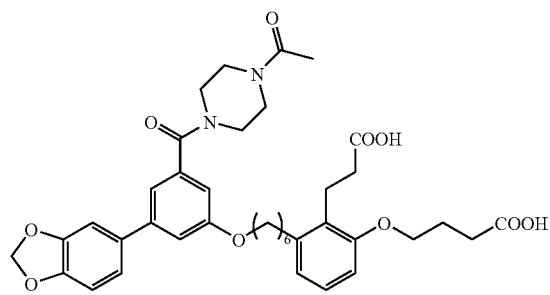

4-[3-{6-[3-Benzo[1,3]dioxol-5-yl-5-(piperazine-1-carbonyl)-phenoxy]-hexyl}-2-(2-carboxy-ethyl)-phenoxy]-butyric acid (0.29 mmol), acetic anhydride (1.2 eq.), triethylamine (3 eq.) were combined in dichloromethane (2 mL) and stirred overnight. Then the reaction mixture was diluted with ethyl acetate, washed with water and dried over anhydrous sodium sulfate. The organic extract was concentrated under reduced pressure and purified by reverse-phase HPLC to yield the title compound.

HRMS calcd for $C_{39}H_{46}N_2O_{10}$ [M+H]$^+$ 703.3225, observed 703.322

Example 49

4-[3-{6-[3-Benzo[1,3]dioxol-5-yl-5-(3,5-dimethyl-piperidine-1-carbonyl)-phenoxy]-hexyl}-2-(2-carboxy-ethyl)-phenoxy]-butyric acid

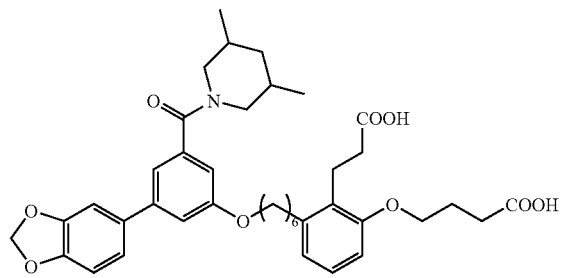

The title compound was prepared according to the general procedure described in Steps 7 and 8 of Method B starting from (3-benzo[1,3]dioxol-5-yl-5-hydroxy-phenyl)-(3,5-dimethyl-piperidin-1-yl)-methanone.

HRMS calcd for $C_{40}H_{49}NO_9$ [M+H]$^+$ 688.348, observed 688.348

Example 50

4-[3-(6-{3-Benzo[1,3]dioxol-5-yl-5-[2-(1-methyl-pyrrolidin-2-yl)-ethylcarbamoyl]-phenoxy}-hexyl)-2-(2-carboxy-ethyl)-phenoxy]-butyric acid

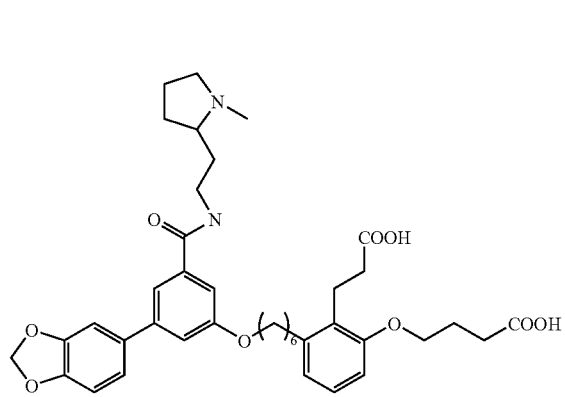

The title compound was prepared according to the general procedure described in Steps 7 and 8 of Method B starting from 3-benzo[1,3]dioxol-5-yl-5-hydroxy-N-[2-(1-methyl-pyrrolidin-2-yl)-ethyl]-benzamide.

HRMS calcd for $C_{40}H_{50}N_2O_9$ [M+H]$^+$ 703.3589, observed 703.3585

Example 51

4-[3-[6-(3-Benzo[1,3]dioxol-5-yl-5-cyclopropylcarbamoyl-phenoxy)-hexyl]-2-(2-carboxy-ethyl)-phenoxy]-butyric acid

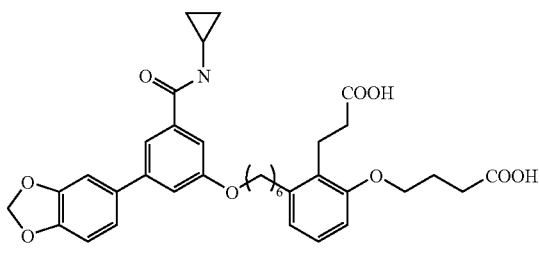

The title compound was prepared according to the general procedure described in Steps 7 and 8 of Method B starting from 3-benzo[1,3]dioxol-5-yl-N-cyclopropyl-5-hydroxy-benzamide.

HRMS calcd for $C_{36}H_{41}NO_9$ [M+H]$^+$ 632.2854, observed 632.2856

Example 52

4-[3-[6-(3-Benzo[1,3]dioxol-5-yl-5-phenylcarbamoyl-phenoxy)-hexyl]-2-(2-carboxy-ethyl)-phenoxy]-butyric acid

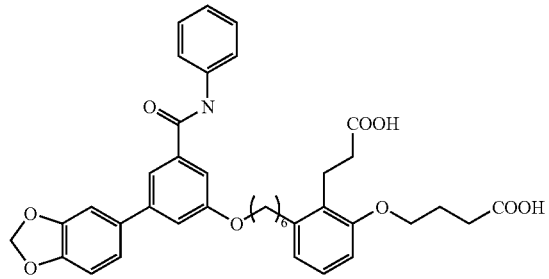

The title compound was prepared according to the general procedure described in Steps 7 and 8 of Method B starting from 3-benzo[1,3]dioxol-5-yl-5-hydroxy-N-phenyl-benzamide.

HRMS calcd for $C_{39}H_{41}NO_9$ [M+H]$^+$ 668.2854, observed 668.2853

Example 53

4-[3-[6-(3-Benzo[1,3]dioxol-5-yl-5-dimethylcarbamoyl-phenoxy)-hexyl]-2-(2-carboxy-ethyl)-phenoxy]-butyric acid

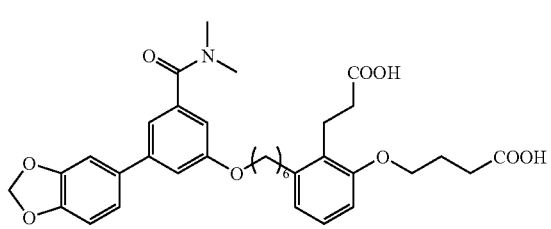

The title compound was prepared according to the general procedure described in Steps 7 and 8 of Method B starting from 3-benzo[1,3]dioxol-5-yl-5-hydroxy-N,N-dimethyl-benzamide.

HRMS calcd for $C_{35}H_{41}NO_9$ [M+H]$^+$ 620.2854, observed 620.2856

Example 54

4-[3-(6-{3-Benzo[1,3]dioxol-5-yl-5-[(pyridin-4-ylmethyl)-carbamoyl]-phenoxy}-hexyl)-2-(2-carboxy-ethyl)-phenoxy]-butyric acid

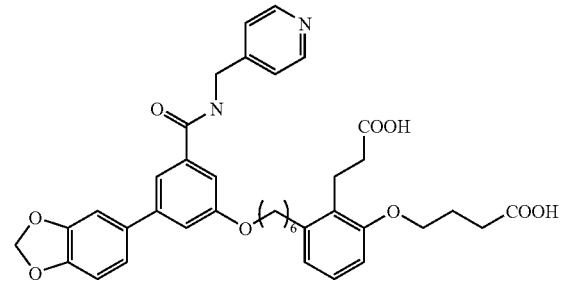

The title compound was prepared according to the general procedure described in Steps 7 and 8 of Method B starting from 3-benzo[1,3]dioxol-5-yl-5-hydroxy-N-pyridin-4-ylmethyl-benzamide.

HRMS calcd for $C_{39}H_{42}N_2O_9$ [M+H]$^+$ 683.2963, observed 683.2961

Example 55

4-[3-[6-(3-Benzo[1,3]dioxol-5-yl-5-carbamoyl-phenoxy)-hexyl]-2-(2-carboxy-ethyl)-phenoxy]-butyric acid

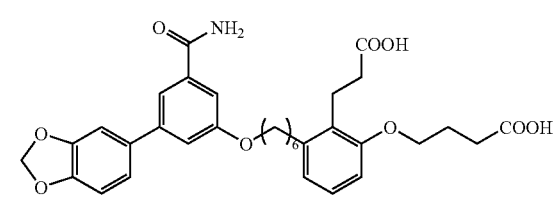

The title compound was prepared according to the general procedure described in Steps 7 and 8 of Method B starting from 3-benzo[1,3]dioxol-5-yl-5-hydroxy-benzamide.

HRMS calcd for $C_{33}H_{37}NO_9$ [M+H]$^+$ 592.2541, observed 592.2538

Example 56

4-[3-(6-{3-Benzo[1,3]dioxol-5-yl-5-[(pyridin-3-ylmethyl)-carbamoyl]-phenoxy}-hexyl)-2-(2-carboxyethyl)-phenoxy]-butyric acid

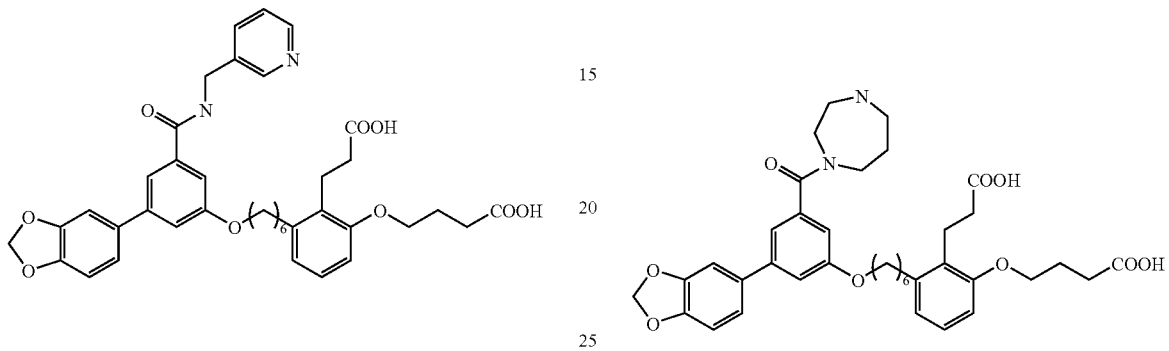

The title compound was prepared according to the general procedure described in Steps 7 and 8 of Method B starting from 3-benzo[1,3]dioxol-5-yl-5-hydroxy-N-pyridin-3-ylmethyl-benzamide.

HRMS calcd for $C_{39}H_{42}N_2O_9$ [M+H]$^+$ 683.2963, observed 683.296

Example 57

4-[3-{6-[3-Benzo[1,3]dioxol-5-yl-5-(3,3-dimethylpiperidine-1-carbonyl)-phenoxy]-hexyl}-2-(2-carboxy-ethyl)-phenoxy]-butyric acid

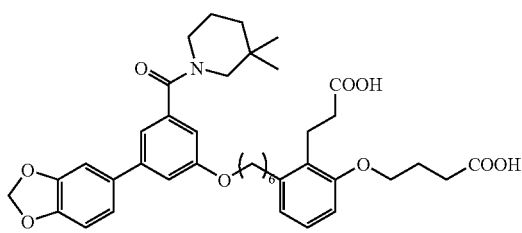

The title compound was prepared according to the general procedure described in Steps 7 and 8 of Method B starting from (3-benzo[1,3]dioxol-5-yl-5-hydroxy-phenyl)-(3,3-dimethyl-piperidin-1-yl)-methanone.

HRMS calcd for $C_{40}H_{49}NO_9$ [M+H]$^+$ 688.3480, observed 688.3481

Example 58

4-[3-{6-[3-Benzo[1,3]dioxol-5-yl-5-([1,4]diazepane-1-carbonyl)-phenoxy]-hexyl}-2-(2-carboxy-ethyl)-phenoxy]-butyric acid To a solution of 4-(3-benzo[1,3]dioxol-5-yl-5-hydroxy-benzoyl)-[1,4]diazepane-1-carboxylic acid tert-butyl ester (400 mg) in a mixture of acetone and DMF (2:1, 3 mL) were added potassium carbonate (10 eq.) and 4-[3-(6-bromo-hexyl)-2-(2-ethoxycarbonyl-ethyl)-phenoxy]-butyric acid ethyl ester (1.1 eq). The resulting mixture was stirred at 75° C. for 2 days. Then the insoluble material was filtered out and the filtrate was diluted with ethyl acetate and washed with water and brine. The organic extract was dried over anhydrous sodium sulfate, concentrated and purified on a silica gel column using ethyl acetate and hexanes to yield 4-(3-benzo[1,3]dioxol-5-yl-5-{6-[2-(2-ethoxycarbonyl-ethyl)-3-(3-ethoxycarbonyl-propoxy)-phenyl]-hexyloxy}-benzoyl)-[1,4]diazepane-1-carboxylic acid tert-butyl ester (556 mg). The total amount of material from the previous step was dissolved in EtOH (3 mL), followed by addition of 10 M NaOH solution (10 eq.). The resulting reaction mixture was stirred at room temperature for 3 h. Then it was neutralized with 3 N HCl and extracted into ethyl acetate. The organic extract was washed with water and brine and dried over anhydrous sodium sulfate. The crude material was concentrated under reduced pressure and redissolved in a mixture of TFA and dichloromethane (1:1, 2 mL) and stirred at room temperature for 2 h. The solvents were removed under reduced pressure and the crude material was purified on reverse-phase HPLC to yield the title compound.

HRMS calcd for $C_{38}H_{46}N_2O_9$ [M+H]$^+$ 675.3276, observed 675.3276

Example 59

4-[3-{6-[3-Benzo[1,3]dioxol-5-yl-5-(5-oxo-[1,4]diazepane-1-carbonyl)-phenoxy]-hexyl}-2-(2-carboxy-ethyl)-phenoxy]-butyric acid

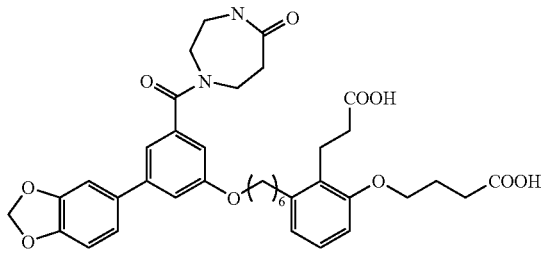

To a solution of 1-(3-benzo[1,3]dioxol-5-yl-5-hydroxy-benzoyl)-[1,4]diazepan-5-one (0.58 mmol) in a mixture of acetone and DMF (2:1, 2 mL) were added potassium carbonate (10 eq.) and 4-[3-(6-bromo-hexyl)-2-(2-ethoxycarbonyl-ethyl)-phenoxy]-butyric acid ethyl ester (1.1 eq). The resulting mixture was stirred at 75° C. for 2 days. Then the insoluble material was filtered out and the filtrate was diluted with ethyl acetate and washed with water and brine. The organic extract was dried over anhydrous sodium sulfate, concentrated and used for the next step without further purification. The total amount of material from the previous step was dissolved in 1,2-dichloroethane (4 mL), followed by addition of trimethyltin hydroxide (433 mg). The resulting reaction mixture was stirred at 70° C. for 7 days. Then it was neutralized with 5% HCl and extracted into ethyl acetate. The organic extract was washed with water and brine and dried over anhydrous sodium sulfate. The crude material was purified by reverse-phase HPLC to yield the title compound.

HRMS calcd for $C_{38}H_{44}N_2O_{10}$ [M+H]$^+$ 689.3069, observed 689.3066

Example 60

4-[3-{6-[3-Benzo[1,3]dioxol-5-yl-5-(benzyl-methyl-carbamoyl)-phenoxy]-hexyl}-2-(2-carboxy-ethyl)-phenoxy]-butyric acid

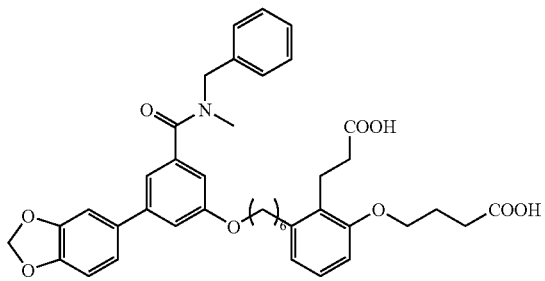

The title compound was prepared according to the general procedure described in Steps 7 and 8 of Method B starting from 3-benzo[1,3]dioxol-5-yl-N-benzyl-5-hydroxy-N-methyl-benzamide.

HRMS calcd for $C_{41}H_{45}NO_9$ [M+H]$^+$ 696.3167, observed 696.3163

Example 61

4-[3-[6-(3-Benzo[1,3]dioxol-5-yl-5-cyclobutylcarbamoyl-phenoxy)-hexyl]-2-(2-carboxy-ethyl)-phenoxy]-butyric acid

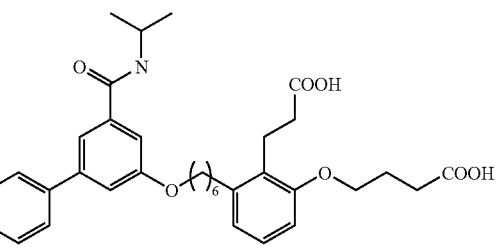

The title compound was prepared according to the general procedure described in Steps 7 and 8 of Method B starting from 3-benzo[1,3]dioxol-5-yl-N-cyclobutyl-5-hydroxy-benzamide.

HRMS calcd for $C_{37}H_{43}NO_9$ [M+H]$^+$ 646.3011, observed 646.3009

Example 62

4-[3-[6-(3-Benzo[1,3]dioxol-5-yl-5-isopropylcarbamoyl-phenoxy)-hexyl]-2-(2-carboxy-ethyl)-phenoxy]-butyric acid The title compound was prepared according to the general procedure described in Steps 7 and 8 of Method B starting from 3-benzo[1,3]dioxol-5-yl-5-hydroxy-N-isopropyl-benzamide.

HRMS calcd for $C_{36}H_{43}NO_9$ [M+H]$^+$ 634.3011, observed 634.3009

Example 63

4-[3-[6-(3-Benzo[1,3]dioxol-5-yl-5-cyclopentylcarbamoyl-phenoxy)-hexyl]-2-(2-carboxy-ethyl)-phenoxy]-butyric acid

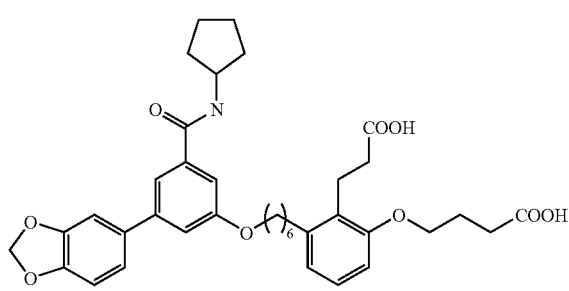

The title compound was prepared according to the general procedure described in Steps 7 and 8 of Method B starting from 3-benzo[1,3]dioxol-5-yl-N-cyclopentyl-5-hydroxy-benzamide.

HRMS calcd for $C_{38}H_{45}NO_9$ [M+H]$^+$ 660.3167, observed 660.3162

Example 64

4-[3-[6-(3-Benzo[1,3]dioxol-5-yl-5-cyclohexylcarbamoyl-phenoxy)-hexyl]-2-(2-carboxy-ethyl)-phenoxy]-butyric acid

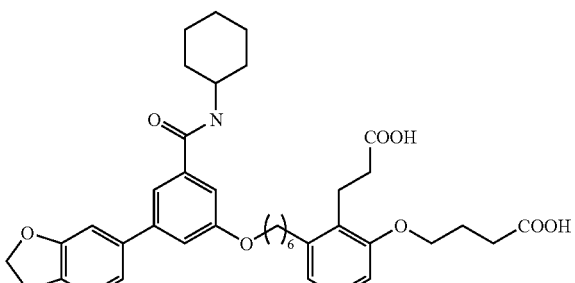

The title compound was prepared according to the general procedure described in Steps 7 and 8 of Method B starting from 3-benzo[1,3]dioxol-5-yl-N-cyclohexyl-5-hydroxy-benzamide.

HRMS calcd for $C_{39}H_{47}NO_9$ [M+H]$^+$ 674.3324, observed 674.3321

Method C

Step 1: 5-Benzyloxy-3'-fluoro-biphenyl-3-carboxylic acid methyl ester

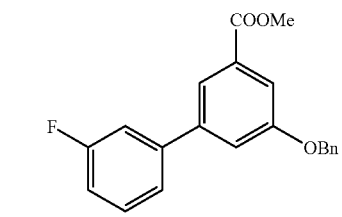

The title compound was prepared in the same way as 3-benzo[1,3]dioxol-5-yl-5-benzyloxy-benzoic acid methyl ester (described in Method B, step 3) from 3-benzyloxy-5-trifluoromethanesulfonyloxy-benzoic acid methyl ester and 3-fluorophenylboronic acid.

HRMS calcd for $C_{21}H_{17}FO_3$ [M+H]$^+$ 337.1235, observed 337.1234

Step 2: 5-Benzyloxy-3'-fluoro-biphenyl-3-carboxylic acid

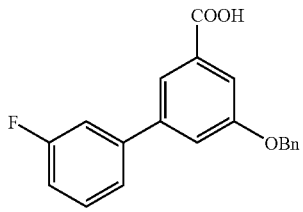

To a solution of 5-benzyloxy-3'-fluoro-biphenyl-3-carboxylic acid methyl ester (4.2 g) was added a solution of LiOH (2.9 g) in water (50 mL) and the resulting mixture was stirred at 55° C. overnight. The reaction mixture was acidified with 3 N HCl and the white precipitate was collected by filtration. It was washed with water and dried on air to yield the title compound (3.8 g, 94% yield).

HRMS calcd for $C_{20}H_{15}FO_3$ [M+Na]$^+$ 345.0897, observed 345.0898

Step 3 5-Benzyloxy-3'-fluoro-biphenyl-3-carboxylic acid tert-butyl ester

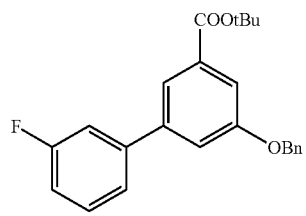

To a solution of 5-benzyloxy-3'-fluoro-biphenyl-3-carboxylic acid (3.8 g) in toluene (80 mL) was added N,N-dimethylformamide di-tert-butyl acetal (30 mL) and the reaction mixture was stirred at 85° C. for 3 h. Then the reaction mixture was diluted with ethyl acetate, washed with water and brine. The organic extract was concentrated under reduced pressure and purified in a silica gel column using ethyl acetate and hexanes to yield the title compound (4.1 g, 92% yield)

LRMS calcd for $C_{24}H_{23}FO_3$ [M+Na]$^+$ 401.2, observed 401.1

3-Benzo[1,3]dioxol-5-yl-5-benzyloxy-benzoic acid tert-butyl ester

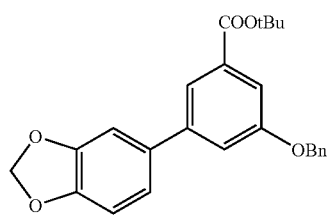

To a solution of 3-benzo[1,3]dioxol-5-yl-5-benzyloxy-benzoic acid (4.5 g) in toluene (80 mL) was added N,N-dimethylformamide di-tert-butyl acetal (38 mL) and the reaction mixture was stirred at 85° C. for 13 days. Then the reaction mixture was diluted with ethyl acetate, washed with water and brine. The organic extract was concentrated under reduced pressure and purified in a silica gel column using ethyl acetate and hexanes to yield the title compound (4.2 g, 80% yield)

HRMS calcd for $C_{25}H_{24}O_5$ [M+Na]$^+$ 427.1516, observed 427.1515

Step 4

3'-Fluoro-5-hydroxy-biphenyl-3-carboxylic acid tert-butyl ester

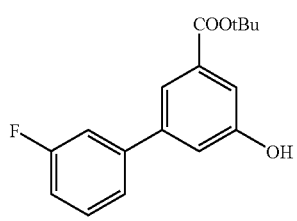

5-Benzyloxy-3'-fluoro-biphenyl-3-carboxylic acid tert-butyl ester (4.1 g) was dissolved in EtOH (50 mL) and hydrogenated in Parr apparatus over 10% Pd/C (410 mg) for 1 h. The catalyst was removed by filtration and the filtrate was concentrated under reduced pressure to yield the title compound (3.0 g, 96% yield).

HRMS calcd for $C_{17}H_{17}FO_3$ [M+Na]$^+$ 311.1054, observed 311.1052

3-Benzo[1,3]dioxol-5-yl-5-hydroxy-benzoic acid tert-butyl ester

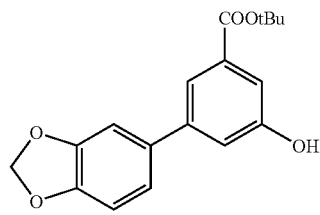

The title compound was prepared in the same way as 3'-fluoro-5-hydroxy-biphenyl-3-carboxylic acid tert-butyl ester starting from 3-benzo[1,3]dioxol-5-yl-5-benzyloxy-benzoic acid tert-butyl ester.

HRMS calcd for $C_{18}H_{18}FO_5$ [M+Na]$^+$ 337.1016, observed 337.1014

Step 5—5-{6-[2-(2-Ethoxycarbonyl-ethyl)-3-(3-ethoxycarbonyl-propoxy)-phenyl]-hexyloxy}-3'-fluoro-biphenyl-3-carboxylic acid tert-butyl ester

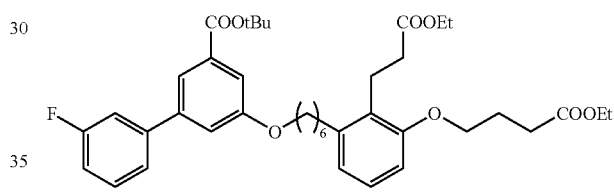

To a solution of 3'-fluoro-5-hydroxy-biphenyl-3-carboxylic acid tert-butyl ester (3.0 g) in a mixture of acetone and DMF (2:1, 100 mL) were added potassium carbonate (14.4 g) and 4-[3-(6-bromo-hexyl)-2-(2-ethoxycarbonyl-ethyl)-phenoxy]-butyric acid ethyl ester (5.4 g). The resulting mixture was stirred at 75° C. for 1 day. Then the insoluble material was filtered out and the filtrate was diluted with ethyl acetate and washed with water and brine. The organic extract was dried over anhydrous sodium sulfate, concentrated and purified on a silica gel column using ethyl acetate and hexanes to yield the title compound (7.1 g, 100% yield).

HRMS calcd for $C_{40}H_{51}FO_8$ [M+Na]$^+$ 701.3460, observed 701.3459

3-Benzo[1,3]dioxol-5-yl-5-{6-[2-(2-ethoxycarbonyl-ethyl)-3-(3-ethoxycarbonyl-propoxy)-phenyl]-hexyloxy}-benzoic acid tert-butyl ester

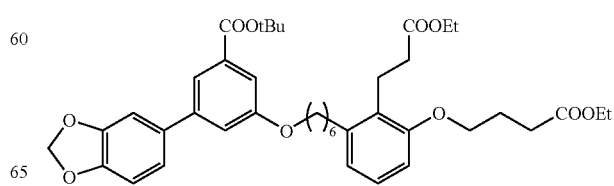

The title compound was prepared in the same way as 5-{6-[2-(2-ethoxycarbonyl-ethyl)-3-(3-ethoxycarbonyl-propoxy)-phenyl]-hexyloxy}-3'-fluoro-biphenyl-3-carboxylic acid tert-butyl ester starting from 3-benzo[1,3]dioxol-5-yl-5-hydroxy-benzoic acid tert-butyl ester.

HRMS calcd for $C_{41}H_{52}O_{10}$ [M+Na]$^+$ 727.3452, observed 727.3456

Step 6

5-{6-[2-(2-Ethoxycarbonyl-ethyl)-3-(3-ethoxycarbonyl-propoxy)-phenyl]-hexyloxy}-3'-fluoro-biphenyl-3-carboxylic acid

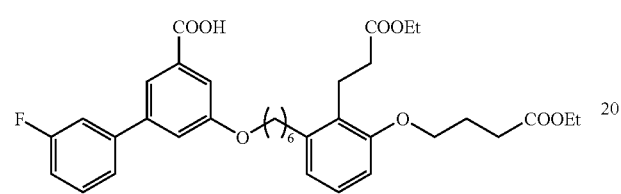

5-{6-[2-(2-Ethoxycarbonyl-ethyl)-3-(3-ethoxycarbonyl-propoxy)-phenyl]-hexyloxy}-3'-fluoro-biphenyl-3-carboxylic acid tert-butyl ester (7.0 g) was dissolved in a mixture of TFA and dichloromethane (1:1, 80 mL) and stirred at room temperature for 1 h. The solvents were removed under reduced pressure and the crude material was purified on a silica gel column using ethyl acetate and hexanes to yield the title compound (5.9 g, 90% yield).

HRMS calcd for $C_{36}H_{43}FO_8$ [M+Na]$^+$ 646.2834, observed 646.2833

3-Benzo[1,3]dioxol-5-yl-5-{6-[2-(2-ethoxycarbonyl-ethyl)-3-(3-ethoxycarbonyl-propoxy)-phenyl]-hexyloxy}-benzoic acid

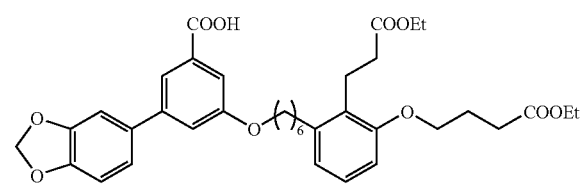

3-Benzo[1,3]dioxol-5-yl-5-{6-[2-(2-ethoxycarbonyl-ethyl)-3-(3-ethoxycarbonyl-propoxy)-phenyl]-hexyloxy}-benzoic acid tert-butyl ester (6.9 g) was dissolved in a mixture of TFA and dichloromethane (1:1, 50 mL) and stirred at room temperature overnight. The solvents were removed under reduced pressure and the crude material was purified on a silica gel column using ethyl acetate and hexanes to yield the title compound (6.3 g, 99% yield).

HRMS calcd for $C_{37}H_{44}O_{10}$ [M+Na]$^+$ 671.2826, observed 671.2822

Step 7 and 8

General Procedure:

The acid component, either 5-{6-[2-(2-ethoxycarbonyl-ethyl)-3-(3-ethoxycarbonyl-propoxy)-phenyl]-hexyloxy}-3'-fluoro-biphenyl-3-carboxylic acid or 3-benzo[1,3]dioxol-5-yl-5-{6-[2-(2-ethoxycarbonyl-ethyl)-3-(3-ethoxycarbonyl-propoxy)-phenyl]-hexyloxy}-benzoic acid (from 0.15 to 0.24 mmol), the appropriate amine (1.2 eq.), PyBroP (1.1 eq.), diisopropylethylamine (2 eq.) and dichloromethane (2 mL) were combined together and stirred at room temperature overnight. The reaction mixture was diluted with ethyl acetate and washed with water and brine. The organic extract was dried over anhydrous sodium sulfate and concentrated to dryness. The material was used without further purification for the next step. The total amount of the product obtained from the previous step was dissolved in ethanol (2 mL) and a 10 M NaOH solution was added (3 eq.). The resulting reaction mixture was stirred at room temperature for 5 h. Then it was neutralized with 3 N HCl and extracted into ethyl acetate. The organic extract was dried over anhydrous sodium sulfate and concentrated to dryness. The crude material was purified on reverse-phase HPLC to afford the title compound.

Example 65

4-{2-(2-Carboxy-ethyl)-3-[6-(5-dimethylcarbamoyl-3'-fluoro-biphenyl-3-yloxy)-hexyl]-phenoxy}-butyric acid

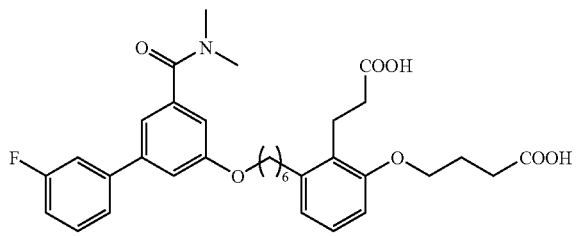

The title compound was prepared according to the general procedure described in Steps 7 and 8 of Method C starting from 5-{6-[2-(2-ethoxycarbonyl-ethyl)-3-(3-ethoxycarbonyl-propoxy)-phenyl]-hexyloxy}-3'-fluoro-biphenyl-3-carboxylic acid and dimethylamine (6% yield after two steps).

HRMS calcd for $C_{34}H_{40}FNO_7$ [M+H]$^+$ 594.2862, observed 594.2861

Example 66

4-{2-(2-Carboxy-ethyl)-3-[6-(5-cyclopropylcarbamoyl-3'-fluoro-biphenyl-3-yloxy)-hexyl]-phenoxy}-butyric acid

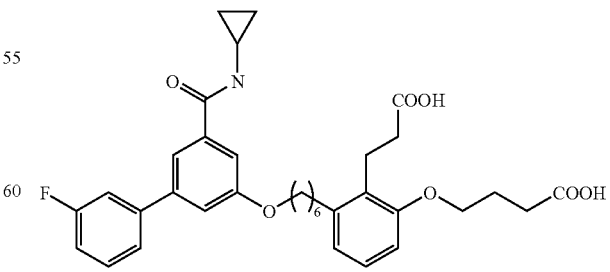

The title compound was prepared according to the general procedure described in Steps 7 and 8 of Method C starting from 5-{6-[2-(2-ethoxycarbonyl-ethyl)-3-(3-ethoxycarbonyl-propoxy)-phenyl]-hexyloxy}-3'-fluoro-biphenyl-3-carboxylic acid and cyclopropylamine (25% yield after two steps).

HRMS calcd for $C_{35}H_{40}FNO_7$ [M+H]$^+$ 606.2862, observed 606.2861

Example 67

4-{2-(2-Carboxy-ethyl)-3-[6-(5-cyclobutylcarbamoyl-3'-fluoro-biphenyl-3-yloxy)-hexyl]-phenoxy}-butyric acid

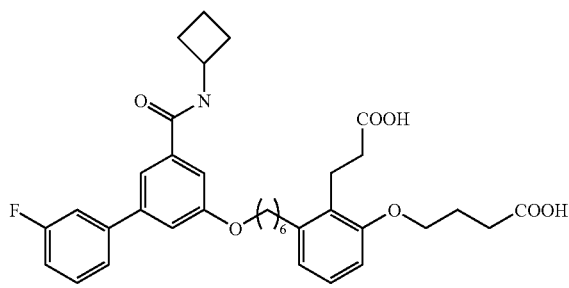

The title compound was prepared according to the general procedure described in Steps 7 and 8 of Method C starting from 5-{6-[2-(2-ethoxycarbonyl-ethyl)-3-(3-ethoxycarbonyl-propoxy)-phenyl]-hexyloxy}-3'-fluoro-biphenyl-3-carboxylic acid and cyclobutylamine (6% yield after two steps).

HRMS calcd for $C_{36}H_{42}FNO_7$ [M+H]$^+$ 620.3018, observed 620.3015

Example 68

4-(2-(2-Carboxy-ethyl)-3-{6-[3'-fluoro-5-(4-methyl-[1,4]diazepane-1-carbonyl)-biphenyl-3-yloxy]-hexyl}-phenoxy)-butyric acid

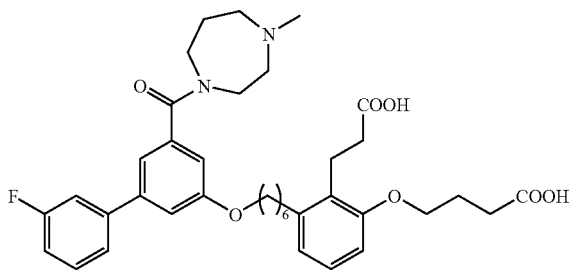

The title compound was prepared according to the general procedure described in Steps 7 and 8 of Method C starting from 5-{6-[2-(2-ethoxycarbonyl-ethyl)-3-(3-ethoxycarbonyl-propoxy)-phenyl]-hexyloxy}-3'-fluoro-biphenyl-3-carboxylic acid and 1-methyl-[1,4]diazepane (15% yield after two steps).

HRMS calcd for $C_{38}H_{47}FN_2O_7$ [M+H]$^+$ 663.3440, observed 663.3436

Example 69

4-(2-(2-Carboxy-ethyl)-3-{6-[3'-fluoro-5-(piperazine-1-carbonyl)-biphenyl-3-yloxy]-hexyl}-phenoxy)-butyric acid

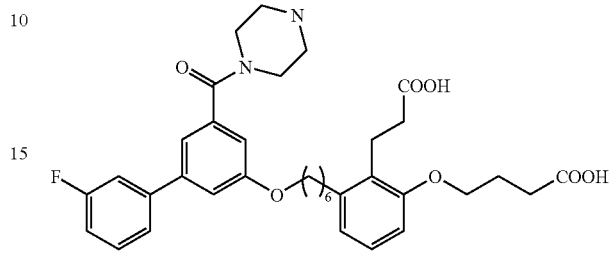

5-{6-[2-(2-Ethoxycarbonyl-ethyl)-3-(3-ethoxycarbonyl-propoxy)-phenyl]-hexyloxy}-3'-fluoro-biphenyl-3-carboxylic acid (150 mg), piperazine-1-carboxylic acid tert-butyl ester (54 mg), PyBroP (130 mg), diisopropylethylamine (85 □l) and dichloromethane (3 mL) were combined together and stirred at room temperature overnight. The reaction mixture was diluted with ethyl acetate and washed with water and brine. The organic extract was dried over anhydrous sodium sulfate and concentrated to dryness. The total amount of the product obtained from the previous step was dissolved in ethanol (2 mL) and 10 M NaOH solution was added (3 eq.). The resulting reaction mixture was stirred at room temperature for 5 h. Then it was neutralized with 3 N HCl and extracted into ethyl acetate. The organic extract was dried over anhydrous sodium sulfate, concentrated to dryness, redissolved in a mixture of TFA and dichloromethane (1:1, 2 mL) and stirred at room temperature for 3 h. The solvents were removed under reduced pressure and the title compound was purified on reverse-phase HPLC.

HRMS calcd for $C_{36}H_{43}FN_2O_7$ [M+H]$^+$ 635.3127, observed 635.3126

Example 70

4-(2-(2-Carboxy-ethyl)-3-{6-[5-([1,4]diazepane-1-carbonyl)-3'-fluoro-biphenyl-3-yloxy]-hexyl}-phenoxy)-butyric acid

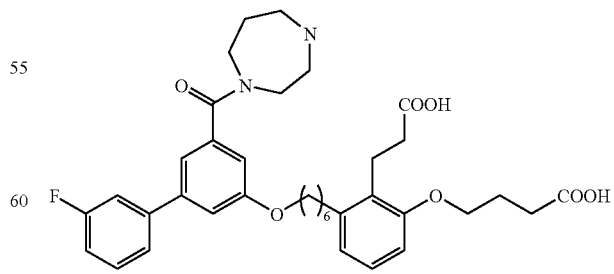

The title compound was prepared by the same method as 4-(2-(2-carboxy-ethyl)-3-{6-[3'-fluoro-5-(piperazine-1-carbonyl)-biphenyl-3-yloxy]-hexyl}-phenoxy)-butyric acid starting from 5-{6-[2-(2-ethoxycarbonyl-ethyl)-3-(3-ethoxy-carbonyl-propoxy)-phenyl]-hexyloxy}-3'-fluoro-biphenyl-3-carboxylic acid and [1,4]diazepane-1-carboxylic acid tert-butyl ester.

HRMS calcd for $C_{37}H_{45}FN_2O_7$ [M+H]$^+$ 649.3284, observed 649.3283

Example 71

4-{2-(2-Carboxy-ethyl)-3-[6-(3'-fluoro-5-methylcarbamoyl-biphenyl-3-yloxy)-hexyl]-phenoxy}-butyric acid

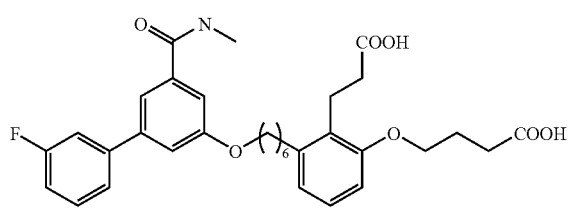

The title compound was prepared according to the general procedure described in Steps 7 and 8 of Method C starting from 5-{6-[2-(2-ethoxycarbonyl-ethyl)-3-(3-ethoxycarbonyl-propoxy)-phenyl]-hexyloxy}-3'-fluoro-biphenyl-3-carboxylic acid and methylamine.

HRMS calcd for $C_{33}H_{38}FNO_7$ [M+H]$^+$ 580.2705, observed 580.2704

Example 72

4-[3-[6-(3-Benzo[1,3]dioxol-5-yl-5-diethylcarbamoyl-phenoxy)-hexyl]-2-(2-carboxy-ethyl)-phenoxy]-butyric acid

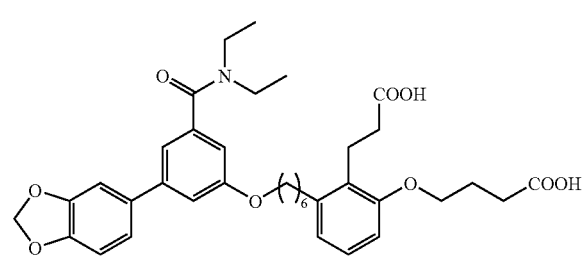

The title compound was prepared according to the general procedure described in Steps 7 and 8 of Method C starting from 3-benzo[1,3]dioxol-5-yl-5-{6-[2-(2-ethoxycarbonyl-ethyl)-3-(3-ethoxycarbonyl-propoxy)-phenyl]-hexyloxy}-benzoic acid and diethylamine.

HRMS calcd for $C_{37}H_{46}NO_9$ [M+H]$^+$ 648.3167, observed 648.3172

Example 73

4-[3-{6-[3-Benzo[1,3]dioxol-5-yl-5-(ethyl-methyl-carbamoyl)-phenoxy]-hexyl}-2-(2-carboxy-ethyl)-phenoxy]-butyric acid

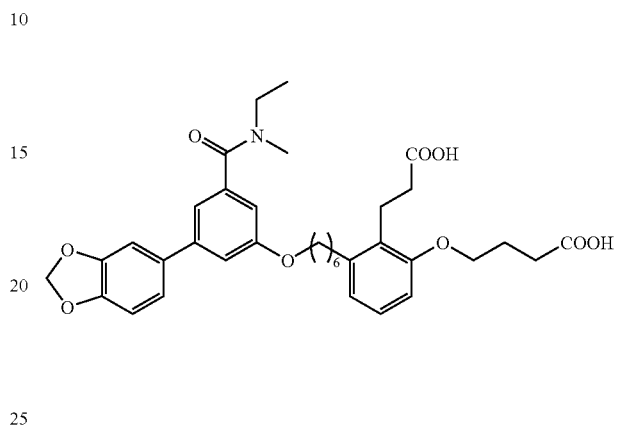

The title compound was prepared according to the general procedure described in Steps 7 and 8 of Method C starting from 3-benzo[1,3]dioxol-5-yl-5-{6-[2-(2-ethoxycarbonyl-ethyl)-3-(3-ethoxycarbonyl-propoxy)-phenyl]-hexyloxy}-benzoic acid and ethyl-methyl-amine.

HRMS calcd for $C_{36}H_{43}NO_9$ [M+H]$^+$ 634.3011, observed 634.301

Method D

Step 1: 3-Bromo-5-hydroxy-benzoic acid

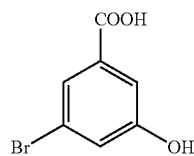

To a solution of NaOH (12.2 g; 305.8 mmol) in 300 mL of water was added 3-bromo-5-iodo-benzoic acid (20 g, 61.2 mmol) and Cu$_2$O (866 mg, 6.1 mmol). The reaction mixture was heated at 100° C. for 24 h. After complete consumption of the starting material, the reaction mixture was cooled to room temperature and filtered through Celite™. The filtrate was then acidified with 10% aq. HCl and extracted into ethyl acetate. The organic extract was dried over anhydrous sodium sulfate and concentrated under reduced pressure to afford the title compound as a tan solid (12.3 g, 93% yield).

HRMS calcd for $C_7H_5O_3Br$ [M–H]$^-$ 214.9349, observed 214.9350

Step 2: 3-Bromo-5-hydroxy-benzoic acid tert-butyl ester

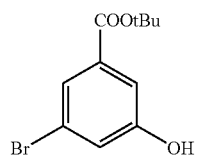

To a suspension of 3-bromo-5-hydroxy benzoic acid (2.0 g, 9.26 mmol) in toluene (20 mL) was slowly added N,N-dimethylformamide di-t-butyl acetal (10 mL, 40 mmol). The reaction mixture was heated at 80° C. for 14 h. Then the reaction mixture was cooled to room temperature and concentrated under reduced pressure. The crude material was purified by column chromatography (Isco™ 120 g) using 20% ethyl acetate/hexanes as eluting solvents to give the title compound (1.0 g, 40%) as a light yellow solid.

HRMS calcd for $C_{11}H_{13}O_3Br$ [M–H]⁻ 270.9975, observed 270.9975

Step 3: 3-Bromo-5-{6-[2-(2-ethoxycarbonyl-ethyl)-3-(3-ethoxycarbonyl-propoxy)-phenyl]-hexyloxy}-benzoic acid tert-butyl ester

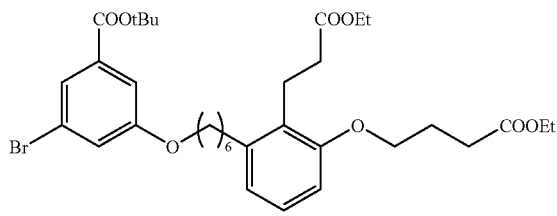

To a solution of 4-[3-(6-bromo-hexyl)-2-(2-ethoxycarbonyl-ethyl)-phenoxy]-butyric acid ethyl ester (9.48 g, 20.1 mmol), 3-bromo-5-hydroxy-benzoic acid tert-butyl ester (5.0 g, 18.3 mmol) in N,N-dimethylformamide (100 mL) and acetone (200 mL) was added potassium carbonate (25.3 g, 183 mmol) at room temperature. The resulting suspension was heated to 70° C. for 24 h. Then, the reaction mixture was cooled to room temperature and diluted with water and 10% aq. HCl. The organic compound was extracted into ethyl acetate and the combined organic extracts were washed with water and brine solution. The organic layers were dried over anhydrous sodium sulfate and removal of the solvent under reduced pressure gave the crude product which was purified on a silica gel column eluting with 0-20% ethyl acetate in hexanes to afford the title compound (12 g, 99%) as a colorless oil.

HRMS calcd for $C_{34}H_{47}O_8Br$ [M+Na]⁺ 685.2346, observed 685.2347

Step 4: 3-{6-[2-(2-Ethoxycarbonyl-ethyl)-3-(3-ethoxycarbonyl-propoxy)-phenyl]-hexyloxy}-5-thiophen-3-yl-benzoic acid tert-butyl ester

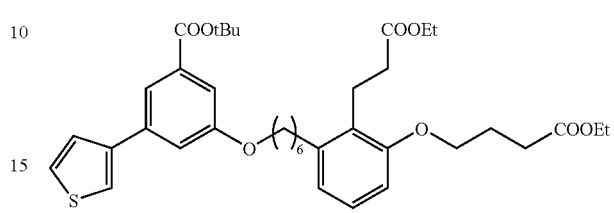

To a solution of 3-bromo-5-{6-[3-(2-ethoxycarbonyl-ethoxy)-2-(2ethoxycarbonyl-ethyl)-phenyl]-hexyloxy}-benzoic acid tert-butyl ester (2.0 g, 3.01 mmol) in DME (40 mL) were added 3-thiopheneboronic acid (957 mg, 7.5 mmol), cesium carbonate (2.44 g, 7.5 mmol) and $Pd(PPh_3)_4$ (200 mg, 0.17 mmol). The mixture was heated at 78° C. for 5 h and then cooled to room temperature. The reaction mixture was filtered through Celite™ and the filtrate was diluted with water and extracted into ethyl acetate. The organic phase was dried over anhydrous sodium sulfate and concentrated under reduced pressure. The crude oil was purified by using on a silica gel column, eluting with 0-30% ethyl acetate/hexanes to afford the title compound (1.6 g, 80%) as a light brown oil.

HRMS calcd for $C_{38}H_{50}O_8S$ (M+Na)⁺ 689.3118, observed 689.3120

3-{6-[2-(2-Ethoxycarbonyl-ethyl)-3-(3-ethoxycarbonyl-propoxy)-phenyl]-hexyloxy}-5-(4-methyl-thiophen-3-yl)-benzoic acid tert-butyl ester

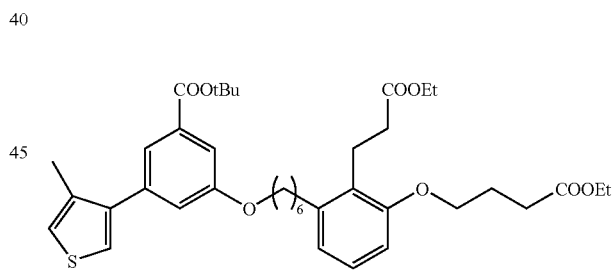

3-Bromo-5-{6-[2-(2-ethoxycarbonyl-ethyl)-3-(3-ethoxycarbonyl-propoxy)-phenyl]-hexyloxy}-benzoic acid tert-butyl ester (2.0 g) was dissolved in 1,2-dimethoxyethane (40 mL), followed by addition of $Pd(PPh_3)_4$ (80 mg), 2 M solution of sodium carbonate (6 mL) and 4-methyl-3-thiopheneboronic acid (641 mg). The resulting reaction mixture was stirred at 85° C. for 2 h. After cooling the reaction mixture was filtered through Celite™, diluted with ethyl acetate and washed with water and brine. The organic extract was dried over anhydrous sodium sulfate, concentrated under reduced pressure and purified on a silica gel column using ethyl acetate and hexanes to the title compound (1.8 g, 88% yield).

HRMS calcd for $C_{39}H_{52}O_8S$ [M+H]⁺ 681.3456, observed 681.3461

3-(2,3-Dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid tert-butyl ester

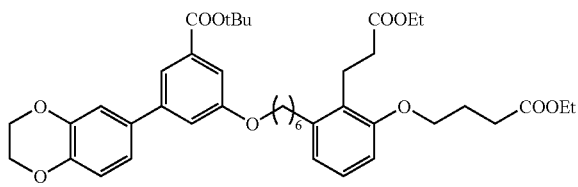

The title compound was prepared by the same method as 3-{6-[2-(2-ethoxycarbonyl-ethyl)-3-(3-ethoxycarbonyl-propoxy)-phenyl]-hexyloxy}-5-(4-methyl-thiophen-3-yl)-benzoic acid tert-butyl ester starting from 3-bromo-5-{6-[2-(2-ethoxycarbonyl-ethyl)-3-(3-ethoxycarbonyl-propoxy)-phenyl]-hexyloxy}-benzoic acid tert-butyl ester and 1,4-benzodioxane-6-boronic acid.

HRMS calcd for $C_{42}H_{54}O_{10}$ [M+Na]$^+$ 741.3609, observed 741.3604

Step 5

3-{6-[2-(2-Ethoxycarbonyl-ethyl)-3-(3-ethoxycarbonyl-propoxy)-phenyl]-hexyloxy}-5-thiophen-3-yl-benzoic acid

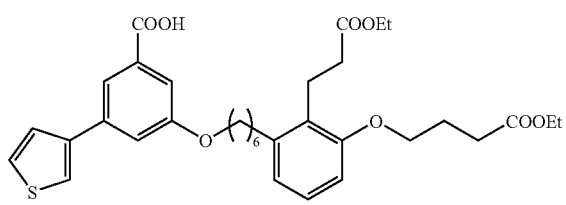

To a solution of 3-{6-[2-(2-ethoxycarbonyl-ethyl)-3-(3-ethoxycarbonyl-propoxy)-phenyl]-hexyloxy}-5-thiophen-3-yl-benzoic acid (1.5 g, 2.26 mmol) in dichloromethane (25 mL) was added trifluoroacetic acid (25 mL) at room temperature. The resulting light brown solution was stirred for 4 h. Then the dichloromethane and excess TFA was removed under reduced pressure to obtain the title compound (1.36 g, 100%) as a light brown oil.

HRMS calcd for $C_{34}H_{42}O_8S$ [M+Na]$^+$ 633.2492, observed 633.2490

3-{6-[2-(2-Ethoxycarbonyl-ethyl)-3-(3-ethoxycarbonyl-propoxy)-phenyl]-hexyloxy}-5-(4-methyl-thiophen-3-yl)-benzoic acid

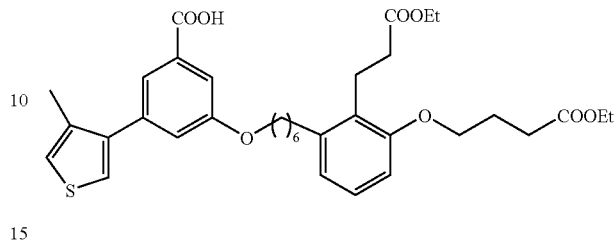

3-{6-[2-(2-Ethoxycarbonyl-ethyl)-3-(3-ethoxycarbonyl-propoxy)-phenyl]-hexyloxy}-5-(4-methyl-thiophen-3-yl)-benzoic acid tert-butyl ester (1.8 g) was dissolved in a mixture of TFA and dichloromethane (1:1, 20 mL) and stirred at room temperature for 1 h. The solvents were removed under reduced pressure and the crude material was purified on a silica gel column using ethyl acetate and hexanes to yield the title compound (1.2 g, 73% yield).

HRMS calcd for $C_{35}H_{44}O_8S$ [M+Na]$^+$ 647.2649, observed 647.2651

3-(2,3-Dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid

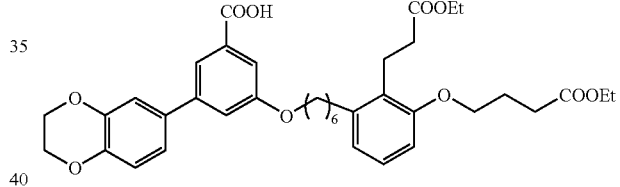

The title compound was prepared by the same method as 3-{6-[2-(2-ethoxycarbonyl-ethyl)-3-(3-ethoxycarbonyl-propoxy)-phenyl]-hexyloxy}-5-(4-methyl-thiophen-3-yl)-benzoic acid starting from 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid tert-butyl ester.

HRMS calcd for $C_{38}H_{46}O_{10}$ [M+Na]$^+$ 685.2983, observed 685.2981

Example 74

4-(2-(2-Carboxy-ethyl)-3-{6-[3-cyclopropylcarbamoyl-5-(4-methyl-thiophen-3-yl)-phenoxy]-hexyl}-phenoxy)-butyric acid General Procedure:

The acid component, 3-{6-[2-(2-ethoxycarbonyl-ethyl)-3-(3-ethoxycarbonyl-propoxy)-phenyl]-hexyloxy}-5-(4-methyl-thiophen-3-yl)-benzoic acid or 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid (0.15 mmol), the appropriate amine (1.2 eq.), PyBroP (1.1 eq.), diisopropylethylamine (2 eq.) and dichloromethane (2 mL) were combined together and stirred at room temperature overnight. The reaction mixture was diluted with ethyl acetate and washed with water and brine. The organic extract was dried over anhydrous sodium sulfate and concentrated to dryness. The material was used without further purification for the next step. The total amount of the product obtained from the previous step was dissolved in ethanol (2 mL) and a 10 M NaOH solution was added (3 eq.). The resulting reaction mixture was stirred at room temperature for 5 h. Then it was neutralized with 3 N HCl and extracted into ethyl acetate. The organic extract was dried over anhydrous sodium sulfate and concentrated to dryness. The crude material was purified on reverse-phase HPLC to afford the title compound.

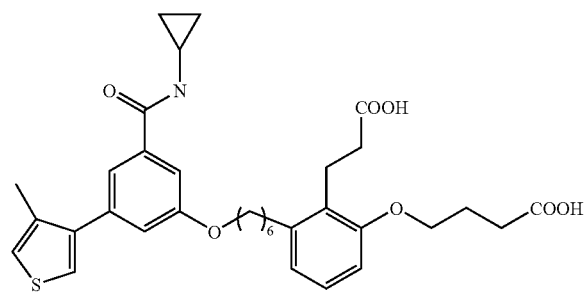

The title compound was prepared according to the general procedure described above starting from 3-{6-[2-(2-ethoxy-carbonyl-ethyl)-3-(3-ethoxycarbonyl-propoxy)-phenyl]-hexyloxy}-5-(4-methyl-thiophen-3-yl)-benzoic acid and cyclopropylamine (10% yield after two steps).

HRMS calcd for $C_{34}H_{41}NO_7S$ $[M+H]^+$ 608.2677, observed 608.2677

Example 75

4-(2-(2-Carboxy-ethyl)-3-{6-[3-diethylcarbamoyl-5-(4-methyl-thiophen-3-yl)-phenoxy]-hexyl}-phenoxy)-butyric acid

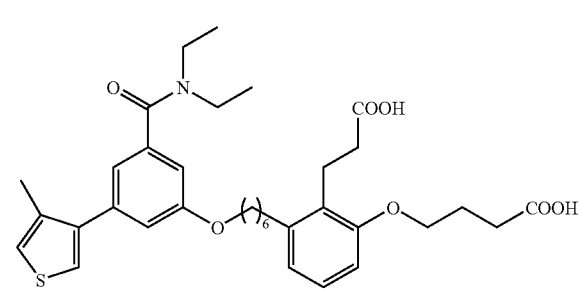

The title compound was prepared according to the general procedure described in Example 74 starting from 3-{6-[2-(2-ethoxycarbonyl-ethyl)-3-(3-ethoxycarbonyl-propoxy)-phenyl]-hexyloxy}-5-(4-methyl-thiophen-3-yl)-benzoic acid and diethylamine (24% yield after two steps).

HRMS calcd for $C_{35}H_{45}NO_7S$ $[M+H]^+$ 624.299, observed 624.299

Example 76

4-(2-(2-Carboxy-ethyl)-3-{6-[3-dimethylcarbamoyl-5-(4-methyl-thiophen-3-yl)-phenoxy]-hexyl}-phenoxy)-butyric acid The title compound was prepared according to the general procedure described in Example 74 starting from 3-{6-[2-(2-ethoxycarbonyl-ethyl)-3-(3-ethoxycarbonyl-propoxy)-phenyl]-hexyloxy}-5-(4-methyl-thiophen-3-yl)-benzoic acid and dimethylamine (27% yield after two steps).

HRMS calcd for $C_{33}H_{41}NO_7S$ $[M+H]^+$ 596.2677, observed 596.2677

Example 77

4-(2-(2-Carboxy-ethyl)-3-{6-[3-(2,3-dihydro-benzo[1,4]dioxin-6-yl)-5-methylcarbamoyl-phenoxy]-hexyl}-phenoxy)-butyric acid The title compound was prepared according to the general procedure described in Example 74 starting from 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid and methylamine.

HRMS calcd for $C_{35}H_{41}NO_9$ $[M+H]^+$ 620.2854, observed 620.285

Example 78

4-(2-(2-Carboxy-ethyl)-3-{6-[3-(2,3-dihydro-benzo[1,4]dioxin-6-yl)-5-isopropylcarbamoyl-phenoxy]-hexyl}-phenoxy)-butyric acid

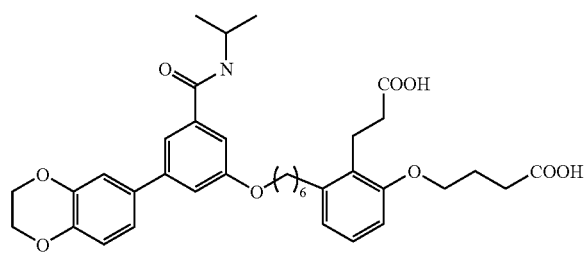

The title compound was prepared according to the general procedure described in Example 74 starting from 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid and isopropylamine.

HRMS calcd for $C_{37}H_{45}NO_9$ [M+H]$^+$ 648.3167, observed 648.3162

Example 79

4-(2-(2-Carboxy-ethyl)-3-{6-[3-(2,3-dihydro-benzo[1,4]dioxin-6-yl)-5-(morpholine-4-carbonyl)-phenoxy]-hexyl}-phenoxy)-butyric acid

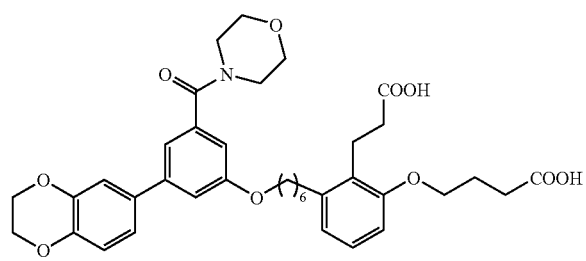

The title compound was prepared according to the general procedure described in Example 74 starting from 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid and morpholine.

HRMS calcd for $C_{38}H_{45}NO_{10}$ [M+Na]$^+$ 698.2935, observed 698.2933

Example 80

4-(2-(2-Carboxy-ethyl)-3-{6-[3-cyclopropylcarbamoyl-5-(2,3-dihydro-benzo[1,4]dioxin-6-yl)-phenoxy]-hexyl}-phenoxy)-butyric acid

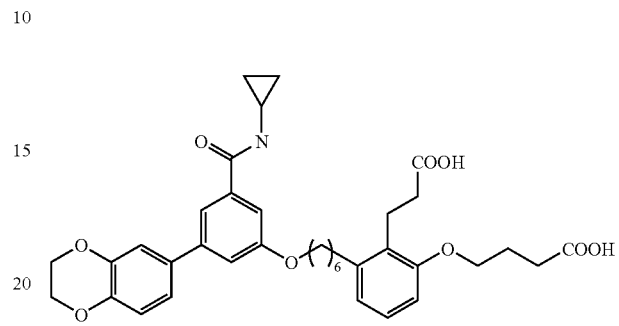

The title compound was prepared according to the general procedure described in Example 74 starting from 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid and cyclopropylamine.

HRMS calcd for $C_{37}H_{43}NO_9$ [M+H]$^+$ 646.3011, observed 646.3007

Example 81

4-(2-(2-Carboxy-ethyl)-3-{6-[3-diethylcarbamoyl-5-(2,3-dihydro-benzo[1,4]dioxin-6-yl)-phenoxy]-hexyl}-phenoxy)-butyric acid

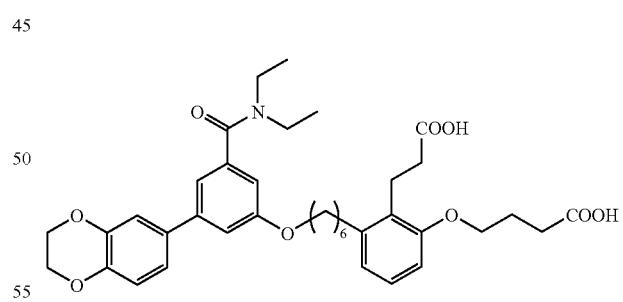

The title compound was prepared according to the general procedure described in Example 74 starting from 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid and diethylamine.

HRMS calcd for $C_{38}H_{47}NO_9$ [M+H]$^+$ 662.3324, observed 662.332

Example 82

4-(2-(2-Carboxy-ethyl)-3-{6-[3-(2,3-dihydro-benzo[1,4]dioxin-6-yl)-5-dimethylcarbamoyl-phenoxy]-hexyl}-phenoxy)-butyric acid

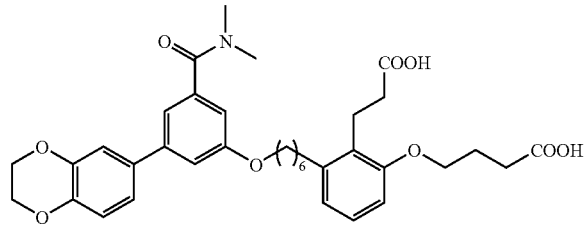

The title compound was prepared according to the general procedure described in Example 74 starting from 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid and dimethylamine.

HRMS calcd for $C_{36}H_{43}NO_9$ $[M+H]^+$ 634.3011, observed 634.3011

Example 83

4-[2-(2-Carboxy-ethyl)-3-(6-{3-(2,3-dihydro-benzo[1,4]dioxin-6-yl)-5-[2-(4-fluoro-phenyl)-ethylcarbamoyl]-phenoxy}-hexyl)-phenoxy]-butyric acid

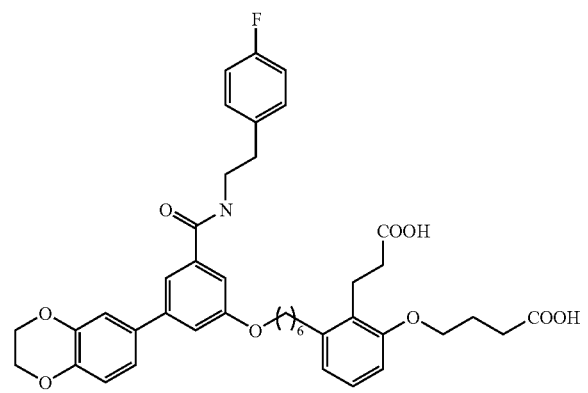

The title compound was prepared according to the general procedure described in Example 74 starting from 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid and 2-(4-fluoro-phenyl)-ethylamine.

HRMS calcd for $C_{42}H_{46}FNO_9$ $[M+H]^+$ 728.323, observed 728.3227

Example 84

4-(2-(2-Carboxy-ethyl)-3-{6-[3-(2,3-dihydro-benzo[1,4]dioxin-6-yl)-5-ethylcarbamoyl-phenoxy]-hexyl}-phenoxy)-butyric acid

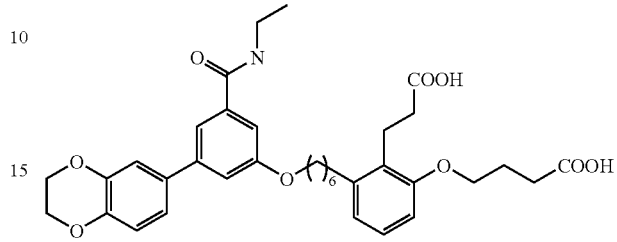

The title compound was prepared according to the general procedure described in Example 74 starting from 3-(2,3-dihydro-benzo[1,4]dioxin-6-yl)-5-{6-[2-(2-ethoxycarbonyl-ethyl)-3-(3-ethoxycarbonyl-propoxy)-phenyl]-hexyloxy}-benzoic acid and ethylamine.

HRMS calcd for $C_{36}H_{43}NO_9$ $[M+H]^+$ 634.3011, observed 634.3007

Example 85

4-{2-(2-Carboxy-ethyl)-3-[6-(3-dimethylcarbamoyl-5-thiophen-3-yl-phenoxy)-hexyl]-phenoxy}-butyric acid

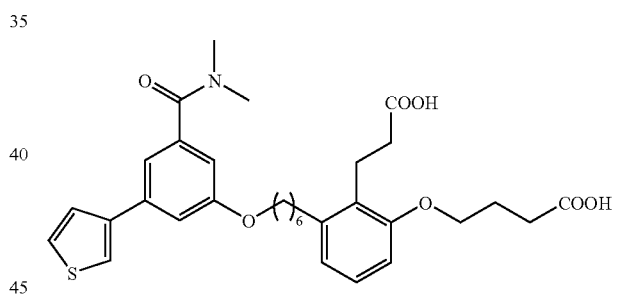

To a solution of 3-{6-[2-(2-ethoxycarbonyl-ethyl)-3-(3-ethoxycarbonyl-propoxy)-phenyl]-hexyloxy}-5-thiophen-3-yl-benzoic acid (130 mg, 0.21 mmol), PyBroP (263 mg, 0.63 mmol) and diisopropylethylamine (0.11 mL, 0.63 mmol) in $CH_2Cl_2$ (4 mL)/DMF (1 mL) was added dimethylamine hydrochloride (51 mg, 0.63 mmol). The reaction mixture was stirred at room temperature for 4 h. The reaction mixture was diluted with ethyl acetate and washed with brine. The organic extract was dried over anhydrous sodium sulfate and concentrated under reduced pressure. The total amount of the product obtained from the previous step was dissolved in ethanol (5 mL) and 1 M NaOH solution was added (2 mL) and the reaction mixture stirred for 3 h. Then the reaction mixture was diluted with ethyl acetate, washed with 10% aq. HCl and brine. The organic extract was dried over anhydrous sodium sulfate and concentrated under reduced pressure. The crude oil was purified by preparative HPLC using acetonitrile/water gradient to afford the title compound.

HRMS calcd for $C_{32}H_{39}NO_7S$ $[M+H]^+$ 582.2520, observed 582.2519

Example 86

4-{2-(2-Carboxy-ethyl)-3-[6-(3-cyclopropylcarbamoyl-5-thiophen-3-yl-phenoxy)-hexyl]-phenoxy}-butyric acid

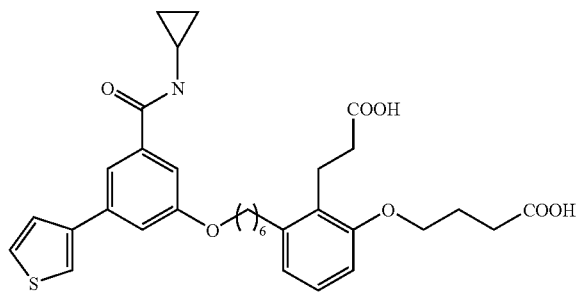

The title compound was prepared by the same method as 4-{2-(2-carboxy-ethyl)-3-[6-(3-dimethylcarbamoyl-5-thiophen-3-yl-phenoxy)-hexyl]-phenoxy}-butyric acid starting from 3-{6-[2-(2-ethoxycarbonyl-ethyl)-3-(3-ethoxycarbonyl-propoxy)-phenyl]-hexyloxy}-5-thiophen-3-yl-benzoic acid and cyclopropylamine.

HRMS calcd for $C_{33}H_{39}NO_7S$ [M+H]$^+$ 594.2520, observed 594.2521

Example 87

4-{2-(2-Carboxy-ethyl)-3-[6-(3-cyclobutylcarbamoyl-5-thiophen-3-yl-phenoxy)-hexyl]-phenoxy}-butyric acid

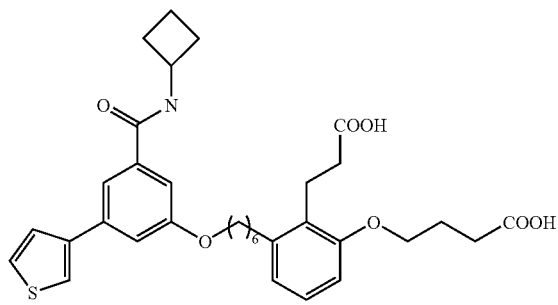

The title compound was prepared by the same method as 4-{2-(2-carboxy-ethyl)-3-[6-(3-dimethylcarbamoyl-5-thiophen-3-yl-phenoxy)-hexyl]-phenoxy}-butyric acid starting from 3-{6-[2-(2-ethoxycarbonyl-ethyl)-3-(3-ethoxycarbonyl-propoxy)-phenyl]-hexyloxy}-5-thiophen-3-yl-benzoic acid and cyclobutylamine.

HRMS calcd for $C_{34}H_{41}NO_7S$ [M+H]$^+$ 608.2677, observed 608.2679

Example 88

4-(2-(2-Carboxy-ethyl)-3-{6-[3-(piperidine-1-carbonyl)-5-thiophen-3-yl-phenoxy]-hexyl}-phenoxy)-butyric acid

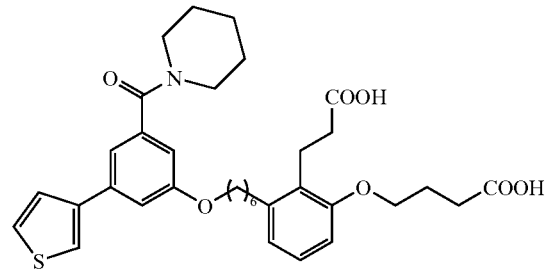

The title compound was prepared by the same method as 4-{2-(2-carboxy-ethyl)-3-[6-(3-dimethylcarbamoyl-5-thiophen-3-yl-phenoxy)-hexyl]-phenoxy}-butyric acid starting from 3-{6-[2-(2-ethoxycarbonyl-ethyl)-3-(3-ethoxycarbonyl-propoxy)-phenyl]-hexyloxy}-5-thiophen-3-yl-benzoic acid and piperidine.

HRMS calcd for $C_{35}H_{43}NO_7S$ [M+H]$^+$ 622.2833, observed 622.2833

Example 89

4-(2-(2-Carboxy-ethyl)-3-{6-[3-(4-hydroxy-piperidine-1-carbonyl)-5-thiophen-3-yl-phenoxy]-hexyl}-phenoxy)-butyric acid

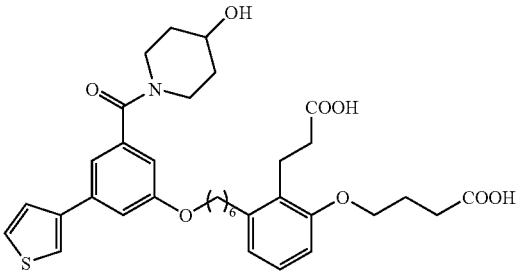

The title compound was prepared by the same method as 4-{2-(2-carboxy-ethyl)-3-[6-(3-dimethylcarbamoyl-5-thiophen-3-yl-phenoxy)-hexyl]-phenoxy}-butyric acid starting from 3-{6-[2-(2-ethoxycarbonyl-ethyl)-3-(3-ethoxycarbonyl-propoxy)-phenyl]-hexyloxy}-5-thiophen-3-yl-benzoic acid and 4-hydroxypiperidine.

HRMS calcd for $C_{35}H_{43}NO_8S$ [M+H]$^+$ 638.2782, observed 638.2782

Example 90

4-(2-(2-Carboxy-ethyl)-3-{6-[3-(cyclohexylmethyl-carbamoyl)-5-thiophen-3-yl-phenoxy]-hexyl}-phenoxy)-butyric acid

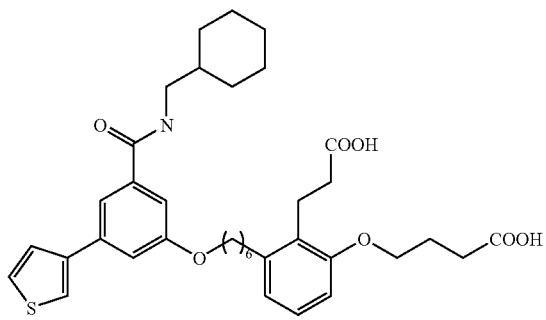

The title compound was prepared by the same method as 4-{2-(2-carboxy-ethyl)-3-[6-(3-dimethylcarbamoyl-5-thiophen-3-yl-phenoxy)-hexyl]-phenoxy}-butyric acid starting from 3-{6-[2-(2-ethoxycarbonyl-ethyl)-3-(3-ethoxycarbonyl-propoxy)-phenyl]-hexyloxy}-5-thiophen-3-yl-benzoic acid and cyclohexanemethylamine.

HRMS calcd for $C_{37}H_{47}NO_7S$ [M+Na]$^+$ 672.2965, observed 672.2963

Example 91

4-{2-(2-Carboxy-ethyl)-3-[6-(3-ethylcarbamoyl-5-thiophen-3-yl-phenoxy)-hexyl]-phenoxy}-butyric acid

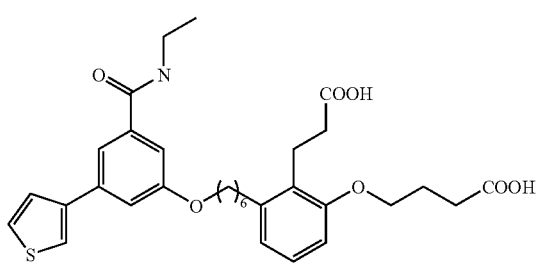

The title compound was prepared by the same method as 4-{2-(2-carboxy-ethyl)-3-[6-(3-dimethylcarbamoyl-5-thiophen-3-yl-phenoxy)-hexyl]-phenoxy}-butyric acid starting from 3-{6-[2-(2-ethoxycarbonyl-ethyl)-3-(3-ethoxycarbonyl-propoxy)-phenyl]-hexyloxy}-5-thiophen-3-yl-benzoic acid and ethylamine.

HRMS calcd for $C_{32}H_{39}NO_7S$ [M+Na]$^+$ 604.2339, observed 604.2341

Example 92

4-(2-(2-Carboxy-ethyl)-3-{6-[3-(piperazine-1-carbonyl)-5-thiophen-3-yl-phenoxy]-hexyl}-phenoxy)-butyric acid

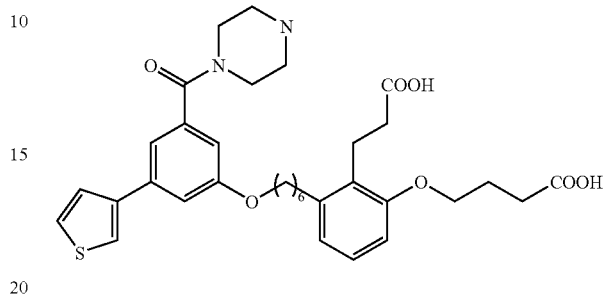

To a solution of 3-{6-[2-(2-ethoxycarbonyl-ethyl)-3-(3-ethoxycarbonyl-propoxy)-phenyl]-hexyloxy}-5-thiophen-3-yl-benzoic acid (130 mg, 0.21 mmol), PyBroP (263 mg, 0.63 mmol) and diisopropylethylamine (0.11 mL, 0.63 mmol) in $CH_2Cl_2$ (4 mL)/DMF (1 mL) was added piperazine-1-carboxylic acid tert-butyl ester (63 mg, 0.63 mmol). The reaction mixture was stirred at room temperature for 4 h. The reaction mixture was diluted with ethyl acetate and washed with brine. The organic extract was dried over anhydrous sodium sulfate and concentrated under reduced pressure. The total amount of the product obtained from the previous step was dissolved in ethanol (5 mL) and 1 M NaOH solution was added (2 mL) and the reaction mixture stirred for 3 h. Then the reaction mixture was diluted with ethyl acetate, washed with 10% aq. HCl and brine. The organic extract was dried over anhydrous sodium sulfate and concentrated under reduced pressure. The crude oil was dissolved in 5 mL $CH_2Cl_2$ and 5 mL of TFA was added. The reaction mixture was stirred for 1 h and the solvents were evaporated. The crude oil was purified by preparative HPLC using acetonitrile/water gradient to afford the title compound.

HRMS calcd for $C_{34}H_{42}N_2O_7S$ (M+H)$^+$ 623.2786, observed 623.2786

Example 93

4-(2-(2-carboxy-ethyl)-3-{6-[3-([1,4]diazepane-1-carbonyl)-5-thiophen-3-yl-phenoxy]-hexyl}-phenoxy)-butyric acid

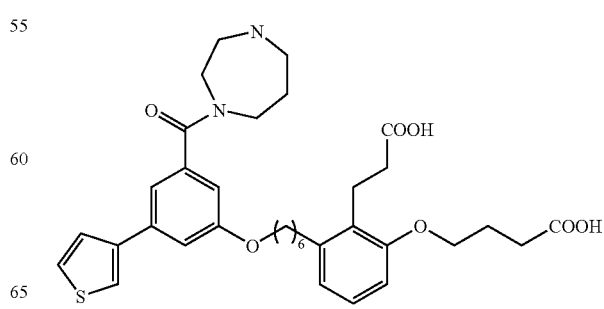

The title compound was prepared by the same method as 4-(2-(2-carboxy-ethyl)-3-{6-[3-(piperazine-1-carbonyl)-5-thiophen-3-yl-phenoxy]-hexyl}-phenoxy)-butyric acid starting from 3-{6-[2-(2-ethoxycarbonyl-ethyl)-3-(3-ethoxycarbonyl-propoxy)-phenyl]-hexyloxy}-5-thiophen-3-yl-benzoic acid and [1,4]diazepane-1-carboxylic acid tert-butyl ester.

HRMS calcd for $C_{35}H_{44}N_2O_7S$ [M+H]$^+$ 637.2942, observed 637.2941

Method E

Step 1: 3-bromo-5-{6-[2-(2-ethoxycarbonyl-ethyl)-3-(3-ethoxycarbonyl-propoxy)-phenyl]-hexyloxy}-benzoic acid

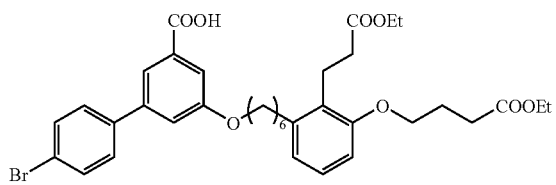

To a solution of 3-bromo-5-{6-[2-(2-ethoxycarbonyl-ethyl)-3-(3-ethoxycarbonyl-propoxy)-phenyl]-hexyloxy}-benzoic acid tert-butyl ester (2.3 g, 3.46 mmol) in dichloromethane (25 mL) was added trifluoroacetic acid (10 mL) at room temperature. The resulting light brown solution was stirred for 4 h. Then, the dichloromethane and excess TFA was removed under reduced pressure and the residue was dissolved in toluene and again removed under reduced pressure to remove all TFA to obtain 3-bromo-5-{6-[2-(2-ethoxycarbonyl-ethyl)-3-(3-ethoxycarbonyl-propoxy)-phenyl]-hexyloxy}-benzoic acid (2.1 g, 100%) as a light brown oil.

HRMS calcd for $C_{30}H_{39}O_8Br$ [M+Na]$^+$ 629.1720, observed 629.1725.

Step 2

4-{3-[6-(3-Bromo-5-dimethylcarbamoyl-phenoxy)-hexyl]-2-(2-ethoxycarbonyl-ethyl)-phenoxy}-butyric acid ethyl ester

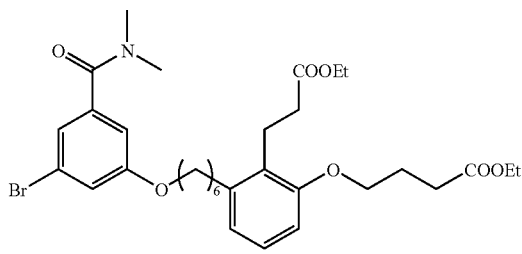

To a solution of 3-bromo-5-{6-[2-(2-ethoxycarbonyl-ethyl)-3-(3-ethoxycarbonyl-propoxy)-phenyl]-hexyloxy}-benzoic acid (808 mg, 1.33 mmol), bromotripyrrolidinophosphonium hexafluorophosphate (PyBroP) (745 mg, 1.6 mmol) in dichloromethane (15 mL) were added dimethylamine in THF (800 μL, 1.6 mmol, 2 M solution) and DIPEA (463 μL, 2.66 mmol) at room temperature. The resulting clear solution was stirred for 36 h. Then, the reaction mixture was diluted with water (100 mL) and dichloromethane (50 mL). The two layers were separated and the aqueous layer was extracted with dichloromethane (50 mL). The combined organic extracts were washed with brine solution (200 mL) and dried over anhydrous magnesium sulfate. Filtration of the drying agent and concentration of the filtrate in vacuo gave the crude product which was purified by using an ISCO™ (40 g) column chromatography eluting with 40-60% ethyl acetate in hexanes to afford 4-{3-[6-(3-bromo-5-dimethylcarbamoyl-phenoxy)-hexyl]-2-(2-ethoxycarbonyl-ethyl)-phenoxy}-butyric acid ethyl ester (757 mg, 90%) as a colorless oil HRMS calcd for $C_{32}H_{44}NO_7Br$ [M+Na]$^+$ 656.2193, observed 656.2199

4-[3-{6-[3-Bromo-5-(3,3-difluoro-pyrrolidine-1-carbonyl)-phenoxy]-hexyl}-2-(2-ethoxycarbonyl-ethyl)-phenoxy]-butyric acid ethyl ester

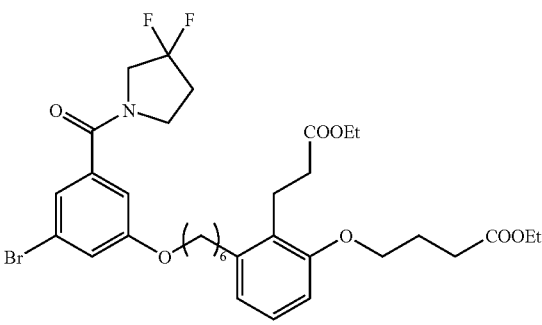

The title compound was prepared by the same method as 4-{3-[6-(3-bromo-5-dimethylcarbamoyl-phenoxy)-hexyl]-2-(2-ethoxycarbonyl-ethyl)-phenoxy}-butyric acid ethyl ester starting from 3-bromo-5-{6-[2-(2-ethoxycarbonyl-ethyl)-3-(3-ethoxycarbonyl-propoxy)-phenyl]-hexyloxy}-benzoic acid (550 mg, 0.905 mmol), PyBroP (508 mg, 1.09 mmol), 3,3-difluoropyrrolidine hydrochloride salt (156 mg, 1.09 mmol) and DIPEA (473 uL, 2.72 mmol) in dichloromethane (15 mL) to obtain 4-[3-{6-[3-bromo-5-(3,3-difluoro-pyrrolidine-1-carbonyl)-phenoxy]-hexyl}-2-(2-ethoxycarbonyl-ethyl)-phenoxy]-butyric acid ethyl ester (580 mg, 92%) as a colorless oil.

HRMS calcd for $C_{34}H_{44}NO_7F_2Br$ [M+H]$^+$ 696.2342, observed 696.2343

4-[3-{6-[3-Bromo-5-(2-difluoromethoxy-benzylcarbamoyl)-phenoxy]-hexyl}-2-(2-ethoxycarbonyl-ethyl)-phenoxy]-butyric acid ethyl ester

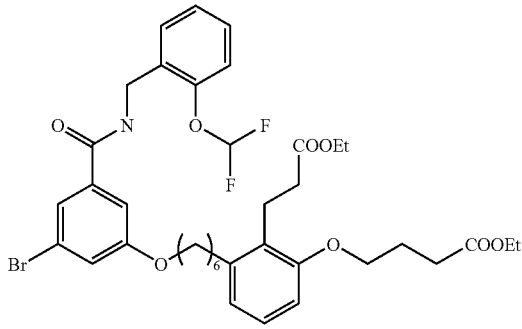

The title compound was prepared by the same method as 4-{3-[6-(3-bromo-5-dimethylcarbamoyl-phenoxy)-hexyl]-2-(2-ethoxycarbonyl-ethyl)-phenoxy}-butyric acid ethyl ester starting from 3-bromo-5-{6-[2-(2-ethoxycarbonyl-ethyl)-3-(3-ethoxycarbamoyl-propoxy)-phenyl]-hexyloxy}-benzoic acid (900 mg, 1.48 mmol), PyBroP (828 mg, 1.77 mmol), 2-(difluoromethoxy)-benzylamine (306 mg, 1.77 mmol) and DIPEA (515 uL, 2.96 mmol) in dichloromethane (30 mL) to obtain 4-[3-{6-[3-bromo-5-(2-difluoromethoxy-benzylcarbamoyl)-phenoxy]-hexyl}-2-(2-ethoxycarbonyl-ethyl)-phenoxy]-butyric acid ethyl ester (960 mg, 85%) as a colorless oil HRMS calcd for $C_{38}H_{46}NO_8F_2Br$ [M+Na]$^+$ 784.2267, observed 784.2262

Step 3

4-{3-[6-(5-Dimethylcarbamoyl-3',4'-difluoro-biphenyl-3-yloxy)-hexyl]-2-(2-ethoxycarbonyl-ethyl)-phenoxy}-butyric acid ethyl ester

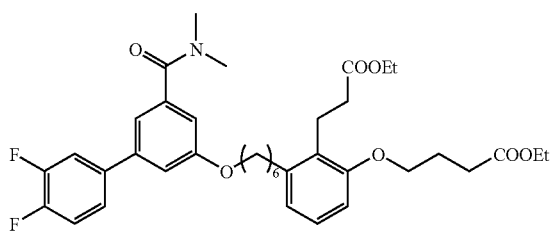

To a mixture of 4-{3-[6-(3-bromo-5-dimethylcarbamoyl-phenoxy)-hexyl]-2-(2-ethoxycarbonyl-ethyl)-phenoxy}-butyric acid ethyl ester (150 mg, 0.236 mmol), 3,4-difluorophenylboronic acid (75 mg, 0.472 mmol), PdCl$_2$(dppf) (29 mg, 0.04 mmol) and cesium carbonate (153 mg, 0.472 mmol) was added dimethoxyethane (5 mL) at room temperature under nitrogen atmosphere. The resulting light brown suspension was heated to 97° C. and stirred for 15 h. Then, the reaction mixture was cooled to room temperature and diluted with water (50 mL). The organic compound was extracted into ethyl acetate (2×50 mL) and the combined organic extracts were washed with brine solution (50 mL). The organic layer was dried over anhydrous magnesium sulfate, filtration of the drying agent and removal of the solvent under vacuum gave the crude dark brown residue which was purified by using an ISCO™ (40 g) column chromatography eluting with 30-60% ethyl acetate in hexanes to afford 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester (152 mg, 97%) as a colorless oil HRMS calcd for $C_{38}H_{47}NO_7F_2$ [M+Na]$^+$ 690.3213, observed 690.3219

4-{3-[6-(5-dimethylcarbamoyl-4'-fluoro-3'-hydroxy-biphenyl-3-yloxy)-hexyl]-2-(2-ethoxycarbonyl-ethyl)-phenoxy}-butyric acid ethyl ester

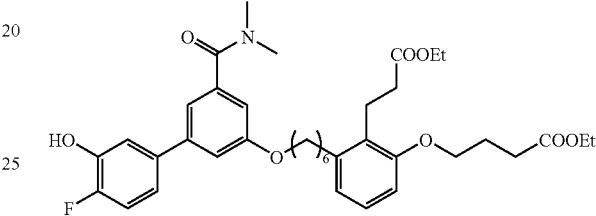

The title compound was prepared by the same method as 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester starting from 4-{3-[6-(3-bromo-5-dimethylcarbamoyl-phenoxy)-hexyl]-2-(2-ethoxycarbonyl-ethyl)-phenoxy}-butyric acid ethyl ester (150 mg, 0.236 mmol), 4-fluoro-3-hydroxyphenylboronic acid (74 mg, 0.472 mmol), PdCl$_2$(dppf) (29 mg, 0.04 mmol) and cesium carbonate (153 mg, 0.472 mmol) in dimethoxyethane (5 mL) to obtain 4-{3-[6-(5-dimethylcarbamoyl-4'-fluoro-3'-hydroxy-biphenyl-3-yloxy)-hexyl]-2-(2-ethoxycarbonyl-ethyl)-phenoxy}-butyric acid ethyl ester (150 mg, 95%) as a colorless oil.

HRMS calcd for $C_{38}H_{48}NO_8F$ [M+Na]$^+$ 688.3256, observed 688.3258

4-[3-{6-[3-benzo[1,3]dioxol-5-yl-5-(3,3-difluoro-pyrrolidine-1-carbonyl)-phenoxy]-hexyl}-2-(2-ethoxycarbonyl-ethyl)-phenoxy]-butyric acid ethyl ester

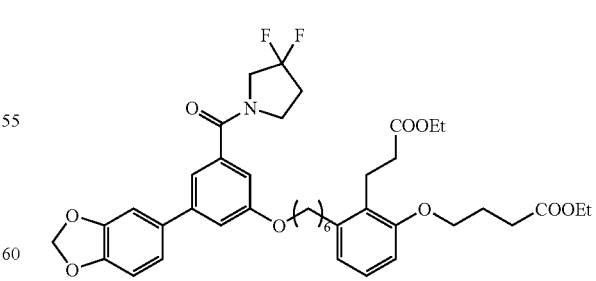

The title compound was prepared by the same method as 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester starting from 4-[3-{6-[3-bromo-5-(3,3-difluoro-pyrrolidine-1-carbonyl)-phenoxy]-hexyl}-2-(2- ethoxycarbonyl-ethyl)-phenoxy]-butyric acid ethyl ester (150 mg, 0.215 mmol), 3,4-methylenedioxyphenylboronic acid (73.56 mg, 0.43 mmol), PdCl$_2$(dppf) (23.6 mg, 0.03 mmol) and cesium carbonate (141.5 mg, 0.43 mmol) in 1,2-dimethoxyethane (5.0 mL) to obtain 4-[3-{6-[3-benzo[1,3]dioxol-5-yl-5-(3,3-difluoro-pyrrolidine-1-carbonyl)-phenoxy]-hexyl}-2-(2-ethoxycarbonyl-ethyl)-phenoxy]-butyric acid ethyl ester (127 mg, 80%) as a colorless oil LRMS calcd for C$_{41}$H$_{49}$NO$_9$F$_2$ [M+H$_2$O]$^+$ 755.3, observed 755.3

4-[3-{6-[5-(3,3-difluoro-pyrrolidine-1-carbonyl)-biphenyl-3-yloxy]-hexyl}-2-(2-ethoxycarbonyl-ethyl)-phenoxy]-butyric acid ethyl ester

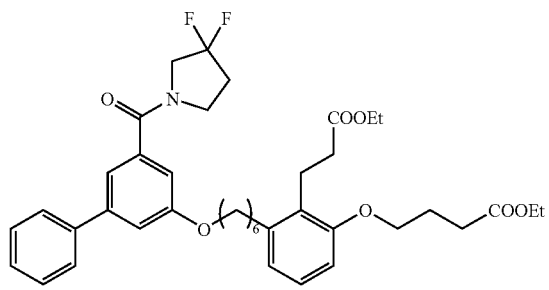

The title compound was prepared by the same method as 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester starting from 4-[3-{6-[3-bromo-5-(3,3-difluoro-pyrrolidine-1-carbonyl)-phenoxy]-hexyl}-2-(2-ethoxycarbonyl-ethyl)-phenoxy]-butyric acid ethyl ester (135 mg, 0.194 mmol), phenylboronic acid (48.27 mg, 0.388 mmol), PdCl$_2$(dppf) (21.24 mg, 0.03 mmol) and cesium carbonate (127.3 mg, 0.388 mmol) in 1,2-dimethoxyethane (5.0 mL) to obtain 4-[3-{6-[5-(3,3-difluoro-pyrrolidine-1-carbonyl)-biphenyl-3-yloxy]-hexyl}-2-(2-ethoxycarbonyl-ethyl)-phenoxy]-butyric acid ethyl ester (78 mg, 58%) as a colorless oil.

HRMS calcd for C$_{40}$H$_{49}$NO$_7$F$_2$ [M+H]$^+$ 694.3550, observed 694.3543

4-[3-{6-[3-(3,3-difluoro-pyrrolidine-1-carbonyl)-5-thiophen-3-yl-phenoxy]-hexyl}-2-(2-ethoxycarbonyl-ethyl)-phenoxy]-butyric acid ethyl ester

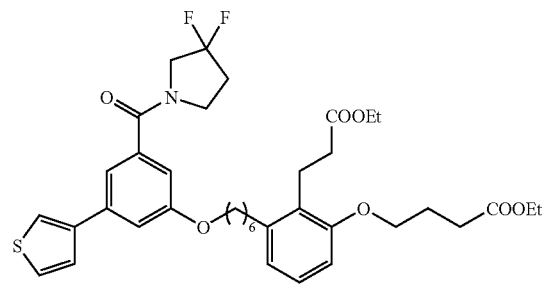

The title compound was prepared by the same method as 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester starting from 4-[3-{6-[3-bromo-5-(3,3- difluoro-pyrrolidine-1-carbonyl)-phenoxy]-hexyl}-2-(2-ethoxycarbonyl-ethyl)-phenoxy]-butyric acid ethyl ester (114 mg, 0.163 mmol), thiophen-3-ylboronic acid (42.57 mg, 0.326 mmol), PdCl$_2$(dppf) (17.94 mg, 0.025 mmol) and cesium carbonate (107.5 mg, 0.326 mmol) in dimethoxyethane (3.7 mL) to obtain 4-[3-{6-[3-(3,3-difluoro-pyrrolidine-1-carbonyl)-5-thiophen-3-yl-phenoxy]-hexyl}-2-(2-ethoxycarbonyl-ethyl)-phenoxy]-butyric acid ethyl ester (90 mg, 79%) as a colorless oil.

HRMS calcd for C$_{38}$H$_{47}$NO$_7$SF$_2$ [M+H]$^+$ 700.3114, observed 700.3114

4-[3-{6-[5-(3,3-difluoro-pyrrolidine-1-carbonyl)-3'-fluoro-biphenyl-3-yloxy]-hexyl}-2-(2-ethoxycarbonyl-ethyl)-phenoxy]-butyric acid ethyl ester

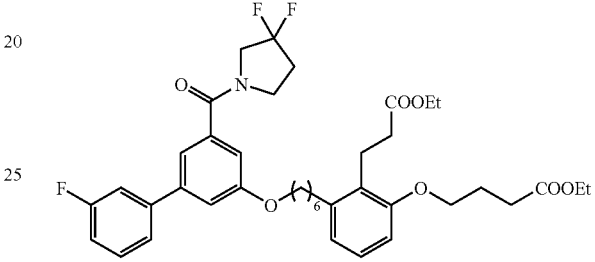

The title compound was prepared by the same method as 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester starting from 4-[3-{6-[3-bromo-5-(3,3-difluoro-pyrrolidine-1-carbonyl)-phenoxy]-hexyl}-2-(2-ethoxycarbonyl-ethyl)-phenoxy]-butyric acid ethyl ester (112 mg, 0.16 mmol), 3-fluorophenylboronic acid (45.23 mg, 0.32 mmol), PdCl$_2$(dppf) (17.63 mg, 0.024 mmol) and cesium carbonate (105.6 mg, 0.32 mmol) in 1,2-dimethoxyethane (5.0 mL) to obtain 4-[3-{6-[5-(3,3-difluoro-pyrrolidine-1-carbonyl)-3'-fluoro-biphenyl-3-yloxy]-hexyl}-2-(2-ethoxycarbonyl-ethyl)-phenoxy]-butyric acid ethyl ester (111 mg, 97%) as a colorless oil.

HRMS calcd for C$_{40}$H$_{48}$NO$_7$F$_3$ [M+H]$^+$ 712.3456, observed 712.3451

4-[3-{6-[5-(2-difluoromethoxy-benzylcarbamoyl)-biphenyl-3-yloxy]-hexyl}-2-(2-ethoxycarbonyl-ethyl)-phenoxy]-butyric acid ethyl ester

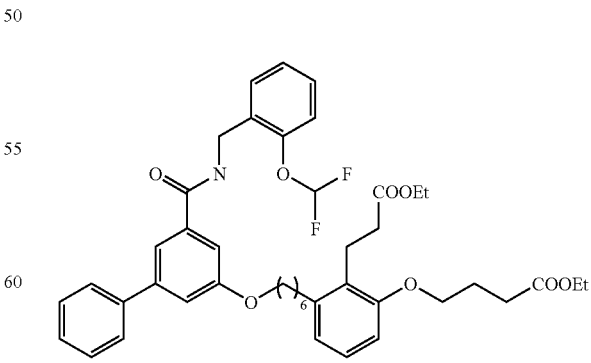

The title compound was prepared by the same method as 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester starting from 4-[3-{6-[3-bromo-5-(2-difluoromethoxy-benzylcarbamoyl)-phenoxy]-hexyl}-2-(2-ethoxycarbonyl-ethyl)-phenoxy]-butyric acid ethyl ester (200 mg, 0.262 mmol), phenylboronic acid (65 mg, 0.524 mmol), PdCl$_2$(dppf) (29 mg, 0.04 mmol) and cesium carbonate (171 mg, 0.524 mmol) in 1,2-dimethoxyethane (5.0 mL) to obtain 4-[3-{6-[5-(2-difluoromethoxy-benzylcarbamoyl)-biphenyl-3-yloxy]-hexyl}-2-(2-ethoxycarbonyl-ethyl)-phenoxy]-butyric acid ethyl ester (191 mg, 96%) as a colorless oil. HRMS calcd for C$_{44}$H$_{51}$NO$_8$F$_2$ [M+H]$^+$ 760.3656, observed 760.3651

4-[3-{6-[3-benzo[1,3]dioxol-5-yl-5-(2-difluoromethoxy-benzylcarbamoyl)-phenoxy]-hexyl}-2-(2-ethoxycarbonyl-ethyl)-phenoxy]-butyric acid ethyl ester

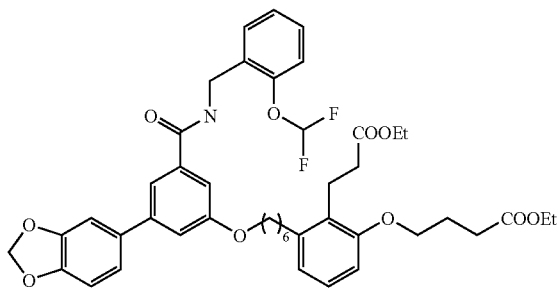

The title compound was prepared by the same method as 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester starting from 4-[3-{6-[3-bromo-5-(2-difluoromethoxy-benzylcarbamoyl)-phenoxy]-hexyl}-2-(2-ethoxycarbonyl-ethyl)-phenoxy]-butyric acid ethyl ester (200 mg, 0.262 mmol), 3,4-methylenedioxyphenylboronic acid (87 mg, 0.524 mmol), PdCl$_2$(dppf) (29 mg, 0.04 mmol) and cesium carbonate (171 mg, 0.524 mmol) in 1,2-dimethoxyethane (5.0 mL) to obtain 4-[3-{6-[3-benzo[1,3]dioxol-5-yl-5-(2-difluoromethoxy-benzylcarbamoyl)-phenoxy]-hexyl}-2-(2-ethoxycarbonyl-ethyl)-phenoxy]-butyric acid ethyl ester (184 mg, 88%) as a colorless oil.
HRMS calcd for C$_{45}$H$_{51}$NO$_{10}$F$_2$ [M+Na]$^+$ 826.3373, observed 826.3368

4-[3-{6-[5-(2-difluoromethoxy-benzylcarbamoyl)-2'-fluoro-biphenyl-3-yloxy]-hexyl}-2-(2-ethoxycarbonyl-ethyl)-phenoxy]-butyric acid ethyl ester

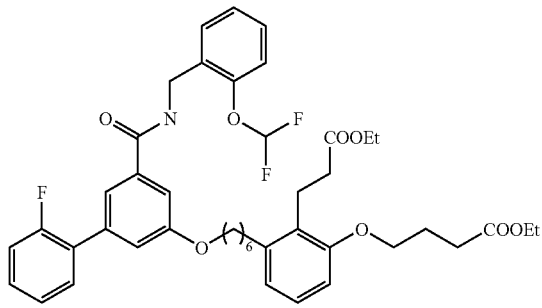

The title compound was prepared by the same method as 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester starting from 4-[3-{6-[3-bromo-5-(2-difluoromethoxy-benzylcarbamoyl)-phenoxy]-hexyl}-2-(2-ethoxycarbonyl-ethyl)-phenoxy]-butyric acid ethyl ester (150 mg, 0.196 mmol), 2-fluoro-phenylboronic acid (55 mg, 0.392 mmol), PdCl$_2$(dppf) (29 mg, 0.04 mmol) and cesium carbonate (128 mg, 0.392 mmol) in 1,2-dimethoxyethane (5.0 mL) to obtain 4-[3-{6-[5-(2-difluoromethoxy-benzylcarbamoyl)-2'-fluoro-biphenyl-3-yloxy]-hexyl}-2-(2-ethoxycarbonyl-ethyl)-phenoxy]-butyric acid ethyl ester (128 mg, 84%) as a colorless oil.

HRMS calcd for C$_{44}$H$_{50}$NO$_8$F$_3$ [M+Na]$^+$ 800.3381, observed 800.3378

4-[3-{6-[3-(2-difluoromethoxy-benzylcarbamoyl)-5-thiophen-3-yl-phenoxy]-hexyl}-2-(2-ethoxycarbonyl-ethyl)-phenoxy]-butyric acid ethyl ester

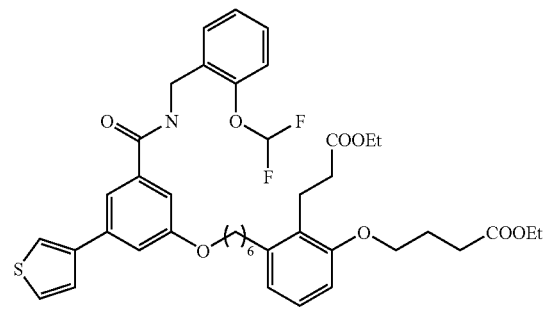

The title compound was prepared by the same method as 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester starting from 4-[3-{6-[3-bromo-5-(2-difluoromethoxy-benzylcarbamoyl)-phenoxy]-hexyl}-2-(2-ethoxycarbonyl-ethyl)-phenoxy]-butyric acid ethyl ester (200 mg, 0.262 mmol), 3-thiophenylboronic acid (67 mg, 0.524 mmol), PdCl$_2$(dppf) (29 mg, 0.04 mmol) and cesium carbonate (171 mg, 0.524 mmol) in 1,2-dimethoxyethane (5.0 mL) to obtain 4-[3-{6-[3-(2-difluoromethoxy-benzylcarbamoyl)-5-thiophen-3-yl-phenoxy]-hexyl}-2-(2-ethoxycarbonyl-ethyl)-phenoxy]-butyric acid ethyl ester (182 mg, 91%) as a colorless oil.

HRMS calcd for C$_{42}$H$_{49}$NO$_8$SF$_2$ [M+Na]$^+$ 788.3039, observed 788.3037

Example 94

4-{2-(2-Carboxy-ethyl)-3-[6-(5-dimethylcarbamoyl-3',4'-difluoro-biphenyl-3-yloxy)-hexyl]-phenoxy}-butyric acid

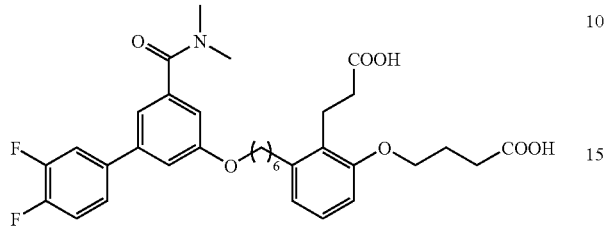

To a solution of 4-{3-[6-(5-dimethylcarbamoyl-3',4'-difluoro-biphenyl-3-yloxy)-hexyl]-2-(2-ethoxycarbonyl-ethyl)-phenoxy}-butyric acid ethyl ester (143 mg, 0.214 mmol) in THF (5 mL) and ethanol (5 mL) was added aqueous 1.0 N sodium hydroxide (5 mL) at room temperature. The mixture was stirred for 7 h at room temperature. Then, the reaction mixture was concentrated, the residue was diluted with water (20 mL) and extracted with diethyl ether (50 mL) to remove any neutral impurities. The aqueous layer was acidified with 1 N hydrochloric acid and the organic compound was extracted into ethyl acetate (2×50 mL). The combined organic extracts were washed with brine solution (50 mL) and dried over anhydrous magnesium sulfate. Filtration of the drying agent and removal of the solvent under vacuum gave 4-{2-(2-carboxy-ethyl)-3-[6-(5-dimethylcarbamoyl-3',4'-difluoro-biphenyl-3-yloxy)-hexyl]-phenoxy}-butyric acid (125 mg, 95%) as a white amorphous solid.

HRMS calcd for $C_{34}H_{39}NO_7F_2$ [M+Na]$^+$ 634.2587, observed 634.2591

Example 95

4-{2-(2-carboxy-ethyl)-3-[6-(5-dimethylcarbamoyl-4'-fluoro-3'-hydroxy-biphenyl-3-yloxy)-hexyl]-phenoxy}-butyric acid

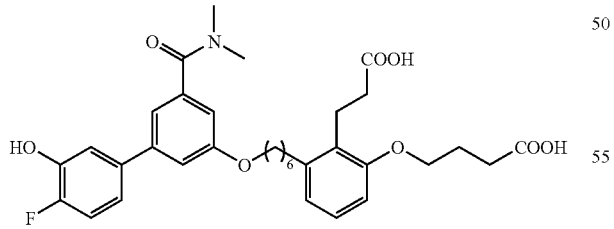

The title compound was prepared by the same method as 4-{2-(2-carboxy-ethyl)-3-[6-(5-dimethylcarbamoyl-3',4'-difluoro-biphenyl-3-yloxy)-hexyl]-phenoxy}-butyric acid starting from 4-{3-[6-(5-dimethylcarbamoyl-4'-fluoro-3'-hydroxy-biphenyl-3-yloxy)-hexyl]-2-(2-ethoxycarbonyl-ethyl)-phenoxy}-butyric acid ethyl ester (142 mg, 0.213 mmol) and 1.0 N aqueous NaOH (5 mL) in THF (5 mL) and EtOH (5 mL) to afford 4-{2-(2-carboxy-ethyl)-3-[6-(5-dim-ethylcarbamoyl-4'-fluoro-3'-hydroxy-biphenyl-3-yloxy)-hexyl]-phenoxy}-butyric acid (120 mg, 92%) as a white amorphous solid.

HRMS calcd for $C_{34}H_{40}NO_8F$ [M+Na]$^+$ 632.2630, observed 632.2635

Example 96

4-[3-{6-[3-Benzo[1,3]dioxol-5-yl-5-(3,3-difluoro-pyrrolidine-1-carbonyl)-phenoxy]-hexyl}-2-(2-carboxy-ethyl)-phenoxy]-butyric acid

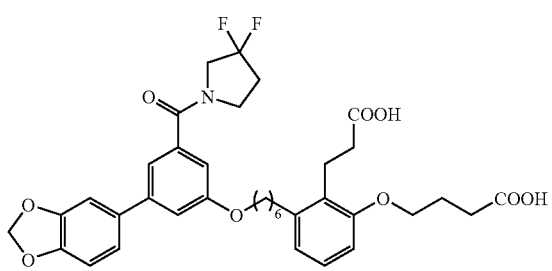

The title compound was prepared by the same method as 4-{2-(2-carboxy-ethyl)-3-[6-(5-dimethylcarbamoyl-3',4'-difluoro-biphenyl-3-yloxy)-hexyl]-phenoxy}-butyric acid starting from 4-[3-{6-[3-benzo[1,3]dioxol-5-yl-5-(3,3-difluoro-pyrrolidine-1-carbonyl)-phenoxy]-hexyl}-2-(2-ethoxycarbonyl-ethyl)-phenoxy]-butyric acid ethyl ester (120 mg, 0.163 mmol) and 1.0 N aqueous NaOH (1.63 mL) in EtOH (5.7 mL) to afford 4-[3-{6-[3-benzo[1,3]dioxol-5-yl-5-(3,3-difluoro-pyrrolidine-1-carbonyl)-phenoxy]-hexyl}-2-(2-carboxy-ethyl)-phenoxy]-butyric acid (73 mg, 66%) as a white amorphous solid.

HRMS calcd for $C_{37}H_{41}NO_9F_2$ [M+H]$^+$ 682.2822, observed 682.2817

Example 97

4-(2-(2-Carboxy-ethyl)-3-{6-[5-(3,3-difluoro-pyrrolidine-1-carbonyl)-biphenyl-3-yloxy]-hexyl}-phenoxy)-butyric acid

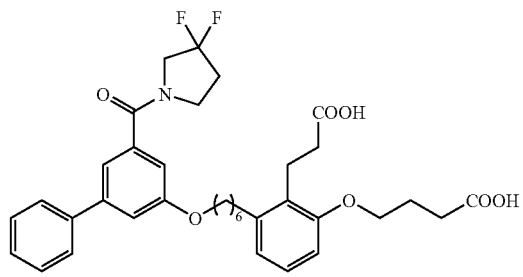

The title compound was prepared by the same method as 4-{2-(2-carboxy-ethyl)-3-[6-(5-dimethylcarbamoyl-3',4'-difluoro-biphenyl-3-yloxy)-hexyl]-phenoxy}-butyric acid starting from 4-[3-{6-[5-(3,3-difluoro-pyrrolidine-1-carbonyl)-biphenyl-3-yloxy]-hexyl}-2-(2-ethoxycarbonyl-ethyl)-phenoxy]-butyric acid ethyl ester (70 mg, 0.101 mmol) and 1.0 N aqueous NaOH (1.01 mL) in EtOH (4 mL) to afford 4-(2-(2-carboxy-ethyl)-3-{6-[5-(3,3-difluoro-pyrrolidine-1- carbonyl)-biphenyl-3-yloxy]-hexyl}-phenoxy)-butyric acid (64 mg, 99%) as a white amorphous solid.

HRMS calcd for $C_{36}H_{41}NO_7F_2$ [M+H]$^+$ 638.2924, observed 638.2920

Example 98

4-(2-(2-Carboxy-ethyl)-3-{6-[3-(3,3-difluoro-pyrrolidine-1-carbonyl)-5-thiophen-3-yl-phenoxy]-hexyl}-phenoxy)-butyric acid

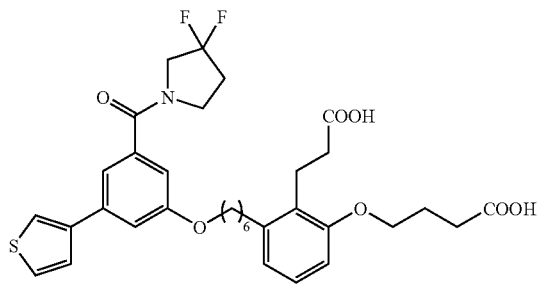

The title compound was prepared by the same method as 4-{2-(2-carboxy-ethyl)-3-[6-(5-dimethylcarbamoyl-3',4'-difluoro-biphenyl-3-yloxy)-hexyl]-phenoxy}-butyric acid starting from 4-[3-{6-[3-(3,3-difluoro-pyrrolidine-1-carbonyl)-5-thiophen-3-yl-phenoxy]-hexyl}-2-(2-ethoxycarbonyl-ethyl)-phenoxy]-butyric acid ethyl ester (71 mg, 0.11 mmol) and 1.0 N aqueous NaOH (1.1 mL) in EtOH (5 mL) to afford 4-(2-(2-carboxy-ethyl)-3-{6-[3-(3,3-difluoro-pyrrolidine-1-carbonyl)-5-thiophen-3-yl-phenoxy]-hexyl}-phenoxy)-butyric acid (64.7 mg, 91%) as a white amorphous solid.

HRMS calcd for $C_{34}H_{39}NO_7SF_2$ [M+H]$^+$ 644.2488, observed 644.2488

Example 99

4-(2-(2-Carboxy-ethyl)-3-{6-[3-(3,3-difluoro-pyrrolidine-1-carbonyl)-3'-fluoro-biphenyl-3-yloxy]-hexyl}-phenoxy)-butyric acid

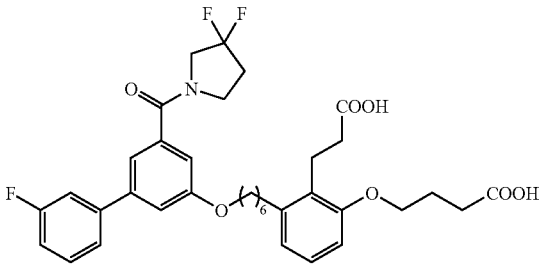

The title compound was prepared by the same method as 4-{2-(2-carboxy-ethyl)-3-[6-(5-dimethylcarbamoyl-3',4'-difluoro-biphenyl-3-yloxy)-hexyl]-phenoxy}-butyric acid starting from 4-[3-{6-[5-(3,3-difluoro-pyrrolidine-1-carbonyl)-3'-fluoro-biphenyl-3-yloxy]-hexyl}-2-(2-ethoxycarbonyl-ethyl)-phenoxy]-butyric acid ethyl ester (105 mg, 0.148 mmol) and 1.0 N aqueous NaOH (1.48 mL) in EtOH (5 mL) to afford 4-(2-(2-carboxy-ethyl)-3-{6-[3-(3,3-difluoro-pyrrolidine-1-carbonyl)-3'-fluoro-biphenyl-3-yloxy]-hexyl}-phenoxy)-butyric acid (94.6 mg, 98%) as a white amorphous solid.

HRMS calcd for $C_{36}H_{40}NO_7F_3$ [M+H]$^+$ 656.2830, observed 656.2832

Example 100

4-(2-(2-Carboxy-ethyl)-3-{6-[5-(2-difluoromethoxy-benzylcarbamoyl)-biphenyl-3-yloxy]-hexyl}-phenoxy)-butyric acid

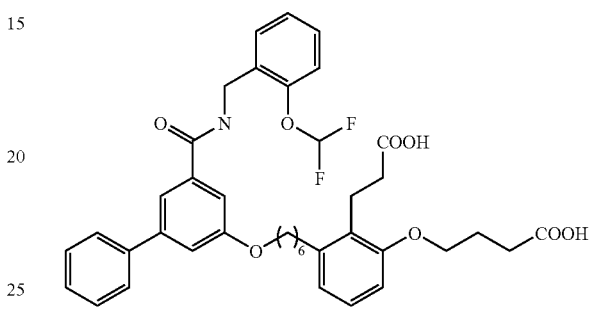

The title compound was prepared by the same method as 4-{2-(2-carboxy-ethyl)-3-[6-(5-dimethylcarbamoyl-3',4'-difluoro-biphenyl-3-yloxy)-hexyl]-phenoxy}-butyric acid starting from 4-[3-{6-[5-(2-difluoromethoxy-benzylcarbamoyl)-biphenyl-3-yloxy]-hexyl}-2-(2-ethoxycarbamoyl-ethyl)-phenoxy]-butyric acid ethyl ester (176 mg, 0.23 mmol) and 1.0 N aqueous NaOH (5 mL) in THF (5 mL) and EtOH (5 mL) to afford 4-(2-(2-carboxy-ethyl)-3-{6-[5-(2-difluoromethoxy-benzylcarbamoyl)-biphenyl-3-yloxy]-hexyl}-phenoxy)-butyric acid (129 mg, 80%) as a white amorphous solid.

HRMS calcd for $C_{40}H_{43}NO_8F_2$ [M+Na]$^+$ 726.2849, observed 726.2847

Example 101

4-[3-{6-[3-Benzo[1,3]dioxol-5-yl-5-(2-difluoromethoxy-benzylcarbamoyl)-phenoxy]-hexyl}-2-(2-carboxy-ethyl)-phenoxy]-butyric acid

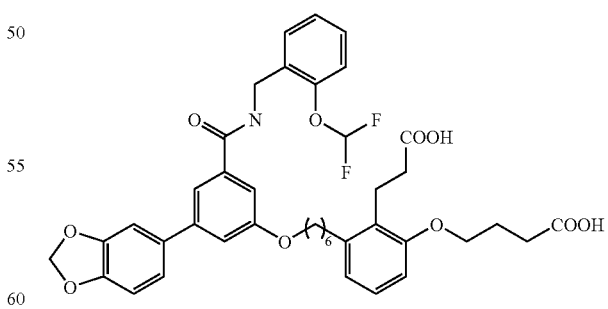

The title compound was prepared by the same method as 4-{2-(2-carboxy-ethyl)-3-[6-(5-dimethylcarbamoyl-3',4'-difluoro-biphenyl-3-yloxy)-hexyl]-phenoxy}-butyric acid starting from 4-[3-{6-[3-benzo[1,3]dioxol-5-yl-5-(2-difluoromethoxy-benzylcarbamoyl)-phenoxy]-hexyl}-2-(2-ethoxycarbonyl-ethyl)-phenoxy]-butyric acid ethyl ester (167 mg, 0.2 mmol) and 1.0 N aqueous NaOH (5 mL) in THF (5 mL) and EtOH (5 mL) to afford 4-[3-{6-[3-benzo[1,3] dioxol-5-yl-5-(2-difluoromethoxy-benzyl carbamoyl)-phenoxy]-hexyl}-2-(2-carboxy-ethyl)-phenoxy]-butyric acid (130 mg, 87%) as a white amorphous solid.

HRMS calcd for $C_{41}H_{43}NO_{10}F_2$ [M+Na]$^+$ 770.2747, observed 770.2753

Example 102

4-(2-(2-Carboxy-ethyl)-3-{6-[5-(2-difluoromethoxy-benzylcarbamoyl)-2'-fluoro-biphenyl-3-yloxy]-hexyl}-phenoxy)-butyric acid

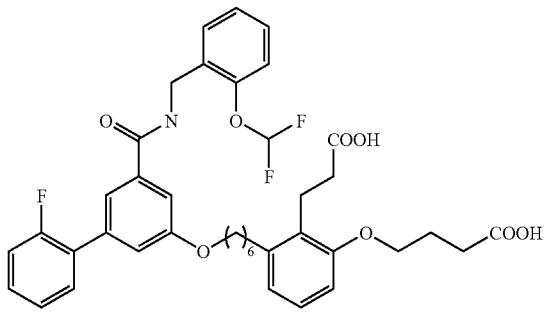

The title compound was prepared by the same method as 4-{2-(2-carboxy-ethyl)-3-[6-(5-dimethylcarbamoyl-3',4'-difluoro-biphenyl-3-yloxy)-hexyl]-phenoxy}-butyric acid starting from 4-[3-{6-[5-(2-difluoromethoxy-benzylcarbamoyl)-2'-fluoro-bi phenyl-3-yloxy]-hexyl}-2-(2-ethoxycarbonyl-ethyl)-phenoxy]-butyric acid ethyl ester (100 mg, 0.128 mmol) and 1.0 N aqueous NaOH (5 mL) in THF (5 mL) and EtOH (5 mL) to afford 4-(2-(2-carboxy-ethyl)-3-{6-[5-(2-difluoromethoxy-benzylcarbamoyl)-2'-fluoro-bi phenyl-3-yloxy]-hexyl}-phenoxy)-butyric acid (84 mg, 91%) as a white amorphous solid.

HRMS calcd for $C_{40}H_{42}NO_8F_3$ [M+Na]$^+$ 744.2755, observed 744.2756

Example 103

4-(2-(2-Carboxy-ethyl)-3-{6-[3-(2-difluoromethoxy-benzylcarbamoyl)-5-thiophen-3-yl-phenoxy]-hexyl}-phenoxy)-butyric acid

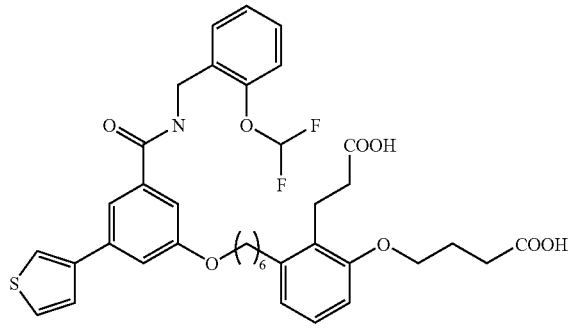

The title compound was prepared by the same method as 4-{2-(2-carboxy-ethyl)-3-[6-(5-dimethylcarbamoyl-3',4'-difluoro-biphenyl-3-yloxy)-hexyl]-phenoxy}-butyric acid starting from 4-[3-{6-[3-(2-difluoromethoxy-benzylcarbamoyl)-5-thiophen-3-yl-phenoxy]-hexyl}-2-(2-ethoxycarbonyl-ethyl)-phenoxy]-butyric acid ethyl ester (177 mg, 0.23 mmol) and 1.0 N aqueous NaOH (5 mL) in THF (5 mL) and EtOH (5 mL) to afford 4-(2-(2-carboxy-ethyl)-3-{6-[3-(2-difluoromethoxy-benzylcarbamoyl)-5-thiophen-3-yl-phenoxy]-hexyl}-phenoxy)-butyric acid (158 mg, 97%) as a dark brown solid.

HRMS calcd for $C_{38}H_{41}NO_8SF_2$ [M+Na]$^+$ 732.2413, observed 732.2408

Method F

Step 1:
3-Bromo-5-hydroxy-N,N-dimethyl-benzamide

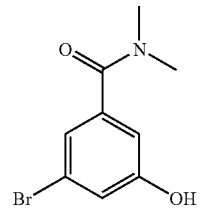

To a solution of 3-bromo-5-hydroxy-benzoic acid (2.0 g, 9.25 mmol), PyBroP (7.7 g, 18.5 mmol) and diisopropylethylamine (6.4 mL, 37 mmol) in DMF (50 mL) was added dimethylamine hydrochloride (1.51 g, 18.5 mmol). The reaction mixture was stirred at room temperature for 6 h. The reaction mixture was diluted with ethyl acetate and washed with brine. The organic extract was dried over anhydrous sodium sulfate and concentrated under reduced pressure. The crude material was purified by column chromatography (Isco™ 120 g) using ethyl acetate as eluting solvent to give the title compound (1.5 g, 67%) as a white solid.

HRMS calcd for $C_9H_{10}NO_2Br$ [M+H]$^+$ 243.9968, observed 243.9968

Step 2: 4-[3-[6-(3-Bromo-5-dimethylcarbamoyl-phenoxy)-hexyl]-2-(2-ethoxycarbonyl-ethyl)-phenoxy]-butyric acid ethyl ester

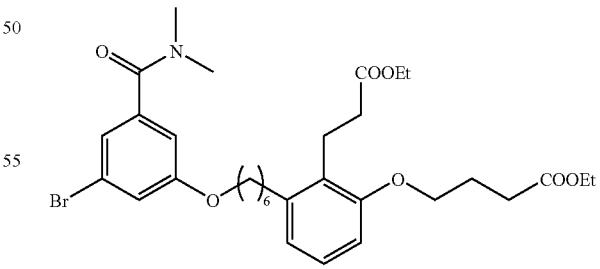

To a solution of 4-[3-(6-bromo-hexyl)-2-(2-ethoxycarbonyl-ethyl)-phenoxy]-butyric acid ethyl ester (3.48 g, 7.4 mmol), 3-bromo-5-hydroxy-N,N-dimethyl-benzamide (1.5 g, 6.17 mmol) in N,N-dimethylformamide (30 mL) and acetone (60 mL) was added potassium carbonate (8.51 g, 61.7 mmol). The resulting suspension was heated to 70° C. for 24 h. Then the reaction mixture was cooled to room temperature and diluted with water and 10% aq. HCl. The organic compound was extracted into ethyl acetate and the combined organic extracts were washed with water and brine solution. The organic extracts were dried over anhydrous sodium sulfate and removal of the solvent under reduced pressure gave the crude product which was purified on ISCO™ column (120 g) using 50% ethyl acetate in hexanes as eluting solvent to give the title compound (3.1 g, 80%) as colorless oil.

HRMS calcd for $C_{32}H_{44}NO_7Br$ [M+H]$^+$ 634.2374, observed 634.2375

Steps 3 and 4:

General Procedure:

4-[3-[6-(3-Bromo-5-dimethyl carbamoyl-phenoxy)-hexyl]-2-(2-ethoxycarbonyl-ethyl)-phenoxy]-butyric acid ethyl ester (100 mg, 0.157 mmol), 1,2-dimethoxyethane (3 mL), appropriate boronic acid (100 mg), $Cs_2CO_3$ (100 mg) and $PdCl_2(dppf)$ (20 mg) were placed in a sealed tube and shaken at 90° C. for 4 hrs. Then the reaction mixture was diluted with ethyl acetate (5 mL) and washed with water (3 mL). The organic extract was dried over anhydrous sodium sulfate and concentration under reduced pressure gave an oil, which was used in the next step without further purification. The crude material from the previous step was dissolved in EtOH (5 mL) and 3N NaOH (0.5 mL) was added and the resulting reaction mixture was stirred at room temperature for 3 hrs. Then 3N HCl (0.55 mL) was added to neutralize the reaction mixture. Concentration under reduced pressure gave an oil which was purified by reverse-phase HPLC.

Example 104

4-{2-(2-Carboxy-ethyl)-3-[6-(4'-chloro-5-dimethyl-carbamoyl-3'-fluoro-biphenyl-3-yloxy)-hexyl]-phenoxy}-butyric acid

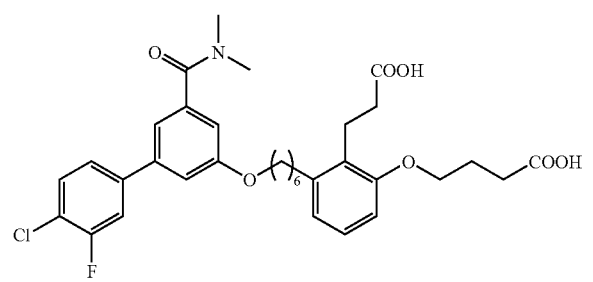

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 4-chloro-3-fluorophenylboronic acid. LC/MS indicated a purity of 92% as measured by UV 214 nM. Yield: 40% (after two steps)

HRMS calcd for $C_{34}H_{40}ClFNO_7$ [M+H]$^+$ 628.2472, observed 628.2477

Example 105

4-{2-(2-Carboxy-ethyl)-3-[6-(5-dimethylcarbamoyl-3'-fluoro-4'-methyl-biphenyl-3-yloxy)-hexyl]-phenoxy}-butyric acid

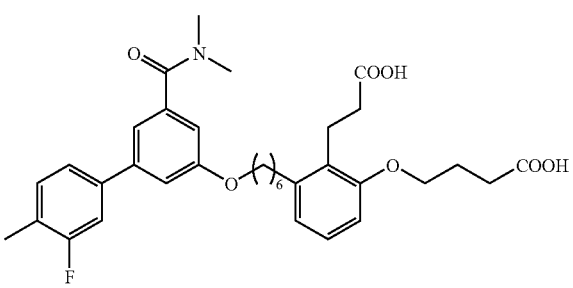

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 3-fluoro-4-methylphenylboronic acid. LC/MS indicated a purity of 100% as measured by UV 214 nM. Yield: 30% (after two steps)

HRMS calcd for $C_{35}H_{43}FNO_7$ [M+H]$^+$ 608.3018, observed 608.3022

Example 106

4-{2-(2-Carboxy-ethyl)-3-[6-(5-dimethylcarbamoyl-4'-fluoro-biphenyl-3-yloxy)-hexyl]-phenoxy}-butyric acid

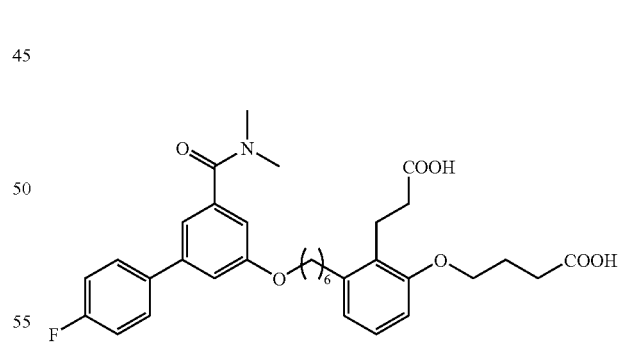

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 4-fluorophenylboronic acid. LC/MS indicated a purity of 100% as measured by UV 214 nM. Yield: 41% (after two steps)

HRMS calcd for $C_{34}H_{41}FNO_7$ [M+H]$^+$ 594.2862, observed 594.2859

Example 107

4-{2-(2-Carboxy-ethyl)-3-[6-(5-dimethylcarbamoyl-3'-fluoro-4'-methoxy-biphenyl-3-yloxy)-hexyl]-phenoxy}-butyric acid

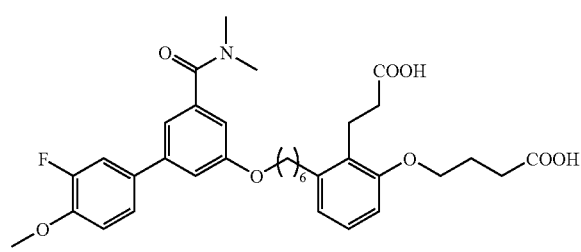

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 3-fluoro-4-methoxyphenylboronic acid. LC/MS indicated a purity of 100% as measured by UV 214 nM.

HRMS calcd for $C_{35}H_{43}FNO_8$ [M+H]$^+$ 624.2967, observed 624.2971

Example 108

4-{2-(2-Carboxy-ethyl)-3-[6-(4'-chloro-5-dimethylcarbamoyl-biphenyl-3-yloxy)-hexyl]-phenoxy}-butyric acid

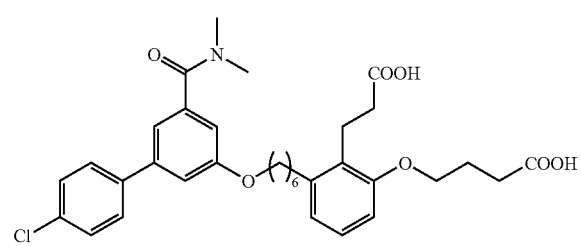

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 4-chlorophenylboronic acid. LC/MS indicated a purity of 100% as measured by UV 214 nM.

HRMS calcd for $C_{34}H_{41}ClNO_7$ [M+H]$^+$ 610.2566, observed 610.2567

Example 109

4-{2-(2-Carboxy-ethyl)-3-[6-(3'-chloro-5-dimethylcarbamoyl-biphenyl-3-yloxy)-hexyl]-phenoxy}-butyric acid

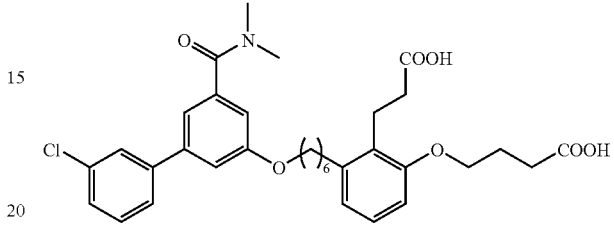

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 3-chlorophenylboronic acid. LC/MS indicated a purity of 100% as measured by UV 214 nM.

HRMS calculated for $C_{34}H_{41}ClNO_7$ [M+H]$^+$ 610.2566, observed 610.2565

Example 110

4-{2-(2-Carboxy-ethyl)-3-[6-(5-dimethylcarbamoyl-3'-methoxy-biphenyl-3-yloxy)-hexyl]-phenoxy}-butyric acid

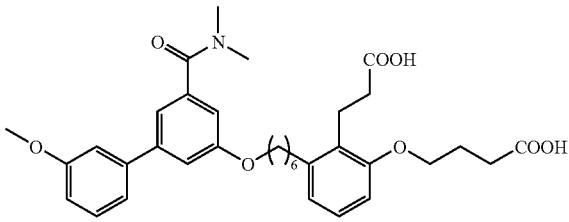

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 3-methoxyphenylboronic acid. LC/MS indicated a purity of 100% as measured by UV 214 nM.

HRMS calcd for $C_{35}H_{44}NO_8$ [M+H]$^+$ 606.3062, observed 606.3062

Example 111

4-{2-(2-Carboxy-ethyl)-3-[6-(5-dimethylcarbamoyl-3',5'-difluoro-biphenyl-3-yloxy)-hexyl]-phenoxy}-butyric acid

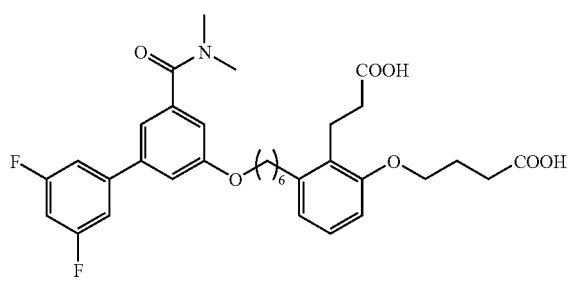

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 3,5-difluorophenylboronic acid. LC/MS indicated a purity of 100% as measured by UV 214 nM.

HRMS calcd for $C_{34}H_{40}F_2NO_7$ [M+H]$^+$ 612.2768, observed 612.2767

Example 112

4-{2-(2-Carboxy-ethyl)-3-[6-(5-dimethylcarbamoyl-4'-methyl-biphenyl-3-yloxy)-hexyl]-phenoxy}-butyric acid

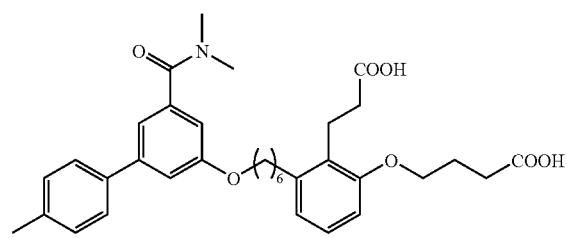

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 4-methylphenylboronic acid. LC/MS indicated a purity of 100% as measured by UV 214 nM.

HRMS calcd for $C_{35}H_{44}NO_7$ [M+H]$^+$ 590.3113, observed 590.3117

Example 113

4-{2-(2-Carboxy-ethyl)-3-[6-(5-dimethylcarbamoyl-4'-ethyl-biphenyl-3-yloxy)-hexyl]-phenoxy}-butyric acid

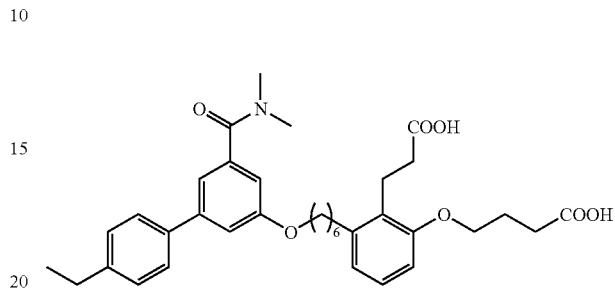

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 4-ethylphenylboronic acid. LC/MS indicated a purity of 100% as measured by UV 214 nM.

HRMS calcd for $C_{36}H_{46}NO_7$ [M+H]$^+$ 604.3269, observed 604.3273

Example 114

4-{2-(2-Carboxy-ethyl)-3-[6-(3-dimethylcarbamoyl-5-pyridin-4-yl-phenoxy)-hexyl]-phenoxy}-butyric acid

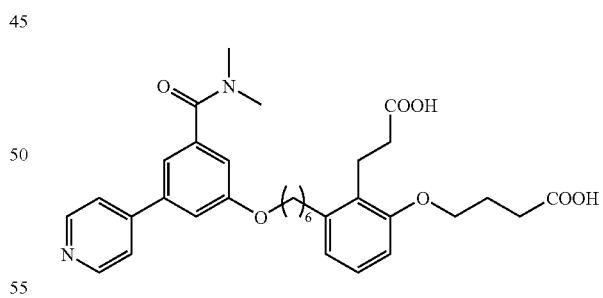

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and pyridine-4-boronic acid. LC/MS indicated a purity of 100% as measured by UV 214 nM.

HRMS calcd for $C_{33}H_{41}N_2O_7$ [M+H]$^+$ 577.2909, observed 577.2907

Example 115

4-(2-(2-Carboxy-ethyl)-3-{6-[3-(2,3-dihydro-benzo-furan-5-yl)-5-dimethylcarbamoyl-phenoxy]-hexyl}-phenoxy)-butyric acid

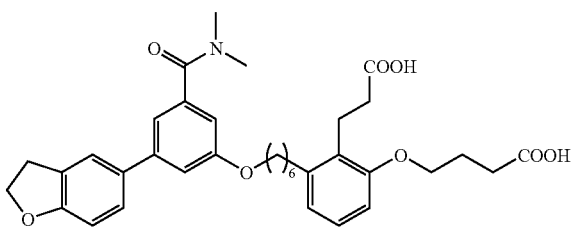

The title compound was prepared according to the general procedure described in Steps 3 and 4 of Method F starting from 4-[3-[6-(3-bromo-5-dimethylcarbamoyl-phenoxy)-hexyl]-2-(2-ethoxycarbonyl-ethyl)-phenoxy]-butyric acid ethyl ester and 2,3-dihydrobenzofuran-5-boronic acid. LC/MS indicated a purity of 93% as measured by UV 214 nM.

HRMS calcd for $C_{36}H_{44}NO_8$ [M+H]$^+$ 628.3062, observed 618.3061

Method G

Ohira's reagent was prepared as described in literature (*Synlett*. 1996, 521).

Step 1: 4-[2-(2-Ethoxycarbonyl-ethyl)-3-(6-oxo-hexyl)-phenoxy]-butyric acid ethyl ester

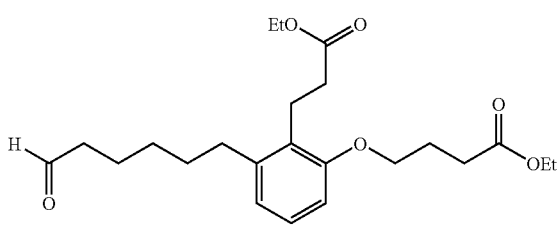

4-[3-(6-Bromo-hexyl)-2-(2-ethoxycarbonyl-ethyl)-phenoxy]-butyric acid ethyl ester (10.0 g, 21.2 mmol), pyridine N-oxide (10.06 g, 106 mmol), and sodium bicarbonate (10.0 g, 119 mmol) were heated at reflux with vigorous stirring in toluene (100 mL) for 24 h. The mixture was cooled to room temperature and filtered. The filtrate was then concentrated under reduced pressure and the crude material was purified by column chromatography using 30% ethyl acetate-hexanes as eluant to give the title compound (7.0 g, 81%) as an oil.

HRMS calcd for $C_{23}H_{34}O_6$ [M$^+$] 406.2350, observed 406.2355

Step 2: 4-[3-Hept-6-ynyl-2-(2-methoxycarbonyl-ethyl)-phenoxy]-butyric acid methyl ester

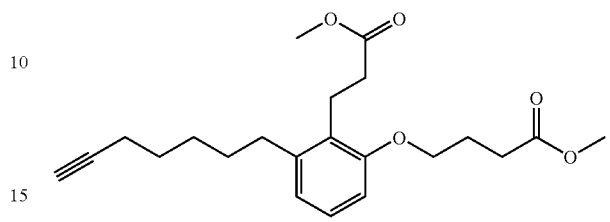

To a solution of 4-[2-(2-ethoxycarbonyl-ethyl)-3-(6-oxo-hexyl)-phenoxy]-butyric acid ethyl ester (7.0 g, 17.24 mmol) was added a solution of potassium carbonate (7.14 g, 51.72 mmol) in MeOH (200 mL) and the resulting mixture was cooled to 0° C. Then the Ohira's reagent (ref. cited in *Synlett*, 1996, 521) (6.3 g, 32.8 mmol) in MeOH (50 mL) was added slowly. The cooling bath was removed upon the end of addition and the reaction mixture was stirred at room temperature for 5 hr. The reaction was then extracted into ethyl acetate and washed with brine. The combined organic extracts were dried over sodium sulfate and concentrated under reduced pressure. The crude material was purified by column chromatography using 50% ethyl acetate-hexanes as eluant to give the title compound (4.6 g, 71%) as a light yellow oil.

HRMS calculated for $C_{22}H_{30}O_5$ [M+Na]$^+$ 397.1985, observed 397.1985

Step 3: 4-[2-(2-Carboxy-ethyl)-3-hept-6-ynyl-phenoxy]-butyric acid

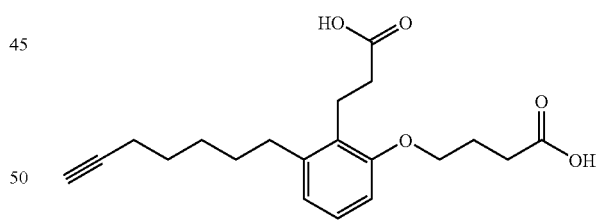

To a solution of 4-[3-hept-6-ynyl-2-(2-methoxycarbonyl-ethyl)-phenoxy]-butyric acid methyl ester (4.6 g, 12.39 mmol) in EtOH (100 mL) was added NaOH (4.96 g, 123.9 mmol) and 20 mL of water. The reaction mixture was heated at 50° C. and stirred at this temperature for 5 h. After cooling to room temperature, a solution of 10% aq. HCl was added. The solution was then extracted with ethyl acetate (100 mL), the organic extract was dried over $Na_2SO_4$ and concentrated under reduced pressure to afford the desired diacid (4.0 g, 93%) as a light yellow oil.

HRMS calcd for $C_{20}H_{26}O_5$ [M+Na]$^+$ 369.1672, observed 369.1673

Step 4

(3-Bromo-5-iodo-phenyl)-(4-methyl-piperazin-1-yl)-methanone

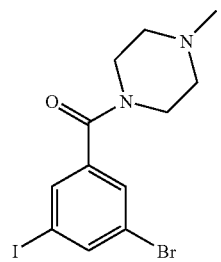

A solution of 3-bromo-5-iodo-benzoic acid (5.0 g, 15.3 mmol) in 100 mL of thionyl chloride was heated under reflux for 2 h. The reaction mixture was cooled to room temperature and concentrated under reduced pressure. The resulting solid was then dissolved in 100 mL of $CH_2Cl_2$. N-Methyl-piperazine (2.5 mL, 22.9 mmol) and DIPEA (5.3 mL, 30.6 mmol) were added and the reaction mixture was stirred at room temperature for 3 h. The resulting solution was concentrated under reduced pressure and the crude material was purified by column chromatography (Isco™ 330 g) using 20% MeOH/EtOAc as eluting solvent to afford 5 g (80%) of (3-bromo-5-iodo-phenyl)-(4-methyl-piperazin-1-yl)-methanone as a white solid.

HRMS calcd for $C_{12}H_{24}N_2OBrI$ $[M+H]^+$ 408.9407, observed 408.9408

3-Bromo-5-iodo-N,N-dimethyl-benzamide

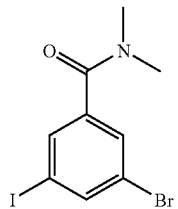

A solution of 3-bromo-5-Iodo-benzoic acid (4.0 g, 12.2 mmol) in 100 mL of thionyl chloride was heated under reflux for 2 h. The reaction mixture was cooled to room temperature and concentrated under reduced pressure. The resulting solid was then dissolved in 80 mL of $CH_2Cl_2$. Dimethylamine hydrochloride (1.5 g, 18.3 mmol) and DIPEA (4.3 mL, 24.5 mmol) was added and the reaction mixture was stirred at room temperature for 3 h. The resulting solution was concentrated under reduced pressure and the crude material was purified by column chromatography (Isco™ 330 g) using 50% hexanes/EtOAc as eluting solvent to afford 3.8 g (88%) of 3-bromo-5-iodo-N,N-dimethyl-benzamide as a white solid.

HRMS calcd for $C_9H_9NOBrI$ $[M+H]^+$ 353.8985, observed 353.8985

Step 5

4-[3-[-{7-[3-Bromo-5-(4-methyl-piperazine-1-carbonyl)phenyl]-hept-6-ynyl}-2-(2-carboxy-ethyl)phenoxy]butyric acid]

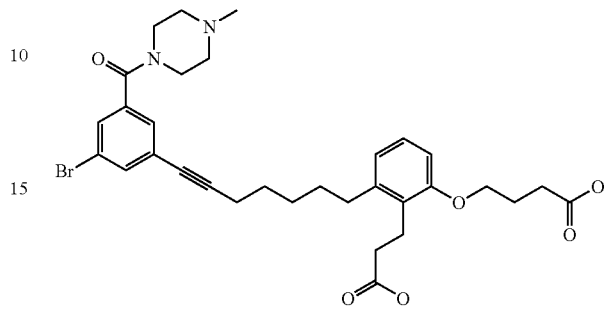

To a solution of 4-[2-(2-carboxy-ethyl)-3-hept-6-ynyl-phenoxy]-butyric acid (381 mg, 1.1 mmol), (3-bromo-5-iodo-phenyl)-(4-methyl-piperazin-1-yl)-methanone (500 mg, 1.2 mmol), CuI (10 mg, 0.055 mmol) in THF (20 mL) and TEA (10 mL) was added bis-(triphenylphosphine)palladium (II) dichloride (39 mg, 0.055 mmol). The reaction mixture was heated at 60° C. for 5 h. Then the reaction mixture was cooled to room temperature, a few drops of TFA were added and the resulting mixture was concentrated under reduced pressure. The crude material was purified by column chromatography (Isco™ 120 g) using a gradient from EtOAc to 30% MeOH-EtOAc as eluting solvent to give the title compound (550 mg, 70%) as an oil.

HRMS calcd for $C_{32}H_{39}N_2O_6Br$ $[M+H]^+$ 627.2064, observed 627.2069

4-[3-[7-(3-Bromo-5-dimethylcarbamoyl-phenyl)-hept-6-ynyl]-2-(2-carboxy-ethyl)-phenoxy]-butyric acid

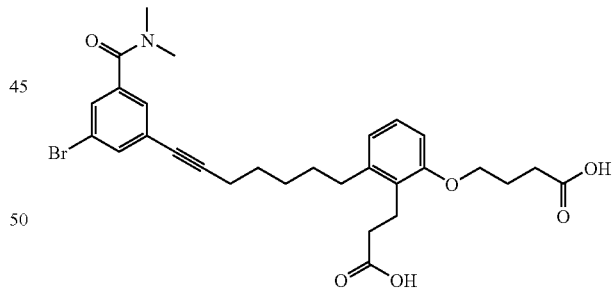

To a solution of 4-[2-(2-carboxy-ethyl)-3-hept-6-ynyl-phenoxy]-butyric acid (900 mg, 2.6 mmol), 3-bromo-5-iodo-N,N-dimethyl-benzamide (1.0 g, 2.8 mmol), CuI (20 mg, 0.11 mmol) in THF (10 mL) and TEA (10 mL) was added bis(triphenylphosphine) palladium(II) dichloride (75 mg, 0.11 mmol). The reaction mixture was heated at 70° C. for 5 h. Then the reaction mixture was cooled to room temperature, a few drops of TFA were added and the resulting mixture was concentrated under reduced pressure. The crude material was purified by column chromatography (Isco™ 120 g) using ethyl acetate as eluting solvent to give the title compound (980 mg, 65%) as an oil.

HRMS calcd for $C_{29}H_{34}NO_6Br$ $[M+H]^+$ 572.1643, observed 572.1641

Example 116

4-[3-{7-[3-Benzo[1,3]dioxol-5-yl-5-(4-methyl-piperazine-1-carbonyl)-phenyl]-hept-6-ynyl}-2-(2-carboxy-ethyl)-phenoxy]-butyric acid

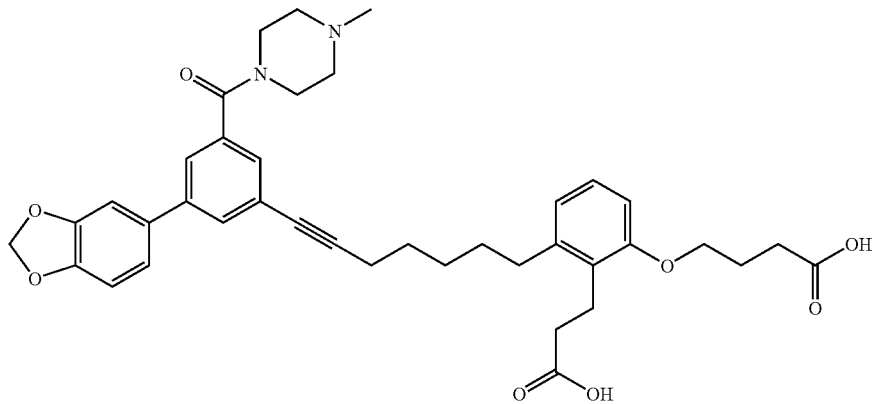

To a solution of 4-[3[-{7-[3-bromo-5-(4-methyl-piperazine-1-carbonyl)phenyl]-hept-6-ynyl}-2-(2-carboxy-ethyl)phenoxy]butyric acid] (60 mg, 0.096 mmol) in EtOH (4 mL)/H$_2$O (1 mL) were added 3,4-methylenedioxyphenylboronic acid (32 mg, 0.19 mmol), potassium carbonate (53 mg, 0.38 mmol) and Pd(PPh$_3$)$_4$ (6 mg, 0.0048 mmol). The mixture was heated at 78° C. for 5 h and then cooled to room temperature. The reaction mixture was filtered using a syringe filter 0.45 μm and the filtrate was concentrated under reduced pressure. The crude oil was then purified by preparative HPLC using acetonitrile/water gradient. Yield: 65%

HRMS calcd for C$_{39}$H$_{44}$N$_2$O$_8$ [M+H]$^+$ 669.3171, observed 669.3167

Example 117

4-(2-(2-Carboxy-ethyl)-3-{7-[5-(4-methyl-piperazine-1-carbonyl)-biphenyl-3-yl]-hept-6-ynyl}-phenoxy)-butyric acid

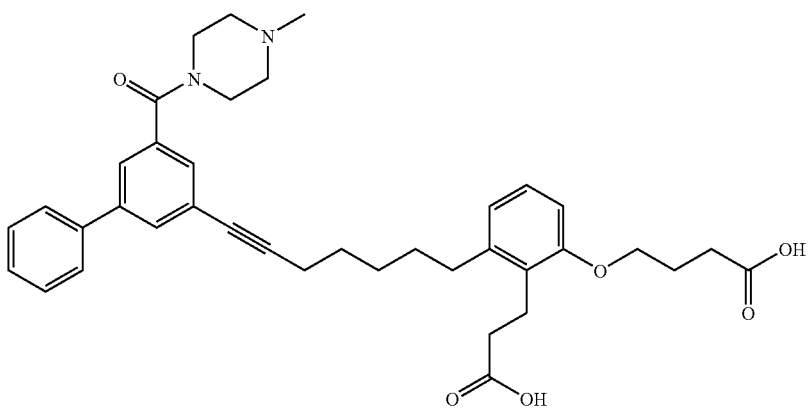

To a solution of 4-[3[-{7-[3-bromo-5-(4-methyl-piperazine-1-carbonyl)phenyl]-hept-6-ynyl}-2-(2-carboxy-ethyl)phenoxy]butyric acid] (60 mg, 0.096 mmol) in EtOH (4 mL)/H$_2$O (1 mL) were added phenylboronic acid (25 mg, 0.19 mmol), potassium carbonate (53 mg, 0.38 mmol) and Pd(PPh$_3$)$_4$ (6 mg, 0.0048 mmol). The mixture was heated at 78° C. for 5 h and then cooled to room temperature. The reaction mixture was filtered using a syringe filter 0.45 μm and the filtrate was concentrated under reduced pressure. The crude oil was then purified by preparative HPLC using acetonitrile/water gradient. Yield: 33%

HRMS calcd for C$_{38}$H$_{44}$N$_2$O$_6$ [M+H]$^+$ 625.3271, observed 625.3275

Example 118

4-(2-(2-Carboxy-ethyl)-3-{7-[5-(4-methyl-piperazine-1-carbonyl)-biphenyl-3-yl]-heptyl}-phenoxy)-butyric acid

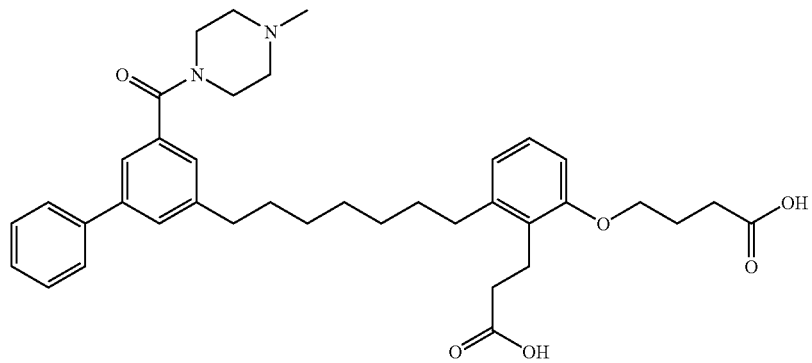

To a solution of 4-(2-(2-Carboxy-ethyl)-3-{7-[5-(4-methyl-piperazine-1-carbonyl)-biphenyl-3-yl]-hept-6-ynyl}-phenoxy)-butyric acid (20 mg, 0.032 mmol) in MeOH (4 mL) was added 10% Pd/C (2 mg). The mixture was stirred for 4 h under hydrogen atmosphere at room temperature. The resulting suspension was filtered through Celite™ and concentrated under reduced pressure to afford the title compound.

Yield: 90%

HRMS calcd for $C_{38}H_{48}N_2O_6$ [M+H]$^+$ 629.3585, observed 629.3587

Example 119

4-[3-[7-(3-Benzo[1,3]dioxol-5-yl-5-dimethylcarbamoyl-phenyl)-hept-6-ynyl]-2-(2-carboxy-ethyl)-phenoxy]-butyric acid

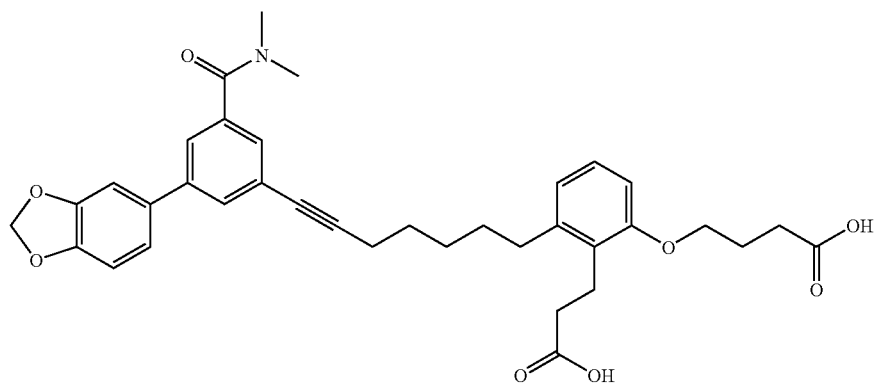

To a solution of 4-[3-[7-(3-bromo-5-dimethylcarbamoyl-phenyl)-hept-6-ynyl]-2-(2-carboxy-ethyl)-phenoxy]-butyric acid (100 mg, 0.17 mmol) in EtOH (4 mL)/H$_2$O (1 mL) were added 3,4-methylenedioxyphenylboronic acid (58 mg, 0.35 mmol), potassium carbonate (100 mg, 0.7 mmol) and Pd(PPh$_3$)$_4$ (5 mg, 0.004 mmol). The mixture was heated at 78° C. for 5 h and then cooled to room temperature. The reaction mixture was filtered using a syringe filter 0.45 μm and the filtrate concentrated under reduced pressure. The crude oil was then purified by preparative HPLC using acetonitrile/water gradient. HRMS calcd for $C_{36}H_{39}NO_8$ [M+H]$^+$ 614.2749, observed 614.2748

Example 120

4-{2-(2-Carboxy-ethyl)-3-[7-(5-dimethylcarbamoyl-biphenyl-3-yl)-hept-6-ynyl]-phenoxy}-butyric acid

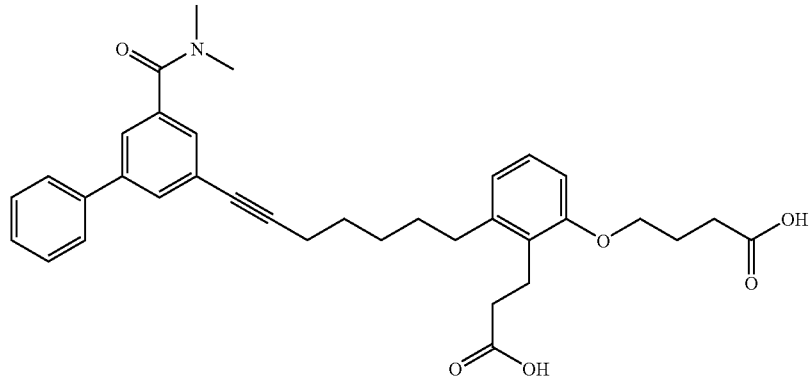

To a solution of 4-[3-[7-(3-bromo-5-dimethylcarbamoyl-phenyl)-hept-6-ynyl]-2-(2-carboxy-ethyl)-phenoxy]-butyric acid (100 mg, 0.17 mmol) in EtOH (4 mL)/H$_2$O (1 mL) were added phenylboronic acid (50 mg, 0.35 mmol), potassium carbonate (100 mg, 0.7 mmol) and Pd(PPh$_3$)$_4$ (5 mg, 0.004 mmol). The mixture was heated at 78° C. for 5 h and then cooled to room temperature. The reaction mixture was filtered using a syringe filter 0.45 μm and the filtrate was concentrated under reduced pressure. The crude oil was then purified by preparative HPLC using acetonitrile/water gradient.

HRMS calcd for C$_{35}$H$_{39}$NO$_6$ [M+Na]$^+$ 592.2669, observed 592.2670

Example 121

4-{2-(2-Carboxy-ethyl)-3-[7-(5-dimethylcarbamoyl-3'-fluoro-biphenyl-3-yl)-hept-6-ynyl]-phenoxy}-butyric acid

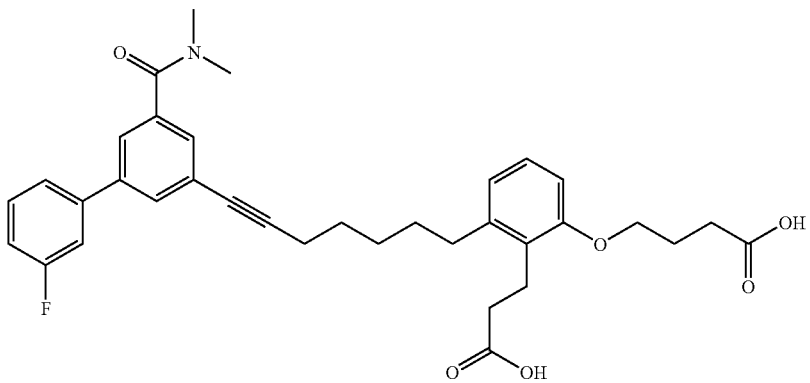

To a solution of 4-[3-[7-(3-bromo-5-dimethylcarbamoyl-phenyl)-hept-6-ynyl]-2-(2-carboxy-ethyl)-phenoxy]-butyric acid (80 mg, 0.14 mmol) in EtOH (4 mL)/H$_2$O (1 mL) were added 3-fluorophenylboronic acid (39 mg, 0.28 mmol), potassium carbonate (77 mg, 0.56 mmol) and Pd(PPh$_3$)$_4$ (3 mg, 0.0028 mmol). The mixture was heated at 78° C. for 5 h and then cooled to room temperature. The reaction mixture was filtered using a syringe filter 0.45 μm and the filtrate was concentrated under reduced pressure. The crude oil was then purified by preparative HPLC using acetonitrile/water gradient.

HRMS calcd for C$_{35}$H$_{38}$NO$_6$F [M+Na]$^+$ 610.2575, observed 610.2571

Example 122

4-{2-(2-Carboxy-ethyl)-3-[7-(5-dimethylcarbamoyl-4'-hydroxy-biphenyl-3-yl)-hept-6-ynyl]-phenoxy}-butyric acid

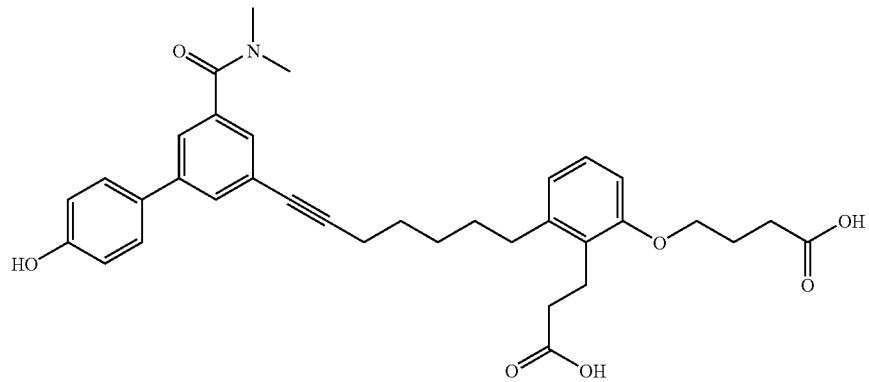

To a solution of 4-[3-[7-(3-bromo-5-dimethylcarbamoyl-phenyl)-hept-6-ynyl]-2-(2-carboxy-ethyl)-phenoxy]-butyric acid (80 mg, 0.14 mmol) in EtOH (4 mL)/H$_2$O (1 mL) were added 4-hydroxyphenylboronic acid (38 mg, 0.28 mmol), potassium carbonate (77 mg, 0.56 mmol) and Pd(PPh$_3$)$_4$ (3 mg, 0.0028 mmol). The mixture was heated at 78° C. for 5 h and then cooled to room temperature. The reaction mixture was filtered using a syringe filter 0.45 µm and the filtrate was concentrated under reduced pressure. The crude oil was then purified by preparative HPLC using acetonitrile/water gradient.

HRMS calcd for $C_{35}H_{39}NO_7$ [M+H]$^+$ 586.2800, observed 586.2801

Example 123

Assay of Compounds for Inhibition of LTB$_4$ Activity

Ca$^{2+}$ Flux Assay for LTB4 Antagonist Assay
Cell Culture Conditions:

Human leukemia HL-60 cells endogenously expressing BLT1 and BLT2 receptors were cultured in RPMI-1640 medium supplemented with 20% fetal bovine serum, 2 mM glutamine, 100 U/mL penicillin and 100 ug/mL streptomycin.

Seventy two hours prior to experiment cells are counted using ViaCount reagent, centrifuged and resuspended at 2.0×10$^5$ cells/ml density with the complete growth media containing 1 µM retinoic acid (Sigma).

Dye Loading and Assay:

On a day of the experiment loading buffer (Calcium-3 Assay Kit, Molecular Devices) was prepared by dissolving the contents of one vial (Express Kit) into 500 ml Hank's Balanced Salt Solution containing 20 mM HEPES and 5 mM probenecid. Equal volume of the loading buffer was mixed with the replacement buffer (Hank's Balanced Salt Solution containing 20 mM HEPES, 0.05% BSA and 5 mM probenecid). Retinoic acid induced HL-60 cells were counted using ViaCount reagent, centrifuged and resuspended at 2.0× 10$^6$ cells/mL density with the loading buffer/replacement buffer, dispensed into 384 well black/clear microplates (Falcon)(25 µL/well) and placed in a 37° C./5% CO$_2$ incubator for 1 hour.

During the incubation, test compounds were prepared at 6× the desired concentration in HBSS/20 mM HEPES/0.05% BSA as well as LTB4 (Biomol) was prepared at 2.2× concentration in HBSS/20 mM HEPES/0.5% BSA buffer.

After the incubation, both the cell and compound plates were brought to the FLIPR and 5 µL of the diluted compounds were transferred to the cell plates by the FLIPR. Plates were then incubated for 30 min at room temperature. After the ½ hour incubation, plates were returned to the FLIPR and 25 µL of 2.2×LTB4 was added to the cell plates. During the assay, fluorescence readings were taken simultaneously from all 384 wells of the cell plate every 1.5 seconds. Five readings were taken to establish a stable baseline, then 25 µL (LTB4) of sample was rapidly and simultaneously added to each well of the cell plate. The fluorescence was continuously monitored before, during and after sample addition for a total elapsed time of 100 seconds. Responses (increase in peak fluorescence) in each well following agonist addition was determined. The initial fluorescence reading from each well, prior to ligand stimulation, was used a zero baseline value for the data from that well. The responses are expressed as % inhibition of the neutral control (neural control: wells that received buffer plus DMSO but no test compound). Assay results for a representative number of compounds are provided below:

| Example # | Compound name | LTB4 antagonism (HL-60 FLIPR) |
|---|---|---|
| Example 5 | 4-[3-[6-(5-Benzylcarbamoyl-2',6'-difluoro-biphenyl-3-yloxy)-hexyl]-2-(2-carboxy-ethyl)-phenoxy]-butyric acid | IC50 = 298.57 nM |
| Example 24 | 4-(2-(2-Carboxy-ethyl)-3-{6-[3-(4-methyl-piperazine-1-carbonyl)-5-(4-methyl-thiophen-3-yl)-phenoxy]-hexyl}-phenoxy)-butyric acid | IC50 = 47.26 nM |

-continued

| Example # | Compound name | LTB4 antagonism (HL-60 FLIPR) |
|---|---|---|
| Example 28 | 4-(2-(2-Carboxy-ethyl)-3-{6-[5-(4-methyl-piperazine-1-carbonyl)-biphenyl-3-yloxy]-hexyl}-phenoxy)-butyric acid | IC50 = 0.22 nM |
| Example 36 | 4-[3-{6-[3-Benzo[1,3]dioxol-5-yl-5-(4-methyl-[1,4]diazepane-1-carbonyl)-phenoxy]-hexyl}-2-(2-carboxy-ethyl)-phenoxy]-butyric acid | IC50 = 0.14 nM |
| Example 42 | 4-[3-{6-[3-Benzo[1,3]dioxol-5-yl-5-(piperidine-1-carbonyl)-phenoxy]-hexyl}-2-(2-carboxy-ethyl)-phenoxy]-butyric acid | IC50 = 0.21 nM |
| Example 44 | 4-[3-{6-[3-Benzo[1,3]dioxol-5-yl-5-(piperazine-1-carbonyl)-phenoxy]-hexyl}-2-(2-carboxy-ethyl)-phenoxy]-butyric acid | IC50 = 0.08 nM |
| Example 46 | 4-[3-{6-[3-Benzo[1,3]dioxol-5-yl-5-(3-methyl-piperidine-1-carbonyl)-phenoxy]-hexyl}-2-(2-carboxy-ethyl)-phenoxy]-butyric acid | IC50 = 7.46 nM |
| Example 51 | 4-[3-[6-(3-Benzo[1,3]dioxol-5-yl-5-cyclopropylcarbamoyl-phenoxy)-hexyl]-2-(2-carboxy-ethyl)-phenoxy]-butyric acid | IC50 = 0.08 nM |
| Example 53 | 4-[3-[6-(3-Benzo[1,3]dioxol-5-yl-5-dimethylcarbamoyl-phenoxy)-hexyl]-2-(2-carboxy-ethyl)-phenoxy]-butyric acid | IC50 = 0.1 nM |
| Example 55 | 4-[3-[6-(3-Benzo[1,3]dioxol-5-yl-5-carbamoyl-phenoxy)-hexyl]-2-(2-carboxy-ethyl)-phenoxy]-butyric acid | IC50 = 0.2 nM |
| Example 61 | 4-[3-[6-(3-Benzo[1,3]dioxol-5-yl-5-cyclobutylcarbamoyl-phenoxy)-hexyl]-2-(2-carboxy-ethyl)-phenoxy]-butyric acid | IC50 = 0.21 nM |
| Example 67 | 4-{2-(2-Carboxy-ethyl)-3-[6-(5-cyclobutylcarbamoyl-3'-fluoro-biphenyl-3-yloxy)-hexyl]-phenoxy}-butyric acid | IC50 = 52.16 nM |
| Example 73 | 4-[3-{6-[3-Benzo[1,3]dioxol-5-yl-5-(ethyl-methyl-carbamoyl)-phenoxy]-hexyl}-2-(2-carboxy-ethyl)-phenoxy]-butyric acid | IC50 = 0.25 nM |
| Example 77 | 4-(2-(2-Carboxy-ethyl)-3-{6-[3-(2,3-dihydro-benzo[1,4]dioxin-6-yl)-5-methylcarbamoyl-phenoxy]-hexyl}-phenoxy)-butyric acid | IC50 = 2.41 nM |
| Example 85 | 4-{2-(2-Carboxy-ethyl)-3-[6-(3-dimethylcarbamoyl-5-thiophen-3-yl-phenoxy)-hexyl]-phenoxy}-butyric acid | IC50 = 0.28 nM |
| Example 105 | 4-{2-(2-Carboxy-ethyl)-3-[6-(5-dimethylcarbamoyl-3'-fluoro-4'-methyl-biphenyl-3-yloxy)-hexyl]-phenoxy}-butyric acid | IC50 = 0.79 nM |
| Example 112 | 4-{2-(2-Carboxy-ethyl)-3-[6-(5-dimethylcarbamoyl-4'-methyl-biphenyl-3-yloxy)-hexyl]-phenoxy}-butyric acid | IC50 = 0.24 nM |
| Example 118 | 4-(2-(2-Carboxy-ethyl)-3-{7-[5-(4-methyl-piperazine-1-carbonyl)-biphenyl-3-yl]-heptyl}-phenoxy)-butyric acid | IC50 = 19.51 nM |
| Example 122 | 4-{2-(2-Carboxy-ethyl)-3-[7-(5-dimethylcarbamoyl-4'-hydroxy-biphenyl-3-yl)-hept-6-ynyl]-phenoxy}-butyric acid | IC50 = 15.64 nM |

It is to be understood that the invention is not limited to the particular embodiments of the invention described above, as variations of the particular embodiments may be made and still fall within the scope of the appended claims.

What is claimed is:
1. A compound of formula (I):

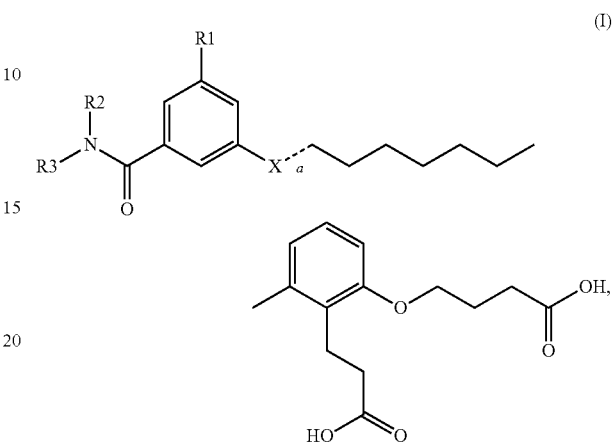

wherein:
R¹ is
  phenyl, unsubstituted or mono- or bi-substituted with alkoxy, halogen, hydroxy, lower alkyl, amino or amino-lower alkyl,
  heteroaryl, unsubstituted or substituted with lower alkyl or halogen,
  benzo[1,3]dioxole, unsubstituted or substituted with lower alkyl,
  dihydro-benzo[1,4]dioxine, unsubstituted or substituted with lower alkyl,
  benzo[b][1,4]dioxepine, unsubstituted or substituted with lower alkyl,
  dihydro-benzofuran, unsubstituted or substituted with lower alkyl, or
  benzo[1,4]oxazin, unsubstituted or substituted with lower alkyl;
R² and R³, independently of each other, are:
  hydrogen,
  lower alkyl,
  cycloalkyl,
  phenyl,
  lower alkyl-cycloalkyl,
  lower alkyl-heteroaryl,
  lower alkyl-alkoxy,
  alkoxy-lower alkyl,
  lower alkyl-heterocycloalkyl, unsubstituted or substituted with lower alkyl,
  C(O)-amino,
  lower alkyl-phenyl, said phenyl being unsubstituted or mono- or bi-substituted with lower alkyl, halogen, alkoxy or O-haloloweralkyl,
  benzo[1,3]dioxole, unsubstituted or substituted with lower alkyl,
  dihydro-benzo[1,4]dioxine, unsubstituted or substituted with lower alkyl,
  benzo[b][1,4]dioxepine, unsubstituted or substituted with lower alkyl,
  benzofuran, unsubstituted or substituted with lower alkyl,
  benzo[1,4]oxazin, unsubstituted or substituted with lower alkyl, CH$_2$-benzo[1,3]dioxole, unsubstituted or substituted with lower alkyl,
CH$_2$-dihydro-benzo[1,4]dioxine, unsubstituted or substituted with lower alkyl,
CH$_2$-benzo[b][1,4]dioxepine, unsubstituted or substituted with lower alkyl,
CH$_2$-benzofuran, unsubstituted or substituted with lower alkyl
CH$_2$-benzo[1,4]oxazin, unsubstituted or substituted with lower alkyl, or
R$^2$ and R$^3$, together with the nitrogen atom to which they are attached, form a heterocycloalkyl ring, optionally having a second heteroatom from N, O or S, said heterocycloalkyl ring being unsubstituted or mono- or bi-substituted with halogen, lower alkyl, carbonyl, C(=O) or hydroxy;
X is O or C; and
"a" is a single bond or an alkynyl bond,
and pharmaceutically acceptable salts thereof.

2. The compound according to claim 1, wherein:
R$^1$ is -phenyl, unsubstituted or mono- or bi-substituted with alkoxy, halogen, hydroxy, lower alkyl, amino or amino-lower alkyl; and
R$^2$ and R$^3$, independently of each other, are:
hydrogen,
lower alkyl,
cycloalkyl,
phenyl,
lower alkyl-cycloalkyl,
lower alkyl-heteroaryl,
lower alkyl-alkoxy,
alkoxy-lower alkyl,
lower alkyl-heterocycloalkyl, unsubstituted or substituted with lower alkyl,
C(O)-amino,
lower alkyl-phenyl, said phenyl being unsubstituted or mono- or bi-substituted with lower alkyl, halogen, alkoxy or O-haloloweralkyl,
benzo[1,3]dioxole, unsubstituted or substituted with lower alkyl,
dihydro-benzo[1,4]dioxine, unsubstituted or substituted with lower alkyl,
benzo[b][1,4]dioxepine, unsubstituted or substituted with lower alkyl,
benzofuran, unsubstituted or substituted with lower alkyl,
benzo[1,4]oxazin, unsubstituted or substituted with lower alkyl,
CH$_2$-benzo[1,3]dioxole, unsubstituted or substituted with lower alkyl,
CH$_2$-dihydro-benzo[1,4]dioxine, unsubstituted or substituted with lower alkyl,
CH$_2$-benzo[b][1,4]dioxepine, unsubstituted or substituted with lower alkyl,
CH$_2$-benzofuran, unsubstituted or substituted with lower alkyl.

3. The compound according to claim 1, wherein:
R$^1$ is phenyl, unsubstituted or mono- or bi-substituted with alkoxy, halogen, hydroxy, lower alkyl, amino or amino-lower alkyl; and
R$^2$ and R$^3$, together with the nitrogen atom to which they are attached, form a heterocycloalkyl ring, optionally having a second heteroatom from N, O or S, said heterocycloalkyl ring being unsubstituted or mono- or bi-substituted with halogen, lower alkyl, carbonyl, C(=O) or hydroxy.

4. The compound according to claim 1, wherein:
R$^1$ is heteroaryl, unsubstituted or substituted with lower alkyl or halogen; and
R$^2$ and R$^3$, independently of each other, are:
hydrogen,
lower alkyl,
cycloalkyl,
phenyl,
lower alkyl-cycloalkyl,
lower alkyl-heteroaryl,
lower alkyl-alkoxy,
alkoxy-lower alkyl,
lower alkyl-heterocycloalkyl, unsubstituted or substituted with lower alkyl,
C(O)-amino,
lower alkyl-phenyl, said phenyl being unsubstituted or mono- or bi-substituted with lower alkyl, halogen, alkoxy or O-haloloweralkyl,
benzo[1,3]dioxole, unsubstituted or substituted with lower alkyl,
dihydro-benzo[1,4]dioxine, unsubstituted or substituted with lower alkyl,
benzo[b][1,4]dioxepine, unsubstituted or substituted with lower alkyl,
benzofuran, unsubstituted or substituted with lower alkyl,
benzo[1,4]oxazin, unsubstituted or substituted with lower alkyl,
CH$_2$-benzo[1,3]dioxole, unsubstituted or substituted with lower alkyl,
CH$_2$-dihydro-benzo[1,4]dioxine, unsubstituted or substituted with lower alkyl,
CH$_2$-benzo[b][1,4]dioxepine, unsubstituted or substituted with lower alkyl,
CH$_2$-benzofuran, unsubstituted or substituted with lower alkyl.

5. The compound according to claim 1, wherein:
R$^1$ is heteroaryl, unsubstituted or substituted with lower alkyl or halogen; and
R$^2$ and R$^3$, together with the nitrogen atom to which they are attached, form a heterocycloalkyl ring, optionally having a second heteroatom from N, O or S, said heterocycloalkyl ring being unsubstituted or mono- or bi-substituted with halogen, lower alkyl, carbonyl, C(=O) or hydroxy.

6. The compound according to claim 1, wherein:
R$^1$ is
benzo[1,3]dioxole, unsubstituted or substituted with lower alkyl,
dihydro-benzo[1,4]dioxine, unsubstituted or substituted with lower alkyl,
benzo[b][1,4]dioxepine, unsubstituted or substituted with lower alkyl,
benzofuran, unsubstituted or substituted with lower alkyl, or
benzo[1,4]oxazin, unsubstituted or substituted with lower alkyl; and
R$^2$ and R$^3$, independently of each other, are:
hydrogen,
lower alkyl,
cycloalkyl,
phenyl,
lower alkyl-cycloalkyl,
lower alkyl-heteroaryl,
lower alkyl-alkoxy,
alkoxy-lower alkyl,
lower alkyl-heterocycloalkyl, unsubstituted or substituted with lower alkyl, C(O)-amino,
lower alkyl-phenyl, said phenyl being unsubstituted or mono- or bi-substituted with lower alkyl, halogen, alkoxy or O-haloloweralkyl,
benzo[1,3]dioxole, unsubstituted or substituted with lower alkyl,
dihydro-benzo[1,4]dioxine, unsubstituted or substituted with lower alkyl,
benzo[b][1,4]dioxepine, unsubstituted or substituted with lower alkyl,
benzofuran, unsubstituted or substituted with lower alkyl,
benzo[1,4]oxazin, unsubstituted or substituted with lower alkyl,
$CH_2$-benzo[1,3]dioxole, unsubstituted or substituted with lower alkyl,
$CH_2$-dihydro-benzo[1,4]dioxine, unsubstituted or substituted with lower alkyl,
$CH_2$-benzo[b][1,4]dioxepine, unsubstituted or substituted with lower alkyl,
$CH_2$-benzofuran, unsubstituted or substituted with lower alkyl.

7. The compound according to claim 1, wherein:
$R^1$ is
benzo[1,3]dioxole, unsubstituted or substituted with lower alkyl,
dihydro-benzo[1,4]dioxine, unsubstituted or substituted with lower alkyl,
benzo[b][1,4]dioxepine, unsubstituted or substituted with lower alkyl,
benzofuran, unsubstituted or substituted with lower alkyl, or
benzo[1,4]oxazin, unsubstituted or substituted with lower alkyl; and
$R^2$ and $R^3$, together with the nitrogen atom to which they are attached, form a heterocycloalkyl ring, optionally having a second heteroatom from N, O or S, said heterocycloalkyl ring being unsubstituted or mono- or bi-substituted with halogen, lower alkyl, carbonyl, C(=O) or hydroxy.

8. The compound according to claim 1, wherein X is O.
9. The compound according to claim 1, wherein X is C.
10. The compound according to claim 1, wherein "a" is a single bond.
11. The compound according to claim 1, wherein $R^1$ is thiophene, benzo[1,3]dioxol or dihydro-benzo[1,4]dioxine.
12. The compound according to claim 1, wherein $R^2$ and $R^3$, independently of each other, are hydrogen, methyl, ethyl or cyclopropyl.
13. The compound according to claim 1, wherein the heterocycloalkyl ring formed from $R^2$ and $R^3$ is pyrrolidine, piperidine, piperazine, morpholine, [1,4]diazepane, 1-methyl-[1,4]diazepane or 1-methyl-piperazine.

14. The compound according to claim 1, wherein said compound is:
4-[3-{6-[3-Benzo[1,3]dioxol-5-yl-5-(piperazine-1-carbonyl)-phenoxy]-hexyl}-2-(2-carboxy-ethyl)-phenoxy]-butyric acid,
4-[3-[6-(3-Benzo[1,3]dioxol-5-yl-5-cyclopropylcarbamoyl-phenoxy)-hexyl]-2-(2-carboxy-ethyl)-phenoxy]-butyric acid,
4-[3-[6-(3-Benzo[1,3]dioxol-5-yl-5-dimethylcarbamoyl-phenoxy)-hexyl]-2-(2-carboxy-ethyl)-phenoxy]-butyric acid,
4-[3-{6-[3-Benzo[1,3]dioxol-5-yl-5-(4-methyl-[1,4]diazepane-1-carbonyl)-phenoxy]-hexyl}-2-(2-carboxy-ethyl)-phenoxy]-butyric acid,
4-[3-[6-(3-Benzo[1,3]dioxol-5-yl-5-carbamoyl-phenoxy)-hexyl]-2-(2-carboxy-ethyl)-phenoxy]-butyric acid,
4-[3-{6-[3-Benzo[1,3]dioxol-5-yl-5-(piperidine-1-carbonyl)-phenoxy]-hexyl}-2-(2-carboxy-ethyl)-phenoxy]-butyric acid,
4-[3-[6-(3-Benzo[1,3]dioxol-5-yl-5-cyclobutylcarbamoyl-phenoxy)-hexyl]-2-(2-carboxy-ethyl)-phenoxy]-butyric acid,
4-(2-(2-Carboxy-ethyl)-3-{6-[5-(4-methyl-piperazine-1-carbonyl)-biphenyl-3-yloxy]-hexyl}-phenoxy)-butyric acid,
4-{2-(2-Carboxy-ethyl)-3-[6-(5-dimethylcarbamoyl-4'-methyl-biphenyl-3-yloxy)-hexyl]-phenoxy}-butyric acid,
4-[3-{6-[3-Benzo[1,3]dioxol-5-yl-5-(ethyl-methyl-carbamoyl)-phenoxy]-hexyl}-2-(2-carboxy-ethyl)-phenoxy]-butyric acid,
4-(2-(2-Carboxy-ethyl)-3-{6-[3'-fluoro-5-(piperazine-1-carbonyl)-biphenyl-3-yloxy]-hexyl}-phenoxy)-butyric acid,
4-{2-(2-Carboxy-ethyl)-3-[6-(3-dimethylcarbamoyl-5-thiophen-3-yl-phenoxy)-hexyl]-phenoxy}-butyric acid,
4-[3-[6-(3-Benzo[1,3]dioxol-5-yl-5-isopropylcarbamoyl-phenoxy)-hexyl]-2-(2-carboxy-ethyl)-phenoxy]-butyric acid,
4-(2-(2-carboxy-ethyl)-3-{6-[3-([1,4]diazepane-1-carbonyl)-5-thiophen-3-yl-phenoxy]-hexyl}-phenoxy)-butyric acid or
4-(2-(2-Carboxy-ethyl)-3-{6-[5-([1,4]diazepane-1-carbonyl)-3'-fluoro-biphenyl-3-yloxy]-hexyl}-phenoxy)-butyric acid.

15. A pharmaceutical composition, comprising a therapeutically effective amount of a compound according to claim 1 or a pharmaceutically acceptable salt thereof and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,989,454 B2 | Page 1 of 1 |
| APPLICATION NO. | : 12/326349 | |
| DATED | : August 2, 2011 | |
| INVENTOR(S) | : Dominique et al. | |

It is certified that error appears in the above-identified patent and that said Letters Patent is hereby corrected as shown below:

Title page

In Column 1, Item (60) please delete "December 17, 2002" and insert:
--December 17, 2007--

In Column 2, Item (74) please delete "George E. Johnston" and insert:
--George W. Johnston--

Signed and Sealed this
Tenth Day of April, 2012

David J. Kappos
*Director of the United States Patent and Trademark Office*